United States Patent
Duryea et al.

(10) Patent No.: US 12,390,665 B1
(45) Date of Patent: *Aug. 19, 2025

(54) HISTOTRIPSY SYSTEMS AND METHODS

(71) Applicant: HistoSonics, Inc., Plymouth, MN (US)

(72) Inventors: Alexander P. Duryea, Ann Arbor, MI (US); Connor Edsall, Ann Arbor, MI (US); Tyler I. Gerhardson, Ann Arbor, MI (US)

(73) Assignee: HistoSonics, Inc., Plymouth, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/498,979

(22) Filed: Oct. 31, 2023

Related U.S. Application Data

(63) Continuation of application No. 18/497,856, filed on Oct. 30, 2023.

(60) Provisional application No. 63/381,401, filed on Oct. 28, 2022.

(51) Int. Cl.
*A61N 7/00* (2006.01)

(52) U.S. Cl.
CPC ........ *A61N 7/00* (2013.01); *A61N 2007/0039* (2013.01); *A61N 2007/0095* (2013.01)

(58) Field of Classification Search
CPC .............. A61N 7/00; A61N 2007/0039; A61N 2007/0095
See application file for complete search history.

(56) References Cited

U.S. PATENT DOCUMENTS

| | | |
|---|---|---|
| 3,243,497 A | 3/1966 | Kendall et al. |
| 3,679,021 A | 7/1972 | Goldberg et al. |
| 3,693,415 A * | 9/1972 | Whittington .......... A61B 8/12 367/105 |
| 3,879,699 A | 4/1975 | Pepper |
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |

(Continued)

FOREIGN PATENT DOCUMENTS

| | | |
|---|---|---|
| AU | 2017222925 B2 | 11/2021 |
| BR | 112018017326 B1 | 12/2022 |

(Continued)

OTHER PUBLICATIONS

Feasibility of Using Ultrasound Phased Arrays for MRI Monitored Noninvasive Surgery (Year: 1996).*

(Continued)

*Primary Examiner* — Hien N Nguyen
(74) *Attorney, Agent, or Firm* — Shay Glenn LLP

(57) ABSTRACT

A histotripsy therapy system configured for the treatment of tissue is provided, which may include any number of features. Provided herein are systems and methods that provide efficacious non-invasive and minimally invasive therapeutic, diagnostic and research procedures. In particular, provided herein are optimized systems and methods that provide targeted, efficacious histotripsy in a variety of different regions and under a variety of different conditions without causing undesired tissue damage to intervening/non-target tissues or structures.

17 Claims, 15 Drawing Sheets

(56) References Cited

U.S. PATENT DOCUMENTS

| | | |
|---|---|---|
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,343 A | 11/1984 | Beyer et al. |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,928,672 A * | 5/1990 | Grasser ............... A61B 17/2258 601/4 |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,078,140 A | 1/1992 | Kwoh |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,195,509 A | 3/1993 | Rentschler et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,492,126 A | 2/1996 | Hennige et al. |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,665,054 A * | 9/1997 | Dory .................. A61N 7/02 601/3 |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,683,064 A | 11/1997 | Copeland et al. |
| 5,694,936 A | 12/1997 | Fujimoto et al. |
| 5,695,460 A | 12/1997 | Siegel et al. |
| 5,717,657 A | 2/1998 | Ruffa |
| 5,720,287 A | 2/1998 | Chapelon et al. |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,800,365 A | 9/1998 | Zhong et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,928,169 A | 7/1999 | Schitzle et al. |
| 5,932,807 A | 8/1999 | Mallart |
| 5,947,904 A | 9/1999 | Hossack et al. |
| 6,001,069 A | 12/1999 | Tachibana et al. |
| 6,007,499 A | 12/1999 | Martin et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |

(56) References Cited

U.S. PATENT DOCUMENTS

| | | |
|---|---|---|
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckal et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,022,107 B2 | 7/2018 | Thornton et al. |
| 10,046,179 B2 | 8/2018 | Oskar-Kohler |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,751,015 B2 | 8/2020 | Anderson et al. |
| 10,751,125 B2 | 8/2020 | Levy et al. |
| 10,765,892 B1 | 9/2020 | Vitek et al. |
| 10,772,646 B2 | 9/2020 | Lu et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,900,933 B2 | 1/2021 | Prus et al. |
| 10,905,394 B2 | 2/2021 | Stigall et al. |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Corl |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Corl |
| 11,026,591 B2 | 6/2021 | Burkett et al. |
| 11,040,140 B2 | 6/2021 | Unser et al. |
| 11,058,399 B2 | 7/2021 | Xu et al. |
| 11,071,522 B2 | 7/2021 | Hynynen et al. |
| 11,103,731 B2 | 8/2021 | Vortman et al. |
| 11,112,473 B2 | 9/2021 | Assif |
| 11,119,552 B2 | 9/2021 | Spencer et al. |
| 11,120,896 B2 | 9/2021 | Balignasay et al. |
| 11,123,019 B2 | 9/2021 | Merritt et al. |
| 11,123,575 B2 | 9/2021 | Vortman et al. |
| 11,135,454 B2 | 10/2021 | Xu et al. |
| 11,141,063 B2 | 10/2021 | Kemp et al. |
| 11,141,131 B2 | 10/2021 | Stigall et al. |
| 11,160,513 B2 | 11/2021 | Anderson et al. |
| 11,205,507 B2 | 12/2021 | Anderson et al. |
| 11,219,748 B2 | 1/2022 | Burkett et al. |
| 11,224,349 B2 | 1/2022 | Davies et al. |
| 11,224,403 B2 | 1/2022 | Corl |
| 11,224,407 B2 | 1/2022 | Wrolstad et al. |
| 11,234,649 B2 | 2/2022 | Matsubara et al. |
| 11,246,533 B2 | 2/2022 | Henderson et al. |
| 11,246,565 B2 | 2/2022 | Corl |
| 11,253,225 B2 | 2/2022 | Hancock et al. |

(56) References Cited

U.S. PATENT DOCUMENTS

| | | |
|---|---|---|
| 11,260,160 B2 | 3/2022 | Matsubara et al. |
| 11,272,845 B2 | 3/2022 | Cheline et al. |
| 11,272,904 B2 | 3/2022 | Vortman et al. |
| 11,291,866 B2 | 4/2022 | Levy et al. |
| 11,298,030 B2 | 4/2022 | Davies et al. |
| 11,309,071 B2 | 4/2022 | Anderson |
| 11,311,271 B2 | 4/2022 | Stigall et al. |
| 11,324,410 B2 | 5/2022 | Burkett |
| 11,350,906 B2 | 6/2022 | Castella et al. |
| 11,350,954 B2 | 6/2022 | De Cicco et al. |
| 11,364,042 B2 | 6/2022 | Maxwell et al. |
| 11,369,346 B2 | 6/2022 | De Cicco et al. |
| 11,369,994 B2 | 6/2022 | Greenberg et al. |
| 11,395,638 B2 | 7/2022 | Shin et al. |
| 11,406,334 B2 | 8/2022 | Merritt |
| 11,406,355 B2 | 8/2022 | Hoffman et al. |
| 11,406,498 B2 | 8/2022 | Stigall et al. |
| 11,408,987 B2 | 8/2022 | Vignon et al. |
| 11,413,017 B2 | 8/2022 | Stigall et al. |
| 11,419,580 B2 | 8/2022 | Stigall et al. |
| 11,426,140 B2 | 8/2022 | Sudol et al. |
| 11,432,795 B2 | 9/2022 | Merritt |
| 11,432,900 B2 | 9/2022 | Rakic et al. |
| 11,446,000 B2 | 9/2022 | Minas et al. |
| 11,452,496 B2 | 9/2022 | Minas et al. |
| 11,452,506 B2 | 9/2022 | Perez et al. |
| 11,471,215 B2 | 10/2022 | Stigall et al. |
| 11,484,294 B2 | 11/2022 | Hancock et al. |
| 11,510,632 B2 | 11/2022 | Begin et al. |
| 11,517,291 B2 | 12/2022 | Kantor et al. |
| 11,520,874 B2 | 12/2022 | Kennedy et al. |
| 11,524,183 B1 | 12/2022 | Garcia Gutierrez et al. |
| 11,527,001 B2 | 12/2022 | Brokman et al. |
| 11,547,389 B2 | 1/2023 | Shin et al. |
| 11,553,889 B2 | 1/2023 | Spencer et al. |
| 11,554,386 B2 | 1/2023 | Pernot et al. |
| 11,559,207 B2 | 1/2023 | Stigall et al. |
| 11,567,153 B2 | 1/2023 | Stormont et al. |
| 11,576,649 B2 | 2/2023 | Corl |
| 11,576,652 B2 | 2/2023 | De Cicco et al. |
| 11,583,193 B2 | 2/2023 | Groenland et al. |
| 11,589,835 B2 | 2/2023 | Stigall et al. |
| 11,596,351 B2 | 3/2023 | Nair |
| 11,596,384 B2 | 3/2023 | Nair et al. |
| 11,596,385 B2 | 3/2023 | Stigall et al. |
| 11,596,387 B2 | 3/2023 | Song |
| 11,596,389 B2 | 3/2023 | Nair |
| 11,596,469 B2 | 3/2023 | Nair |
| 11,622,746 B2 | 4/2023 | Minas et al. |
| 11,638,576 B2 | 5/2023 | Groenland et al. |
| 11,647,989 B2 | 5/2023 | Hope Simpson et al. |
| 11,648,424 B2 * | 5/2023 | Cannata ............... A61B 34/30 601/2 |
| 11,653,895 B2 | 5/2023 | Stigall et al. |
| 11,660,070 B2 | 5/2023 | Stigall et al. |
| 11,666,245 B2 | 6/2023 | Rajguru et al. |
| 11,666,307 B2 | 6/2023 | Unser |
| 11,672,433 B2 | 6/2023 | Park et al. |
| 11,672,552 B2 | 6/2023 | Pasquino et al. |
| 11,672,953 B2 | 6/2023 | May |
| 11,684,342 B2 | 6/2023 | Groenland et al. |
| 11,684,807 B2 | 6/2023 | Vortman et al. |
| 11,701,134 B2 | 7/2023 | Maxwell et al. |
| 11,707,207 B2 | 7/2023 | Stigall et al. |
| 11,707,254 B2 | 7/2023 | Di Tullio et al. |
| 11,733,881 B2 | 8/2023 | Perez |
| 11,737,728 B2 | 8/2023 | Davies et al. |
| 11,744,527 B2 | 9/2023 | Scott et al. |
| 11,744,547 B2 | 9/2023 | Hynynen |
| 11,759,169 B2 | 9/2023 | Corl |
| 11,759,174 B2 | 9/2023 | Saroha et al. |
| 11,766,237 B2 | 9/2023 | Anderson |
| 11,771,370 B2 | 10/2023 | Hynynen |
| 11,771,405 B2 | 10/2023 | Rhodes |
| 11,771,869 B2 | 10/2023 | Cicco |
| 11,779,307 B2 | 10/2023 | Norris et al. |
| 11,806,167 B2 | 11/2023 | Burkett |
| 11,813,484 B2 | 11/2023 | Cannata et al. |
| 11,813,485 B2 | 11/2023 | Xu et al. |
| 11,819,712 B2 | 11/2023 | Cain et al. |
| 11,854,687 B2 | 12/2023 | Keller |
| 11,857,362 B2 | 1/2024 | Wrolstad et al. |
| 11,857,807 B2 | 1/2024 | Levy et al. |
| 11,864,918 B2 | 1/2024 | Burkett et al. |
| 11,872,412 B2 | 1/2024 | Vortman et al. |
| 11,879,973 B2 | 1/2024 | Prus et al. |
| 11,883,235 B2 | 1/2024 | Stigall et al. |
| 11,890,025 B2 | 2/2024 | Stigall et al. |
| 11,890,136 B2 | 2/2024 | Stigall et al. |
| 11,890,137 B2 | 2/2024 | Jenkins et al. |
| 11,950,954 B2 | 4/2024 | Hyun et al. |
| 11,963,822 B2 | 4/2024 | Wrolstad |
| 11,986,682 B2 | 5/2024 | Prus et al. |
| 11,992,366 B2 | 5/2024 | Stigall et al. |
| 12,017,013 B2 | 6/2024 | Sasamine et al. |
| 12,035,919 B2 | 7/2024 | Unser |
| 12,036,066 B2 | 7/2024 | De Cicco et al. |
| 12,053,194 B2 | 8/2024 | Goertz et al. |
| 12,220,259 B2 | 2/2025 | Burkett et al. |
| 12,232,907 B2 | 2/2025 | Chao et al. |
| 12,246,195 B2 | 3/2025 | Levy et al. |
| 2001/0039420 A1 | 11/2001 | Burbank et al. |
| 2001/0041163 A1 | 11/2001 | Sugita |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0164213 A1 | 8/2004 | Stephan |
| 2004/0236248 A1 | 11/2004 | Svedman |
| 2004/0243021 A1 | 12/2004 | Murphy et al. |
| 2004/0249509 A1 | 12/2004 | Rogers et al. |
| 2004/0260214 A1 | 12/2004 | Echt et al. |
| 2005/0011296 A1 | 1/2005 | Koseki |
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0203399 A1 | 9/2005 | Vaezy et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0058678 A1 | 3/2006 | Vitek et al. |
| 2006/0060991 A1 | 3/2006 | Holsteyns et al. |
| 2006/0074303 A1 | 4/2006 | Chornenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0184166 A1 | 8/2006 | Valle et al. |
| 2006/0206028 A1 | 9/2006 | Lee et al. |
| 2006/0229659 A1 | 10/2006 | Gifford et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |

(56) References Cited

U.S. PATENT DOCUMENTS

| | | |
|---|---|---|
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0300485 A1 | 12/2008 | Liu et al. |
| 2008/0312561 A1 | 12/2008 | Chauhan |
| 2008/0319356 A1 * | 12/2008 | Cain ................ A61B 17/22004 600/300 |
| 2008/0319376 A1 | 12/2008 | Wilcox et al. |
| 2009/0012514 A1 | 1/2009 | Moonen et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0254008 A1 | 10/2009 | Shields, Jr. |
| 2009/0287083 A1 | 11/2009 | Kushculey et al. |
| 2009/0306502 A1 | 12/2009 | Lacoste |
| 2010/0011845 A1 | 1/2010 | Laugharn et al. |
| 2010/0042020 A1 | 2/2010 | Ben-Ezra |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0204578 A1 | 8/2010 | Schmidt et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0072970 A1 | 3/2011 | Slobodzian et al. |
| 2011/0112400 A1 | 5/2011 | Emery et al. |
| 2011/0118600 A1 | 5/2011 | Gertner |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0245671 A1 | 10/2011 | Sato |
| 2011/0251528 A1 | 10/2011 | Canney et al. |
| 2011/0257524 A1 | 10/2011 | Gertner |
| 2011/0263967 A1 | 10/2011 | Bailey et al. |
| 2011/0270136 A1 | 11/2011 | Vitek et al. |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2012/0281902 A1 * | 11/2012 | Oikawa ............... G01S 7/52034 382/131 |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0172739 A1 | 7/2013 | Paladini |
| 2013/0190623 A1 | 7/2013 | Bertolina et al. |
| 2013/0190661 A1 | 7/2013 | Wing et al. |
| 2013/0255426 A1 | 10/2013 | Kassow et al. |
| 2013/0303906 A1 | 11/2013 | Cain et al. |
| 2014/0030806 A1 | 1/2014 | Dudley et al. |
| 2014/0039358 A1 | 2/2014 | Zhou et al. |
| 2014/0046181 A1 | 2/2014 | Benchimol et al. |
| 2014/0058293 A1 | 2/2014 | Hynynen et al. |
| 2014/0058294 A1 | 2/2014 | Gross et al. |
| 2014/0073995 A1 | 3/2014 | Teofilovic et al. |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0112107 A1 | 4/2014 | Guo et al. |
| 2014/0128734 A1 | 5/2014 | Genstler et al. |
| 2014/0200489 A1 | 7/2014 | Behar et al. |
| 2014/0243664 A1 | 8/2014 | El-Sayed et al. |
| 2014/0316269 A1 | 10/2014 | Zhang et al. |
| 2014/0324034 A1 | 10/2014 | Assaf et al. |
| 2014/0330124 A1 | 11/2014 | Carol |
| 2014/0378832 A1 | 12/2014 | Sanghvi et al. |
| 2014/0378964 A1 | 12/2014 | Pearson |
| 2015/0011875 A1 | 1/2015 | Noordhoek et al. |
| 2015/0063668 A1 | 3/2015 | You et al. |
| 2015/0073261 A1 | 3/2015 | Kohler et al. |
| 2015/0080926 A1 | 3/2015 | Emery |
| 2015/0148659 A1 | 5/2015 | Vahala |
| 2015/0151141 A1 | 6/2015 | Arnal et al. |
| 2015/0190121 A1 | 7/2015 | Slayton et al. |
| 2015/0190659 A1 | 7/2015 | Kolher |
| 2015/0196239 A1 | 7/2015 | Meehan et al. |
| 2015/0224347 A1 | 8/2015 | Barthe et al. |
| 2015/0257779 A1 | 9/2015 | Sinelnikov et al. |
| 2015/0258352 A1 | 9/2015 | Lin et al. |
| 2015/0273246 A1 | 10/2015 | Darlington et al. |
| 2015/0297177 A1 | 10/2015 | Boctor et al. |
| 2016/0004933 A1 | 1/2016 | Hu et al. |
| 2016/0114194 A1 | 4/2016 | Gertner |
| 2016/0120572 A1 | 5/2016 | Lee |
| 2016/0135782 A1 | 5/2016 | Chen et al. |
| 2016/0151618 A1 | 6/2016 | Powers et al. |
| 2016/0184614 A1 | 6/2016 | Matula et al. |
| 2016/0206341 A1 | 7/2016 | Slayton |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0303166 A1 | 10/2016 | Katz et al. |
| 2016/0331583 A1 | 11/2016 | Geringer |
| 2016/0331585 A1 | 11/2016 | Kim |
| 2016/0339273 A1 | 11/2016 | Al Mayiah |
| 2016/0345938 A1 * | 12/2016 | Tanter .................... A61B 8/485 |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0100145 A1 | 4/2017 | Khoklova et al. |
| 2017/0120080 A1 | 5/2017 | Phillips et al. |
| 2017/0165046 A1 | 6/2017 | Johnson et al. |
| 2017/0183062 A1 | 6/2017 | Lee |

(56) References Cited

U.S. PATENT DOCUMENTS

| | | |
|---|---|---|
| 2017/0232277 A1 | 8/2017 | Hall et al. |
| 2017/0281983 A1 | 10/2017 | Marquet et al. |
| 2018/0000444 A1 | 1/2018 | Dayton et al. |
| 2018/0028841 A1 | 2/2018 | Konofagou et al. |
| 2018/0064412 A1 | 3/2018 | Messas et al. |
| 2018/0161086 A1 | 6/2018 | Davalos et al. |
| 2018/0169444 A1 | 6/2018 | Averkiou et al. |
| 2018/0206816 A1 | 7/2018 | Prus et al. |
| 2018/0236271 A1 | 8/2018 | Tanter et al. |
| 2018/0317884 A1 | 11/2018 | Chapelon et al. |
| 2019/0000422 A1 | 1/2019 | West et al. |
| 2019/0023804 A1 | 1/2019 | Onik et al. |
| 2019/0275353 A1 | 9/2019 | Cannata et al. |
| 2019/0282294 A1 | 9/2019 | Davalos et al. |
| 2019/0314045 A1 | 10/2019 | Cunitz et al. |
| 2019/0320904 A1 | 10/2019 | Mei |
| 2019/0323086 A1 | 10/2019 | Leuthardt et al. |
| 2019/0328500 A1 | 10/2019 | Cichon et al. |
| 2020/0010575 A1 | 1/2020 | Hode et al. |
| 2020/0055085 A1 | 2/2020 | Taffier |
| 2020/0078608 A1 | 3/2020 | Maxwell et al. |
| 2020/0107843 A1 | 4/2020 | Goertz et al. |
| 2020/0182989 A1 | 6/2020 | Freeman et al. |
| 2020/0194117 A1 | 6/2020 | Krieger et al. |
| 2020/0253550 A1 | 8/2020 | Nair |
| 2020/0254285 A1 | 8/2020 | Jang et al. |
| 2020/0260964 A1 | 8/2020 | Collins et al. |
| 2020/0282239 A1 | 9/2020 | Beder et al. |
| 2020/0305842 A1 | 10/2020 | Rosenzweig et al. |
| 2020/0323515 A1 | 10/2020 | Levy |
| 2020/0330039 A1 | 10/2020 | Burkett et al. |
| 2020/0330075 A1 | 10/2020 | O'Reilly et al. |
| 2020/0353293 A1 | 11/2020 | Khokhlova et al. |
| 2020/0367835 A1 | 11/2020 | Anderson |
| 2020/0375576 A1 | 12/2020 | Moulton |
| 2020/0405258 A1 | 12/2020 | Dayton et al. |
| 2020/0405259 A1 | 12/2020 | Merritt |
| 2021/0000541 A1 | 1/2021 | Levy et al. |
| 2021/0022703 A1 | 1/2021 | Nair |
| 2021/0022714 A1 | 1/2021 | Zagrodsky et al. |
| 2021/0100527 A1 | 4/2021 | Martin |
| 2021/0108866 A1 | 4/2021 | Lucht et al. |
| 2021/0161398 A1 | 6/2021 | Millett et al. |
| 2021/0169515 A1 | 6/2021 | Pahk et al. |
| 2021/0170204 A1 | 6/2021 | Vortman et al. |
| 2021/0170205 A1 | 6/2021 | Vortman et al. |
| 2021/0187331 A1 | 6/2021 | Zadicario et al. |
| 2021/0196295 A1 | 7/2021 | Goudot et al. |
| 2021/0220607 A1 | 7/2021 | Sasamine et al. |
| 2021/0330294 A1 | 10/2021 | Hynynen et al. |
| 2021/0353161 A1 | 11/2021 | Merritt et al. |
| 2021/0386451 A1 | 12/2021 | Escudero et al. |
| 2021/0401400 A1 | 12/2021 | Sheehan et al. |
| 2022/0008036 A1 | 1/2022 | Gulsen et al. |
| 2022/0022845 A1 | 1/2022 | Corl |
| 2022/0043143 A1 | 2/2022 | Prus et al. |
| 2022/0079563 A1 | 3/2022 | Kemp |
| 2022/0087640 A1 | 3/2022 | Minas et al. |
| 2022/0166462 A1 | 5/2022 | Deurenberg et al. |
| 2022/0167920 A1 | 6/2022 | Margolis |
| 2022/0168470 A1 | 6/2022 | Ricotti et al. |
| 2022/0196771 A1 | 6/2022 | Zur et al. |
| 2022/0203139 A1 | 6/2022 | Shapira |
| 2022/0219019 A1 | 7/2022 | Xu et al. |
| 2022/0233890 A1 | 7/2022 | Hynynen et al. |
| 2022/0240890 A1 | 8/2022 | Hancock et al. |
| 2022/0257329 A1 | 8/2022 | Stigall et al. |
| 2022/0280233 A1 | 9/2022 | Park et al. |
| 2022/0280367 A1 | 9/2022 | Diodato et al. |
| 2022/0296211 A1 | 9/2022 | Saroha et al. |
| 2022/0338750 A1 | 10/2022 | Allen et al. |
| 2022/0346756 A1 | 11/2022 | Chen |
| 2022/0370025 A1 | 11/2022 | Regensburger et al. |
| 2022/0386970 A1 | 12/2022 | Merritt |
| 2022/0395333 A1 | 12/2022 | Merritt et al. |
| 2022/0409171 A1 | 12/2022 | Sudol et al. |
| 2022/0409858 A1 | 12/2022 | Lin |
| 2023/0000466 A1 | 1/2023 | Levy et al. |
| 2023/0000469 A1 | 1/2023 | Prus et al. |
| 2023/0008714 A1 | 1/2023 | Rajguru et al. |
| 2023/0012365 A1 | 1/2023 | Alpert et al. |
| 2023/0024998 A1 | 1/2023 | Greenberg |
| 2023/0031859 A1 | 2/2023 | Davies et al. |
| 2023/0037603 A1 | 2/2023 | Pombo et al. |
| 2023/0038498 A1 | 2/2023 | Xu et al. |
| 2023/0038543 A1 | 2/2023 | Minas et al. |
| 2023/0042834 A1 | 2/2023 | Henderson et al. |
| 2023/0045488 A1 | 2/2023 | Rajguru et al. |
| 2023/0050732 A1 | 2/2023 | Hancock et al. |
| 2023/0061534 A1 | 3/2023 | Stopek |
| 2023/0073447 A1 | 3/2023 | Minas et al. |
| 2023/0100912 A1 | 3/2023 | Amar et al. |
| 2023/0112722 A1 | 4/2023 | Hoffman et al. |
| 2023/0114972 A1 | 4/2023 | Bigham et al. |
| 2023/0121688 A1 | 4/2023 | Begin et al. |
| 2023/0145064 A1 | 5/2023 | Vortman et al. |
| 2023/0181140 A1 | 6/2023 | Cohen et al. |
| 2023/0181156 A1 | 6/2023 | Cohen et al. |
| 2023/0190119 A1 | 6/2023 | Groenland et al. |
| 2023/0190215 A1 | 6/2023 | Nachtomy et al. |
| 2023/0190224 A1 | 6/2023 | Rajguru et al. |
| 2023/0190225 A1 | 6/2023 | Cohen et al. |
| 2023/0190226 A1 | 6/2023 | Rajguru et al. |
| 2023/0190227 A1 | 6/2023 | Cohen et al. |
| 2023/0190228 A1 | 6/2023 | Cohen et al. |
| 2023/0190229 A1 | 6/2023 | Cohen et al. |
| 2023/0190230 A1 | 6/2023 | Yang et al. |
| 2023/0191162 A1 | 6/2023 | Yau et al. |
| 2023/0196569 A1 | 6/2023 | Cohen et al. |
| 2023/0200899 A1 | 6/2023 | Nair |
| 2023/0201553 A1 | 6/2023 | Levy et al. |
| 2023/0218230 A1 | 7/2023 | Wu et al. |
| 2023/0218262 A1 | 7/2023 | Boutelle et al. |
| 2023/0218266 A1 | 7/2023 | Stigall et al. |
| 2023/0218269 A1 | 7/2023 | Alpert et al. |
| 2023/0218930 A1 | 7/2023 | Stopek et al. |
| 2023/0240615 A1 | 8/2023 | May et al. |
| 2023/0240647 A1 | 8/2023 | Minas et al. |
| 2023/0240792 A1 | 8/2023 | Rakic et al. |
| 2023/0255597 A1 | 8/2023 | O'Reilly et al. |
| 2023/0260601 A1 | 8/2023 | Abel et al. |
| 2023/0263507 A1 | 8/2023 | Groenland et al. |
| 2023/0270388 A1 | 8/2023 | Richardson et al. |
| 2023/0293148 A1 | 9/2023 | Stigall et al. |
| 2023/0293149 A1 | 9/2023 | Stigall et al. |
| 2023/0309859 A1 | 10/2023 | Sreedhar et al. |
| 2023/0310899 A1 | 10/2023 | Hall et al. |
| 2023/0310900 A1 | 10/2023 | Cannata et al. |
| 2023/0310901 A1 | 10/2023 | Cannata et al. |
| 2023/0320600 A1 | 10/2023 | Tochterman et al. |
| 2023/0321327 A1* | 10/2023 | Maxwell ............ A61L 31/145 424/423 |
| 2023/0321398 A1 | 10/2023 | May |
| 2023/0329559 A1 | 10/2023 | Xu et al. |
| 2023/0333617 A1 | 10/2023 | Spencer et al. |
| 2023/0334659 A1 | 10/2023 | Marama et al. |
| 2023/0334677 A1 | 10/2023 | Sturm |
| 2023/0338010 A1 | 10/2023 | Sturm |
| 2023/0372025 A1 | 11/2023 | Van der Zaag et al. |
| 2023/0381544 A1 | 11/2023 | Penot et al. |
| 2023/0389891 A1 | 12/2023 | Cohen et al. |
| 2023/0398381 A1 | 12/2023 | Vitek et al. |
| 2024/0000422 A1 | 1/2024 | Corl |
| 2024/0000426 A1 | 1/2024 | Davies et al. |
| 2024/0001157 A1 | 1/2024 | Cannata et al. |
| 2024/0001158 A1 | 1/2024 | Cannata et al. |
| 2024/0023928 A1 | 1/2024 | Di Tullio et al. |
| 2024/0023930 A1 | 1/2024 | Anderson |
| 2024/0023941 A1 | 1/2024 | Rhodes |
| 2024/0065632 A1 | 2/2024 | Burkett |
| 2024/0138807 A1 | 5/2024 | Minas |
| 2024/0139553 A1 | 5/2024 | Miller et al. |
| 2024/0165666 A1 | 5/2024 | Hynynen et al. |
| 2024/0188929 A1 | 6/2024 | Minas et al. |

(56) References Cited

U.S. PATENT DOCUMENTS

| | | |
|---|---|---|
| 2024/0188931 A1 | 6/2024 | Ossmann et al. |
| 2024/0189267 A1 | 6/2024 | Bogott et al. |
| 2024/0189628 A1 | 6/2024 | Grumbir et al. |
| 2024/0225592 A1 | 7/2024 | May et al. |
| 2024/0245374 A1 | 7/2024 | Jenkins et al. |
| 2024/0245390 A1 | 7/2024 | Winkler Brown et al. |
| 2024/0245465 A1 | 7/2024 | Jenkins et al. |
| 2024/0269491 A1 | 8/2024 | Xu et al. |
| 2024/0285249 A1 | 8/2024 | May |
| 2024/0408416 A1 | 12/2024 | Cannata et al. |
| 2025/0018227 A1 | 1/2025 | Son et al. |
| 2025/0040912 A1 | 2/2025 | Levy et al. |
| 2025/0041577 A1 | 2/2025 | Shapira et al. |
| 2025/0072872 A1 | 3/2025 | Nachtomy et al. |
| 2025/0090130 A1 | 3/2025 | Schell et al. |
| 2025/0090871 A1 | 3/2025 | Snell et al. |

FOREIGN PATENT DOCUMENTS

| | | |
|---|---|---|
| BR | 102023017634 A2 | 1/2025 |
| CA | 3073552 A1 | 3/2019 |
| CA | 3101381 A1 | 11/2019 |
| CA | 3055856 A1 | 4/2020 |
| CA | 3153080 A1 | 4/2021 |
| CA | 2910561 C | 7/2021 |
| CA | 2908740 C | 10/2021 |
| CA | 2980976 C | 3/2023 |
| CA | 2840014 C | 8/2023 |
| CN | 1669672 A | 9/2005 |
| CN | 1732031 A | 2/2006 |
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 104208822 A | 12/2014 |
| CN | 106999076 B | 8/2017 |
| CN | 109185113 A | 1/2019 |
| CN | 109219415 A | 1/2019 |
| CN | 109689160 A | 4/2019 |
| CN | 208725992 U | 4/2019 |
| CN | 111565642 A | 8/2020 |
| CN | 111655337 A | 9/2020 |
| CN | 111699022 A | 9/2020 |
| CN | 111712300 A | 9/2020 |
| CN | 111712301 A | 9/2020 |
| CN | 106999053 B | 10/2020 |
| CN | 107660137 B | 10/2020 |
| CN | 111757769 A | 10/2020 |
| CN | 112204412 A | 1/2021 |
| CN | 112236195 A | 1/2021 |
| CN | 106661535 B | 3/2021 |
| CN | 112533673 A | 3/2021 |
| CN | 112566694 A | 3/2021 |
| CN | 106999054 B | 5/2021 |
| CN | 106793997 B | 6/2021 |
| CN | 107530049 B | 6/2021 |
| CN | 112912011 A | 6/2021 |
| CN | 112912012 A | 6/2021 |
| CN | 112912013 A | 6/2021 |
| CN | 112969413 A | 6/2021 |
| CN | 112996445 A | 6/2021 |
| CN | 113167877 A | 7/2021 |
| CN | 113196080 A | 7/2021 |
| CN | 109196369 B | 8/2021 |
| CN | 109200484 B | 8/2021 |
| CN | 113316419 A | 8/2021 |
| CN | 113329788 A | 8/2021 |
| CN | 109640830 B | 10/2021 |
| CN | 113473917 A | 10/2021 |
| CN | 113507946 A | 10/2021 |
| CN | 113518588 A | 10/2021 |
| CN | 113705586 A | 11/2021 |
| CN | 110662575 B | 12/2021 |
| CN | 113905666 A | 1/2022 |
| CN | 114222536 A | 3/2022 |
| CN | 114366154 A | 4/2022 |
| CN | 114423362 A | 4/2022 |
| CN | 110248606 B | 6/2022 |
| CN | 115227992 A | 10/2022 |
| CN | 109843181 B | 11/2022 |
| CN | 115461000 A | 12/2022 |
| CN | 115515504 A | 12/2022 |
| CN | 109091768 B | 3/2023 |
| CN | 115779285 A | 3/2023 |
| CN | 115779287 A | 3/2023 |
| CN | 115813438 A | 3/2023 |
| CN | 111032157 B | 4/2023 |
| CN | 115916035 A | 4/2023 |
| CN | 110958858 B | 5/2023 |
| CN | 116172611 A | 5/2023 |
| CN | 111655337 B | 6/2023 |
| CN | 109416908 B | 7/2023 |
| CN | 116507295 A | 7/2023 |
| CN | 107529989 B | 8/2023 |
| CN | 111372522 B | 8/2023 |
| CN | 116617589 A | 8/2023 |
| CN | 112236195 B | 9/2023 |
| CN | 113615098 B | 9/2023 |
| CN | 114555247 B | 9/2023 |
| CN | 116744856 A | 9/2023 |
| CN | 116761554 A | 9/2023 |
| CN | 109416907 B | 10/2023 |
| CN | 117321444 A | 12/2023 |
| CN | 117500437 A | 2/2024 |
| CN | 117580499 A | 2/2024 |
| CN | 111212606 B | 3/2024 |
| CN | 113490459 B | 5/2024 |
| CN | 118042992 A | 5/2024 |
| CN | 118414127 A | 7/2024 |
| CN | 119367006 A | 1/2025 |
| CN | 112704620 B | 2/2025 |
| CN | 114287963 B | 2/2025 |
| DE | 3220751 A1 | 12/1983 |
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 1566201 A2 | 8/2005 |
| EP | 2397188 A1 | 12/2011 |
| EP | 2934308 B1 | 10/2015 |
| EP | 2934309 B1 | 10/2015 |
| EP | 3097180 B1 | 11/2016 |
| EP | 2759003 B1 | 8/2020 |
| EP | 3558457 A4 | 8/2020 |
| EP | 3700629 A1 | 9/2020 |
| EP | 3218829 B1 | 10/2020 |
| EP | 3229688 B1 | 10/2020 |
| EP | 3723857 A1 | 10/2020 |
| EP | 2887989 B1 | 2/2021 |
| EP | 3777689 A1 | 2/2021 |
| EP | 2938253 B1 | 3/2021 |
| EP | 3076864 B1 | 3/2021 |
| EP | 2802276 B1 | 4/2021 |
| EP | 2809221 B1 | 4/2021 |
| EP | 3801761 A1 | 4/2021 |
| EP | 3801762 A2 | 4/2021 |
| EP | 3801763 A1 | 4/2021 |
| EP | 2967369 B1 | 5/2021 |
| EP | 2967488 B1 | 6/2021 |
| EP | 3184048 B1 | 6/2021 |
| EP | 2967370 B1 | 9/2021 |
| EP | 3482390 B1 | 9/2021 |
| EP | 3870067 A1 | 9/2021 |

(56) References Cited

FOREIGN PATENT DOCUMENTS

| | | | |
|---|---|---|---|
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4041387 | A1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | A1 | 12/2022 |
| EP | 2950737 | B1 | 1/2023 |
| EP | 3057496 | B1 | 1/2023 |
| EP | 4114274 | A1 | 1/2023 |
| EP | 4117534 | A1 | 1/2023 |
| EP | 2869804 | B1 | 2/2023 |
| EP | 2938265 | B1 | 2/2023 |
| EP | 3024403 | B1 | 3/2023 |
| EP | 4138672 | A1 | 3/2023 |
| EP | 4151156 | A1 | 3/2023 |
| EP | 2938271 | B1 | 4/2023 |
| EP | 4161360 | A1 | 4/2023 |
| EP | 4179995 | A2 | 5/2023 |
| EP | 3171764 | B1 | 6/2023 |
| EP | 4201342 | A1 | 6/2023 |
| EP | 2931132 | B1 | 7/2023 |
| EP | 3229695 | B1 | 7/2023 |
| EP | 4209178 | A1 | 7/2023 |
| EP | 4209179 | A1 | 7/2023 |
| EP | 4226864 | A1 | 8/2023 |
| EP | 4230121 | A2 | 8/2023 |
| EP | 4230146 | A1 | 8/2023 |
| EP | 4233972 | A2 | 8/2023 |
| EP | 2866733 | B1 | 9/2023 |
| EP | 3870069 | B1 | 9/2023 |
| EP | 4247489 | A1 | 9/2023 |
| EP | 3484371 | B1 | 10/2023 |
| EP | 3658037 | B1 | 10/2023 |
| EP | 3685874 | B1 | 10/2023 |
| EP | 3870070 | B1 | 10/2023 |
| EP | 2938255 | B1 | 11/2023 |
| EP | 3229906 | B1 | 11/2023 |
| EP | 3764914 | B1 | 11/2023 |
| EP | 3903672 | B1 | 11/2023 |
| EP | 4272654 | A2 | 11/2023 |
| EP | 4275609 | A2 | 11/2023 |
| EP | 3316804 | B1 | 12/2023 |
| EP | 3519109 | B1 | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 4349283 | A1 | 4/2024 |
| EP | 3681419 | B1 | 5/2024 |
| EP | 4368118 | A2 | 5/2024 |
| EP | 2804525 | B1 | 6/2024 |
| EP | 4380667 | A2 | 6/2024 |
| EP | 4385428 | A1 | 6/2024 |
| EP | 4289415 | A4 | 1/2025 |
| EP | 4406484 | B1 | 1/2025 |
| EP | 3190958 | B1 | 2/2025 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| GB | 2099582 | A | 12/1982 |
| HK | 1245715 | B | 1/2021 |
| IL | 254768 | A | 5/2021 |
| IL | 261285 | B | 2/2022 |
| IN | 202117039853 | A | 12/2021 |
| IN | 387413 | B | 1/2022 |
| IN | 445766 | B | 8/2023 |
| JP | 60-80779 | A | 5/1985 |
| JP | 61-196718 | A | 8/1986 |
| JP | 02-215451 | A | 8/1990 |
| JP | H0422351 | A | 1/1992 |
| JP | 06-197907 | A | 7/1994 |
| JP | 07-504339 | A | 5/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |

(56) References Cited

FOREIGN PATENT DOCUMENTS

| | | |
|---|---|---|
| JP | 2022509401 A | 1/2022 |
| JP | 2022509453 A | 1/2022 |
| JP | 2022510217 A | 1/2022 |
| JP | 7019679 B2 | 2/2022 |
| JP | 7026118 B2 | 2/2022 |
| JP | 2022514272 A | 2/2022 |
| JP | 2022515488 A | 2/2022 |
| JP | 2022516078 A | 2/2022 |
| JP | 7053500 B2 | 4/2022 |
| JP | 2022526104 A | 5/2022 |
| JP | 2022527043 A | 5/2022 |
| JP | 2022095785 A | 6/2022 |
| JP | 7171645 B2 | 11/2022 |
| JP | 7171663 B2 | 11/2022 |
| JP | 7175640 B2 | 11/2022 |
| JP | 2022546288 A | 11/2022 |
| JP | 7187715 B2 | 12/2022 |
| JP | 2022551875 A | 12/2022 |
| JP | 2022552229 A | 12/2022 |
| JP | 7201819 B2 | 1/2023 |
| JP | 7232204 B2 | 3/2023 |
| JP | 7239466 B2 | 3/2023 |
| JP | 7265525 B2 | 4/2023 |
| JP | 2023071859 A | 5/2023 |
| JP | 7292448 B2 | 6/2023 |
| JP | 7299992 B2 | 6/2023 |
| JP | 2023085350 A | 6/2023 |
| JP | 7302936 B2 | 7/2023 |
| JP | 7304344 B2 | 7/2023 |
| JP | 7321162 B2 | 8/2023 |
| JP | 7325430 B2 | 8/2023 |
| JP | 7335367 B2 | 8/2023 |
| JP | 2023116673 A | 8/2023 |
| JP | 7340594 B2 | 9/2023 |
| JP | 7346293 B2 | 9/2023 |
| JP | 7351972 B2 | 9/2023 |
| JP | 7352561 B2 | 9/2023 |
| JP | 2023123676 A | 9/2023 |
| JP | 2023134811 A | 9/2023 |
| JP | 7358391 B2 | 10/2023 |
| JP | 7359765 B2 | 10/2023 |
| JP | 7370386 B2 | 10/2023 |
| JP | 2023162327 A | 11/2023 |
| JP | 2024010135 A | 1/2024 |
| JP | 2024020483 A | 2/2024 |
| JP | 7479288 B2 | 5/2024 |
| JP | 7479351 B2 | 5/2024 |
| JP | 7485383 B2 | 5/2024 |
| JP | 7530561 B2 | 8/2024 |
| JP | 7542708 B2 | 8/2024 |
| JP | 7612816 B2 | 1/2025 |
| JP | 2025013082 A | 1/2025 |
| JP | 7641600 B2 | 3/2025 |
| JP | 7643694 B2 | 3/2025 |
| JP | 2025031814 A | 3/2025 |
| KR | 102574559 B1 | 9/2023 |
| KR | 10276498281 | 2/2025 |
| KR | 20250019597 A | 2/2025 |
| WO | WO94/06355 A1 | 3/1994 |
| WO | WO02/32506 A1 | 4/2002 |
| WO | WO2005/018469 A1 | 3/2005 |
| WO | WO2008/051484 A2 | 5/2008 |
| WO | WO2011/040054 A1 | 7/2011 |
| WO | WO2011/092683 A1 | 8/2011 |
| WO | WO2011/154654 A2 | 12/2011 |
| WO | WO2014/008594 A1 | 1/2014 |
| WO | WO2014/071386 A1 | 5/2014 |
| WO | WO2015/000953 A1 | 1/2015 |
| WO | WO2015/031532 A1 | 3/2015 |
| WO | WO2015/153909 A2 | 10/2015 |
| WO | WO2018/149671 A1 | 8/2018 |
| WO | WO2019/081329 A1 | 5/2019 |
| WO | WO2019/122941 A1 | 6/2019 |
| WO | WO2020/074615 A1 | 4/2020 |
| WO | WO2020/087049 A1 | 4/2020 |
| WO | WO2020/217098 A2 | 10/2020 |
| WO | WO2020/237382 A1 | 12/2020 |
| WO | WO2020/245660 A1 | 12/2020 |
| WO | WO2021/014221 A1 | 1/2021 |
| WO | WO2021/032887 A1 | 2/2021 |
| WO | WO2021/069216 A1 | 4/2021 |
| WO | WO2021/069971 A1 | 4/2021 |
| WO | WO2021/089810 A1 | 5/2021 |
| WO | WO2021/105358 A1 | 6/2021 |
| WO | WO2021/115958 A1 | 6/2021 |
| WO | WO2021/116763 A1 | 6/2021 |
| WO | WO2021/122253 A1 | 6/2021 |
| WO | WO2021/123905 A2 | 6/2021 |
| WO | WO2021/123906 A1 | 6/2021 |
| WO | WO2021/140042 A1 | 7/2021 |
| WO | WO2021/142090 A1 | 7/2021 |
| WO | WO2021/170510 A1 | 9/2021 |
| WO | WO2021/175626 A1 | 9/2021 |
| WO | WO2021/176275 A1 | 9/2021 |
| WO | WO2021/178961 A1 | 9/2021 |
| WO | WO2021/180501 A1 | 9/2021 |
| WO | WO2021/180550 A1 | 9/2021 |
| WO | WO2021/213927 A1 | 10/2021 |
| WO | WO2021/249936 A1 | 12/2021 |
| WO | WO2021/258007 A1 | 12/2021 |
| WO | WO2022/013266 A1 | 1/2022 |
| WO | WO2022/040493 A1 | 2/2022 |
| WO | WO2022/047193 A8 | 3/2022 |
| WO | WO2022/056394 A1 | 3/2022 |
| WO | WO2022/069254 A1 | 4/2022 |
| WO | WO2022/069303 A2 | 4/2022 |
| WO | WO2022/069327 A2 | 4/2022 |
| WO | WO2022/078744 A1 | 4/2022 |
| WO | WO2022/097138 A1 | 5/2022 |
| WO | WO2022/106891 A1 | 5/2022 |
| WO | WO2022/152724 A1 | 7/2022 |
| WO | WO2022/152827 A1 | 7/2022 |
| WO | WO2022/152828 A1 | 7/2022 |
| WO | WO2022/228922 A1 | 11/2022 |
| WO | WO2022/238058 A1 | 11/2022 |
| WO | WO2022/238092 A1 | 11/2022 |
| WO | WO2022/238229 A1 | 11/2022 |
| WO | WO2022/238274 A1 | 11/2022 |
| WO | WO2022/238276 A1 | 11/2022 |
| WO | WO2022/238392 A1 | 11/2022 |
| WO | WO2022/247242 A1 | 12/2022 |
| WO | WO2022/258561 A1 | 12/2022 |
| WO | WO2022/260746 A1 | 12/2022 |
| WO | WO2022/260747 A1 | 12/2022 |
| WO | WO2023/274899 A1 | 1/2023 |
| WO | WO2023/275617 A2 | 1/2023 |
| WO | WO2023/275771 A1 | 1/2023 |
| WO | WO2023/012516 A2 | 2/2023 |
| WO | WO2023/036742 A1 | 3/2023 |
| WO | WO2023/052278 A1 | 4/2023 |
| WO | WO2023/084307 A1 | 5/2023 |
| WO | WO2023/104599 A1 | 6/2023 |
| WO | WO2023/104841 A1 | 6/2023 |
| WO | WO2023/110555 A1 | 6/2023 |
| WO | WO2023/110556 A1 | 6/2023 |
| WO | WO2023/110594 A1 | 6/2023 |
| WO | WO2023/110607 A1 | 6/2023 |
| WO | WO2023/117721 A1 | 6/2023 |
| WO | WO2023/117821 A1 | 6/2023 |
| WO | WO2023/117822 A1 | 6/2023 |
| WO | WO2023/118080 A1 | 6/2023 |
| WO | WO2023105288 A1 | 6/2023 |
| WO | WO2023105290 A1 | 6/2023 |
| WO | WO2023/131566 A1 | 7/2023 |
| WO | WO2023/131574 A1 | 7/2023 |
| WO | WO2023/135024 A1 | 7/2023 |
| WO | WO2023/141653 A2 | 7/2023 |
| WO | WO2023/152639 A1 | 8/2023 |
| WO | WO2023/169967 A1 | 9/2023 |
| WO | WO2023/180811 A2 | 9/2023 |
| WO | WO2023/218428 A1 | 11/2023 |
| WO | WO2023/230053 A1 | 11/2023 |
| WO | WO2023/230054 A1 | 11/2023 |
| WO | WO2024/009143 A1 | 1/2024 |

(56) References Cited

FOREIGN PATENT DOCUMENTS

| | | |
|---|---|---|
| WO | WO2024/016088 A1 | 1/2024 |
| WO | WO2024/040185 A2 | 2/2024 |
| WO | WO2024/047580 A1 | 3/2024 |
| WO | WO2024/092272 A1 | 5/2024 |
| WO | WO2024/120659 A1 | 6/2024 |
| WO | WO2024/125872 A1 | 6/2024 |
| WO | WO2024/130252 A1 | 6/2024 |
| WO | WO2024/144897 A1 | 7/2024 |
| WO | WO2025/038127 A1 | 2/2025 |
| WO | WO2025/059671 A1 | 3/2025 |

OTHER PUBLICATIONS

Concentric-Ring and Sector-Vortex Phased-Array Applicators for Ultrasound Hyperthermia (Year: 1986).*
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
Avago Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
BAK; Rapid prototyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderid=db3a304412b407950112b408e8o90004&fileid=db3a304412b407950112b40ac9a40688>pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.

Clasen et al.; MR-guided radiofrequency ablation of hepatocellular carcinoma: Long-term effectiveness; J Vasc Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Dovedi et al.; Acquired Resistance to Fractionated Radiotherapy Can Be Overcome by Concurrent PD-LI Blockade; Cancer Research; 74(19); pp. 5458-5468; Oct. 1, 2014.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue)1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle volume fraction on sound velocity and attenuation of EPDM composites; Ultrasonics, vol. 46, pp. 177-183, Feb. 2007.

(56) References Cited

OTHER PUBLICATIONS

Kim et al.; Development of a wearable robotic positioning system for noninvasive transcranial focused ultrasound stimulation. IEEE/ASME Transactions on Mechatronics; 21(5); pp. 2284-2293; Jun. 13, 2016.

Konofagou; Quo vadis elasticity imaging?; Ultrasonics; 42(1-9); pp. 331-336; Apr. 2004.

Krimholtz et al.; New equivalent circuits for elementary piezoelectric transducers; Electronics Letters, vol. 6, pp. 398-399, Jun. 1970.

Kruse et al.; Tissue characterization using magnetic resonance elastography: Preliminary results; Phys. Med. Biol; 45(6); pp. 1579-1590; Jun. 2000.

Lake et al.; Histotripsy: minimally invasive technology for prostatic tissue ablation in an in vivo canine model; Urology; 72(3); pp. 682-686; Sep. 2008.

Lauterborn et al.; Cavitation bubble dynamics studied by high speed photography and holography: part one; Ultrasonics; vol. 23; pp. 260-268; Nov. 1985.

Lensing et al.; Deep-vein thrombosis; The Lancet, vol. 353, pp. 479-485, Feb. 6, 1999.

Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).

Liu et al.; Real-time 2-D temperature imaging using ultrasound; IEEE Trans Biomed Eng; 57(1); pp. 12-16; Jan. 2010 (author manuscript, 16 pgs.).

Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.

Manes et al.; Design of a Simplified Delay System for Ultrasound Phased Array Imaging; Sonics and Ultrasonics, IEEE Transactions on, vol. 30, pp. 350-354, Nov. 1983.

Maréchal et al; Effect of Radial Displacement of Lens on Response of Focused Ultrasonic Transducer; Japanese Journal of Applied Physics, vol. 46, p. 3077-3085; May 15, 2007.

Maréchal et al; Lens-focused transducer modeling using an extended KLM model; Ultrasonics, vol. 46, pp. 155-167, May 2007.

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.

Maxwell et al.; Cavitation clouds created by shock scattering from bubbles during histotripsy; J. Acoust. Soc. Am.; 130(4); pp. 1888-1898; Oct. 2011.

Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).

Maxwell; Noninvasive thrombolysis using histotripsy pulsed ultrasound cavitation therapy; PhD Dissertation. University of Michigan, Ann Arbor, Michigan. Jun. 2012.

Maxwell et al.; In-vivo study of non-invasive thrombolysis by histotripsy in a porcine model; IEEE international Ultrasonics Symposium; IEEE; p. 220-223; Sep. 20, 2009.

Maxwell et al.; The role of compressional pressure in the formation of dense bubble clouds in histotripsy, 2009 IEEE International Ultrasonics Symposium; pp. 81-84, Sep. 20, 2009.

Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

Miller et al.; Real-time elastography-based monitoring of histotripsy tissue fractionation using color doppler; Ultrasonics Symposium (IUS); 2012 IEEE International; 8 pages; Oct. 7-10, 2012.

Nightingale et al.; Analysis of contrast in images generated with transient acoustic radiation force; Ultrasound Med Biol; 32(1); pp. 61-72; Jan. 2006.

Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.

Okada et al.; A case of hepatocellular carcinoma treated by MR-guided focused ultrasound ablation with respiratory gating; Magn Reson Med Sci; 5(3); pp. 167-171; Oct. 2006.

Palmeri et al.; Acoustic radiation force-based elasticity imaging methods; Interface Focus; 1; pp. 553-564; Aug. 2011.

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.

Parsons et al.; Pulsed cavitational ultrasound therapy for controlled tissue homogenization; Ultrasound in Med. & Biol.; vol. 32(1); pp. 115-129; Jan. 2006.

Pishchalnikov et al.; Cavitation Bubble Cluster Activity in the Breakage of Kidney Stones by Lithotripter Shock Waves; J Endourol.; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Qu et al.; Non-thermal histotripsy tumor ablation promotes abscopal immune responses that enhance cancer immunotherapy; Journal for immunotherapy of cancer; 8(1); Jan. 15, 2020.

Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.

Rosenschein et al.; Ultrasound Imaging-Guided Noninvasive Ultrasound Thrombolysis: Preclinical Results; Circulation; vol. 102; pp. 238-245, Jul. 11, 2000.

Rowland et al.; MRI study of hepatic tumours following high intensity focused ultrasound surgery; British Journal of Radiology; 70; pp. 144-153; Feb. 1997.

Roy et al.; A precise technique for the measurement of acoustic cavitation thresholds and some preliminary results; Journal of the Acoustical Society of America; vol. 78(5); pp. 1799-1805; Nov. 1985.

Sapareto et al.; Thermal dose determination in cancer therapy; Int J Radiat Oncol Biol Phys; 10(6); pp. 787-800; Apr. 1984.

Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

Sato et al.; Experimental Investigation of Phased Array Using Tapered Matching Layers. 2002 IEEE Ultrasound Symposium. vol. 2; pp. 1235-1238, Oct. 2002.

Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.

Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

(56) References Cited

OTHER PUBLICATIONS

Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).

Souchon et al.; Visualisation of HIFU lesions using elastography of the human prostate in vivo: Preliminary results; Ultrasound Med. Biol; 29(7); pp. 1007-1015; Jul. 2003.

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

Therapeutic Ultrasound Group. Non-invasive Ultrasonic Tissue Fraction for Treatment of Benign Disease and Cancer—"Histotripsy" University research [online]. Biomedical Engineering Department, University of Michigan. Jul. 2011[retrieved on Jan. 28, 2014] from: (http://web.archive.org/web/20110720091822/http://www.histotripsy.umich.edu/index.html> entiredocument) Jul. 2011.

TODA; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.; A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Wikipedia; Medical ultrasound; 15 pages; retrieved from the internet (https://en.wikipedia.org/w/index.php?title=Medical_utrasound&oldid=515340960) on Jan. 12, 2018.

Wu et al.; Mechanism and dynamics of hydrodynamic-acoustic cavitation (HAC); Ultrasonics sonochemistry; vol. 49., pp. 89-96; Dec. 1, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Gateau et al.; Transcranial ultrasonic therapy based on time reversal of acoustically induced cavitation bubble signature. IEEE Transactions on Biomedical Engineering: 57(1); pp. 134-144; Sep. 18, 2009.

Cannata et al.; U.S. Appl. No. 18/311,050 entitled "Histotripsy systems and methods," filed May 2, 2023.

Maxwell et al.; U.S. Appl. No. 18/329,459 entitled "Histotripsy for thrombolysis," filed Jun. 5, 2023.

Xu et al.; U.S. Appl. No. 18/478,342 entitled "Systems and methods for histotripsy immunosensitization," filed Sep. 29, 2023.

Duryea et al.; U.S. Appl. No. 18/497,856 entitled "Histotripsy systems and methods," filed Oct. 31, 2023.

Duryea et al.; U.S. Appl. No. 18/498,966 entitled "Histotripsy systems and methods," filed Oct. 31, 2023.

Cain et al.; U.S. Appl. No. 18/485,904 entitled "Histotripsy using very short ultrasound pulses," filed Oct. 12, 2023.

Xu et al.; U.S. Appl. No. 18/555,683 entitled "Design and fabrication of therapeutic ultrasound transducer with arbitrarily shaped, densely packing, removable modular elements," filed Oct. 16, 2023.

International Society for Magnetic Resonance in Medicine (ISMRM); No. 105; XP040714022;I Jul. 24, 2020.

Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.

Sukovich et al.; Real-time transcranial histotripsy treatment localization and mapping using acoustic cavitation emission feedback; IEEE transactions on ultrasonics, ferroelectrics, and frequency control; 67(6); pp. 1178-1791; Jan. 17, 2020.

Bader et al.; For whom the bubble grows: physical principles of bubble nucleation and dynamics in histotripsy ultrasound therapy; Ultrasound in medicine & biology; 45(5); pp. 1056-1080, May 1, 2019.

Xu et al.; U.S. Appl. No. 18/568,038 entitled "Minimally invasive histotripsy systems and methods," filed Dec. 7, 2023.

Cannata et al.; U.S. Appl. No. 18/594,843 entitled "Histotripsy systems and methods," filed Mar. 4, 2024.

Cannata et al.; U.S. Appl. No. 18/630,758 entitled "Histotripsy systems and methods," filed Apr. 9, 2024.

Cannata et al.; U.S. Appl. No. 18/642,529 entitled "Histotripsy systems and associated methods including user interfaces and workflows for treatment planning and therapy," filed Apr. 22, 2024.

Maxwell et al.; U.S. Appl. No. 18/737,731 entitled "Histotripsy for thrombolysis," filed Jun. 7, 2024.

Cannata et al.; U.S. Appl. No. 18/737,746 entitled "Histotripsy excitation sequences optimized for bubble cloud formation using shoock scattering," filed Jun. 7, 2024.

Stopek.; U.S. Appl. No. 18/761,937 entitled "Minimally invasive histotripsy systems and methods," filed Jul. 2, 2024.

Shaffer et al.; U.S. Appl. No. 18/832,708 entitled "Histotripsy systems and methods," filed Jul. 24, 2024.

Miller et al.; U.S. Appl. No. 18/924,812 entitled "Histotripsy systems and methods," filed Oct. 23, 2024.

Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.

Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.

* cited by examiner

HEAT MAP

EXPOSURE LEVELS

LESION & EXPOSURE LEVELS

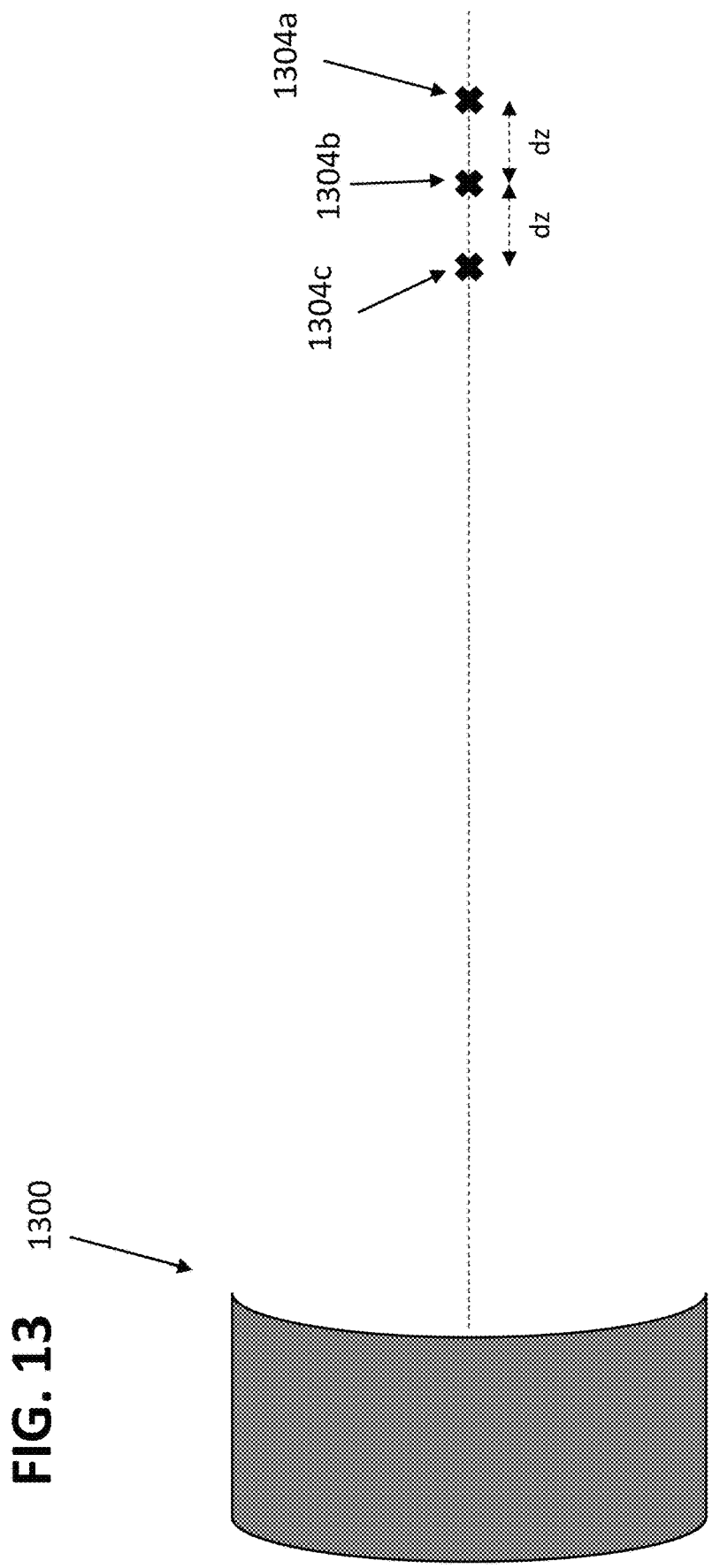

HISTOTRIPSY SYSTEMS AND METHODS

CROSS REFERENCE TO RELATED APPLICATIONS

This patent application is a continuation of U.S. application Ser. No. 18/497,856, filed Oct. 30, 2023, which claims priority to U.S. provisional patent application No. 63/381,401, titled "HISTOTRIPSY SYSTEMS AND METHODS" and filed on Oct. 28, 2022, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel high intensity therapeutic ultrasound (HITU) systems configured to produce acoustic cavitation, methods, devices and procedures for the minimally and non-invasive treatment of healthy, diseased and/or injured tissue. The acoustic cavitation systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, high-intensity focused ultrasound (HIFU) cryo or radiation, Histotripsy relies on the mechanical action of cavitation for tissue destruction and not on heat, cold or ionizing energy.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 13 is a schematic drawing showing the spacing between focal locations relative to a therapy transducer.

SUMMARY OF THE DISCLOSURE

Figure 1A:
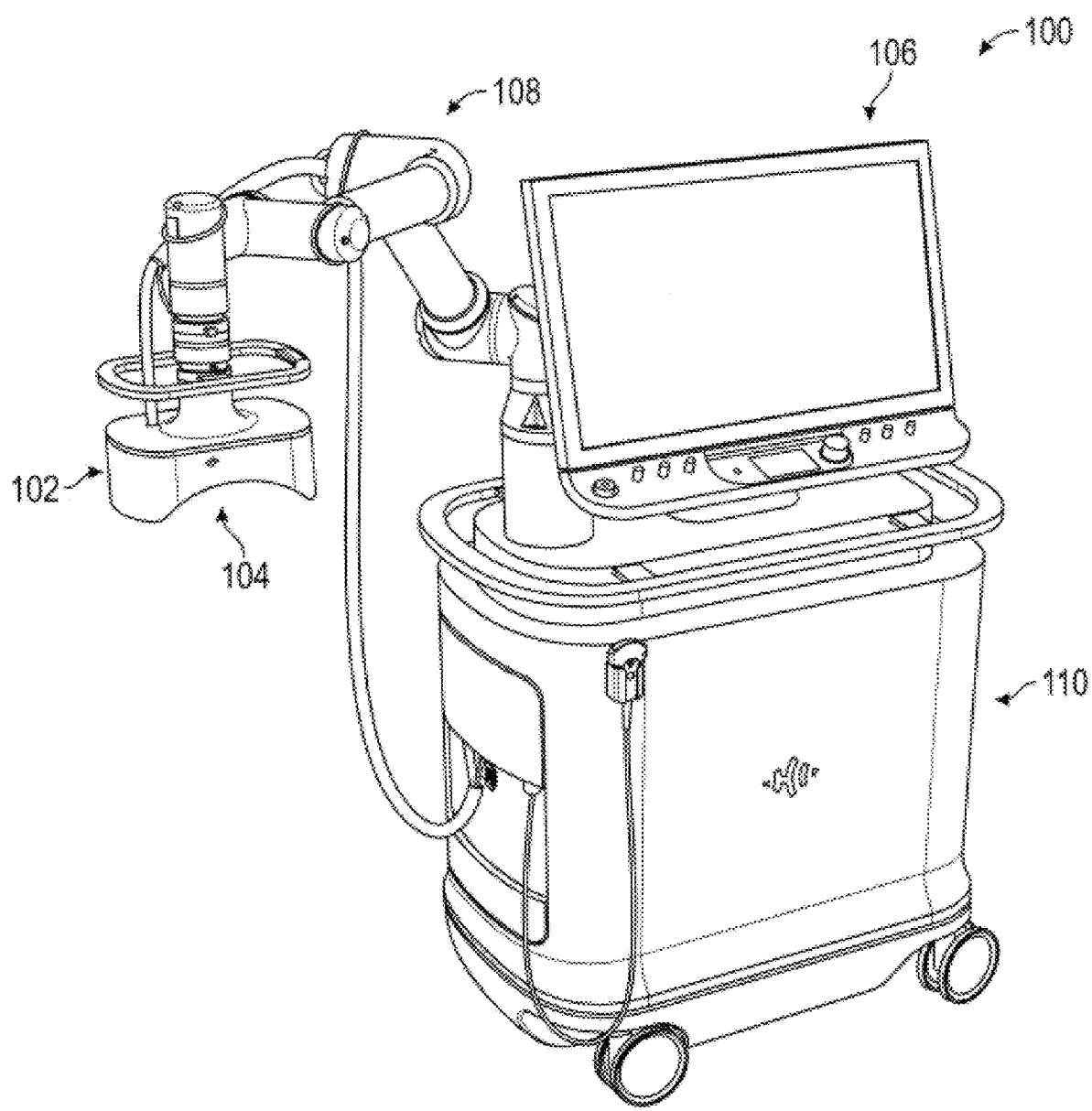
FIGS. 1A-1B illustrate an ultrasound imaging and therapy system.

A method of delivering histotripsy therapy to a target tissue is provided, comprising: receiving a digital treatment plan that includes a target tissue volume of a subject divided into a plurality of discrete treatment locations; mechanically positioning a focus of an ultrasound therapy transducer at a first focal location in a first discrete treatment location within the target tissue volume; delivering a first histotripsy pulse to the first focal location to produce a first cavitation bubble cloud at the first focal location; electronically beam-steering the focus of the ultrasound therapy transducer to a second focal location in the first discrete treatment location that overlaps with the first focal location; and delivering a second histotripsy pulse to the second focal location to produce a second bubble cloud at the second focal location and to at least partially re-excite the first cavitation bubble cloud at the first focal location.

In some aspects, the histotripsy pulse comprises a positive half-cycle followed by a peak negative half-cycle followed by a trailing positive half-cycle.

In some aspects, the trailing positive half-cycle has an amplitude lower than that of the leading positive half-cycle In one aspect, delivering the second histotripsy pulse to the second focal location further comprises delivering the second histotripsy pulse to the second focal location to produce the second bubble cloud at the second focal location during a life-cycle of the first bubble cloud.

In other aspects, delivering the second histotripsy pulse to the second focal location further comprises delivering the second histotripsy pulse to the second focal location to produce the second bubble cloud at the second focal location during a life-cycle of residual cavitation nuclei of the first bubble cloud.

In one aspect, electronically beam-steering the focus further comprises electronically beam-steering the focus in an axial direction with respect to the ultrasound therapy transducer.

In other aspects, electronically beam-steering the focus further comprises electronically beam-steering the focus in any lateral direction with respect to the ultrasound therapy transducer.

In some aspects, electronically beam-steering the focus further comprises electronically beam-steering the focus in a lateral and an axial direction with respect to the ultrasound therapy transducer.

In another aspect, the method includes repeating the electronic beam-steering and delivering steps for a third focal location that overlaps with the second focal location.

In some aspects, the method includes repeating the electronic beam-steering and delivering steps for a third focal location that overlaps with the first focal location.

In one aspect, after each delivering step, the method includes delivering at least one low amplitude waveform into the target tissue to spatially manipulate residual cavitation nuclei in the target tissue.

In other aspects, the method includes repeating the delivering and electronically beam-steering steps for the first and second focal locations until a desired dose is applied to the first discrete treatment location.

In some aspects, the method includes mechanically positioning the focus of the ultrasound therapy transducer at a first focal location in a second discrete treatment location within the target tissue volume after the desired dose has been applied to the first discrete treatment location.

In one aspect, the method includes mechanically positioning the focus further comprises mechanically positioning the focus with a robotic positioning system.

An ultrasound therapy system is provided, comprising; optionally a robotic positioning system; an ultrasound therapy transducer array connected to the robotic positioning system; a generator operatively coupled to the ultrasound therapy transducer array, the generator and ultrasound therapy transducer array being configured to deliver histotripsy pulses into a subject to generate a cavitation bubble cloud in the subject; at least one processor operatively coupled to the robotic positioning system and the generator, the at least one processor being configured to control the robotic positioning system and the generator to provide histotripsy therapy to the subject according to a treatment plan that includes a plurality of discrete treatment locations within a target tissue volume of the subject by: controlling the robotic positioning system to mechanically position a focus of the ultrasound therapy transducer array at a first focal location in a first discrete treatment location within the treatment plan; controlling the generator to deliver at least one histotripsy pulse with the ultrasound therapy transducer array to form a first cavitation bubble cloud at the first focal location; controlling the generator to electronically beam-steer the focus of the ultrasound therapy transducer to a second focal location in the first discrete treatment location that overlaps with the first focal location; and controlling the generator to deliver at least one histotripsy pulse to the second focal location to produce a second bubble cloud at the second focal location and to re-excite the first cavitation bubble cloud at the first focal location.

In some aspects, each of the histotripsy pulses comprises a positive half-cycle followed by a peak negative half-cycle followed by a trailing positive half-cycle, In one aspect, the trailing positive half-cycle has an amplitude lower than that of the leading positive half-cycle.

In one aspect, controlling the generator to deliver the at least one histotripsy pulse to the second focal location further comprises controlling the generator to deliver the at least one histotripsy pulse to the second focal location to produce the second bubble cloud at the second focal location during a life-cycle of the first bubble cloud.

In other aspects, controlling the generator to deliver the at least one histotripsy pulse to the second focal location further comprises controlling the generator to deliver the at least one histotripsy pulse to the second focal location to produce the second bubble cloud at the second focal location during a life-cycle of residual cavitation nuclei of the first bubble cloud.

In some aspects, controlling the generator to electronically beam-steer the focus further comprises controlling the generator to electronically beam-steer the focus in an axial direction with respect to the ultrasound therapy transducer array.

In some aspects, controlling the generator to electronically beam-steer the focus further comprises controlling the generator to electronically beam-steer the focus in any lateral direction with respect to the ultrasound therapy transducer array.

In some aspects, controlling the generator to electronically beam-steer the focus further comprises controlling the generator to electronically beam-steer the focus in a lateral and an axial direction with respect to the ultrasound therapy transducer array.

In one aspect, the system is configured to repeat controlling the generator to electronically beam-steer and controlling the generator to deliver at least one histotripsy pulse for a third focal location that overlaps with the second focal location.

In other aspects, the system is configured to repeat controlling the generator to electronically beam-steer and controlling the generator to deliver at least one histotripsy pulse for a third focal location that overlaps with the first focal location.

In one aspect, after controlling the generator to deliver at least one histotripsy pulse the system is configured to control the generator to deliver at least one low amplitude waveform into the target tissue to spatially manipulate residual cavitation nuclei in the target tissue.

In one aspect, the system is configured for repeating controlling the generator to electronically beam-steer and controlling the generator to deliver at least one histotripsy pulse for the first and second focal locations until a desired dose is applied to the first discrete treatment location.

In other aspects, the system is configured for controlling the robotic positioning system to mechanically position the focus of the ultrasound therapy transducer at a first focal location in a second discrete treatment location within the target tissue volume after the desired dose has been applied to the first discrete treatment location.

A method of delivering histotripsy therapy to a target tissue volume is provided, comprising the steps of: dividing the target tissue volume into a plurality of discrete treatment locations; determining a treatment plan that includes a pathway for providing therapy to each of the discrete treatment locations; positioning a focus of an ultrasound therapy transducer at a first focal location in a first discrete treatment location within the target tissue volume; delivering one or more histotripsy pulses to the first focal location to produce a first bubble cloud at the first focal location; electronically beam-steering the focus of the ultrasound therapy transducer to a second focal location in the first discrete treatment location that overlaps with the first focal location; delivering one or more histotripsy pulses to the second focal location to produce a second bubble cloud at the second focal location; and repeating the positioning and delivering steps for each of the plurality of discrete treatment locations according to the treatment plan and pathway.

In one aspect, each histotripsy pulse comprises a positive half-cycle followed by a peak negative half-cycle followed by a trailing positive half-cycle.

In other aspects, the trailing positive half-cycle has an amplitude lower than that of the leading positive half-cycle.

In some aspects, the method includes delivering the one or more histotripsy pulses to the second focal location further comprises delivering the one or more histotripsy pulses to the second focal location to produce the second bubble cloud at the second focal location during a life-cycle of the first bubble cloud.

In other aspects, the method includes delivering the one or more histotripsy pulses to the second focal location further comprises delivering the one or more histotripsy pulses to the second focal location to produce the second bubble cloud at the second focal location during a life-cycle of residual cavitation nuclei of the first bubble cloud.

In some aspects, electronically beam-steering the focus further comprises electronically beam-steering the focus in an axial direction with respect to the ultrasound therapy transducer.

In other aspects, electronically beam-steering the focus further comprises electronically beam-steering the focus in any lateral direction with respect to the ultrasound therapy transducer.

In one aspect, electronically beam-steering the focus further comprises electronically beam-steering the focus in a lateral and an axial direction with respect to the ultrasound therapy transducer.

In another aspect, the method includes repeating the electronic beam-steering and delivering steps for a third focal location that overlaps with the second focal location.

In some aspects, the method includes repeating the electronic beam-steering and delivering steps for a third focal location that overlaps with the first focal location.

In another aspect, after each delivering step the method includes delivering at least one low amplitude waveform into the target tissue to spatially manipulate residual cavitation nuclei in the target tissue.

In some aspects, the method includes repeating the delivering and electronically beam-steering steps for the first and second focal locations until a desired dose is applied to the first discrete treatment location.

In another aspect, the method includes mechanically positioning the focus of the ultrasound therapy transducer at a first focal location in a second discrete treatment location within the target tissue volume after the desired dose has been applied to the first discrete treatment location.

In some aspects, mechanically positioning the focus further comprises mechanically positioning the focus with a robotic positioning system.

A method of delivering histotripsy therapy to a target tissue volume is provided, comprising: delivering first his-totripsy therapy pulses to a first focal location to create a corresponding bubble cloud within a first focal zone; electronically beam-steering the focus a second focal location; and delivering second histotripsy therapy pulses to the second focal location to create a corresponding bubble cloud within a second focal zone that spatially overlaps with the first focal zone; wherein the second histotripsy pulses are timed to re-excite residual cavitation nuclei in the first focal zone to create an enhanced excitation volume comprising the first focal zone and second focal zone.

In some aspects, the histotripsy pulse comprises a positive half-cycle followed by a peak negative half-cycle followed by a trailing positive half-cycle.

In other aspects, the trailing positive half-cycle has an amplitude lower than that of the leading positive half-cycle.

In some aspects, delivering the second histotripsy pulse to the second focal location further comprises delivering the second histotripsy pulse to the second focal location to produce the second bubble cloud at the second focal location during a life-cycle of the first bubble cloud.

In another aspect, delivering the second histotripsy pulse to the second focal location further comprises delivering the second histotripsy pulse to the second focal location to produce the second bubble cloud at the second focal location during a life-cycle of residual cavitation nuclei of the first bubble cloud.

In some aspects, electronically beam-steering the focus further comprises electronically beam-steering the focus in an axial direction with respect to the ultrasound therapy transducer.

In one aspect, electronically beam-steering the focus further comprises electronically beam-steering the focus in any lateral direction with respect to the ultrasound therapy transducer.

In another aspect, electronically beam-steering the focus further comprises electronically beam-steering the focus in a lateral and an axial direction with respect to the ultrasound therapy transducer.

In some aspects, the method includes repeating the electronic beam-steering and delivering steps for a third focal location that overlaps with the second focal location.

In other aspects, the method includes repeating the electronic beam-steering and delivering steps for a third focal location that overlaps with the first focal location.

In one aspect, after each delivering step, the method includes delivering at least one low amplitude waveform into the target tissue to spatially manipulate residual cavitation nuclei in the target tissue.

In some aspects, the method includes repeating the delivering and electronically beam-steering steps for the first and second focal locations until a desired dose is applied to the first discrete treatment location.

In other aspects, the method includes mechanically positioning the focus of the ultrasound therapy transducer at a first focal location in a second discrete treatment location within the target tissue volume after the desired dose has been applied to the first discrete treatment location.

In some aspects, mechanically positioning the focus further comprises mechanically positioning the focus with a robotic positioning system.

A method of producing an enhanced excitation volume with histotripsy energy is provided, comprising positioning a focus of an ultrasound therapy transducer at a first focal location in a first discrete treatment location within a target tissue volume, the first focal location being positioned along a central axis of the ultrasound therapy transducer, delivering a first histotripsy pulse to the first focal location to produce a first cavitation bubble cloud at the first focal location, electronically beam-steering the focus of the ultrasound therapy transducer to a second focal location in the first discrete treatment location that is at least partially outside of the central axis, delivering a second histotripsy pulse to the second focal location to produce a second bubble cloud at the second focal location, electronically beam-steering the focus of the ultrasound therapy transducer to a focal location at least partially inside the central axis; and delivering a third histotripsy pulse to the focal location to produce a third bubble cloud at the focal location.

In some aspects, a natural focus of the ultrasound therapy transducer array is located along the central axis.

In other aspects, the first focal location comprises the natural focus.

In some aspects, the second focal location partially overlaps with the central axis.

In other aspects, the focal location comprises the first focal location.

In additional aspects, the focal location comprises a third focal location.

In some aspects, electronically beam-steering to the second focal location comprises steering laterally.

In other aspects, electronically beam-steering to the second focal location comprises steering laterally and axially.

An ultrasound therapy system is provided, comprising: a robotic positioning system; an ultrasound therapy transducer array connected to the robotic positioning system; a generator operatively coupled to the ultrasound therapy transducer array, the generator and ultrasound therapy transducer array being configured to deliver histotripsy pulses into a subject to generate a cavitation bubble cloud in the subject; at least one processor operatively coupled to the robotic positioning system and the generator, the at least one processor being configured to control the robotic positioning system and the generator to provide histotripsy therapy to the subject according to a treatment plan that includes a plurality of discrete treatment locations within a target tissue volume of the subject by: controlling the robotic positioning system to mechanically position a focus of the ultrasound therapy transducer array at a first focal location in a first discrete treatment location within the treatment plan, the first focal location being positioned along a central axis of the ultrasound therapy transducer array; controlling the generator to deliver at least one histotripsy pulse with the ultrasound therapy transducer array to form a first cavitation bubble cloud at the first focal location; controlling the generator to electronically beam-steer the focus of the ultrasound therapy transducer to a second focal location in the first discrete treatment location that is at least partially outside the central axis; controlling the generator to deliver at least one histotripsy pulse to the second focal location to produce a second bubble cloud at the second focal location; controlling the generator to electronically beam-steer the focus of the ultrasound therapy transducer to a focal location in the first discrete treatment location that is at least partially inside the central axis; and controlling the generator to deliver at least one histotripsy pulse to the focal location to produce a third bubble cloud at the focal location.

In some aspects, a natural focus of the ultrasound therapy transducer array is located along the central axis.

In other aspects, the first focal location comprises the natural focus.

In some aspects, the second focal location partially overlaps with the central axis.

In other aspects, the focal location comprises the first focal location.

In some aspects, the focal location comprises a third focal location.

In other aspects, the system is configured for controlling the generator to electronically beam-steer to the second focal location comprises steering laterally.

In other aspects, the system is configured for controlling the generator to electronically beam-steer to the second focal location comprises steering laterally and axially.

An ultrasound therapy system is provided, comprising: an ultrasound therapy transducer array; a generator operatively coupled to the ultrasound therapy transducer array, the generator and ultrasound therapy transducer array being configured to deliver histotripsy pulses into a subject to generate a cavitation bubble cloud in the subject; at least one processor operatively coupled to the generator, the at least one processor being configured to control the generator to provide histotripsy therapy to the subject according to a treatment plan that includes a plurality of discrete treatment locations within a target tissue volume of the subject by: controlling the generator to deliver at least one histotripsy pulse with the ultrasound therapy transducer array to form a first cavitation bubble cloud at a first focal location in a first discrete treatment location within the treatment plan; controlling the generator to electronically beam-steer the focus of the ultrasound therapy transducer to a second focal location in the first discrete treatment location that overlaps with the first focal location; and controlling the generator to deliver at least one histotripsy pulse to the second focal location to produce a second bubble cloud at the second focal location and to re-excite the first cavitation bubble cloud at the first focal location.

An ultrasound therapy system is provided, comprising: an ultrasound therapy transducer array; a generator operatively coupled to the ultrasound therapy transducer array, the generator and ultrasound therapy transducer array being configured to deliver histotripsy pulses into a subject to generate a cavitation bubble cloud in the subject; at least one processor operatively coupled to the generator, the at least one processor being configured to control the generator to provide histotripsy therapy to the subject according to a treatment plan that includes a plurality of discrete treatment locations within a target tissue volume of the subject by: controlling the generator to deliver at least one histotripsy pulse with the ultrasound therapy transducer array to form a first cavitation bubble cloud at a first focal location in a first discrete treatment location within the treatment plan, the first focal location being positioned along a central axis of the ultrasound therapy transducer array; controlling the generator to electronically beam-steer the focus of the ultrasound therapy transducer to a second focal location in the first discrete treatment location that is at least partially outside the central axis; controlling the generator to deliver at least one histotripsy pulse to the second focal location to produce a second bubble cloud at the second focal location; controlling the generator to electronically beam-steer the focus of the ultrasound therapy transducer to a focal location in the first discrete treatment location that is at least partially inside the central axis; and controlling the generator to deliver at least one histotripsy pulse to the focal location to produce a third bubble cloud at the focal location.

DETAILED DESCRIPTION

The system, methods and devices of the disclosure may be used for open surgical, minimally invasive surgical (laparoscopic and percutaneous), robotic surgical (integrated into a robotically-enabled medical system), endoscopic or completely transdermal extracorporeal non-invasive acoustic cavitation for the treatment of healthy, diseased and/or injured tissue including but not limited to tissue destruction, cutting, skeletonizing and ablation. Furthermore, due to tissue selective properties, histotripsy may be used to create a cytoskeleton that allows for subsequent tissue regeneration either de novo or through the application of stem cells and other adjuvants. Finally, histotripsy can be used to cause the release of delivered agents such as chemotherapy and immunotherapy by locally causing the release of these agents by the application of acoustic energy to the targets. As will be described below, the acoustic cavitation system may include various sub-systems, including a Cart, Therapy, Integrated Imaging, Robotics, Coupling and Software. The system also may comprise various Other Components, Ancillaries and Accessories, including but not limited to computers, cables and connectors, networking devices, power supplies, displays, drawers/storage, doors, wheels, and various simulation and training tools, etc. All systems, methods and means creating/controlling/delivering histotripsy are considered to be a part of this disclosure, including new related inventions disclosed herein.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown.

Figure 1B:
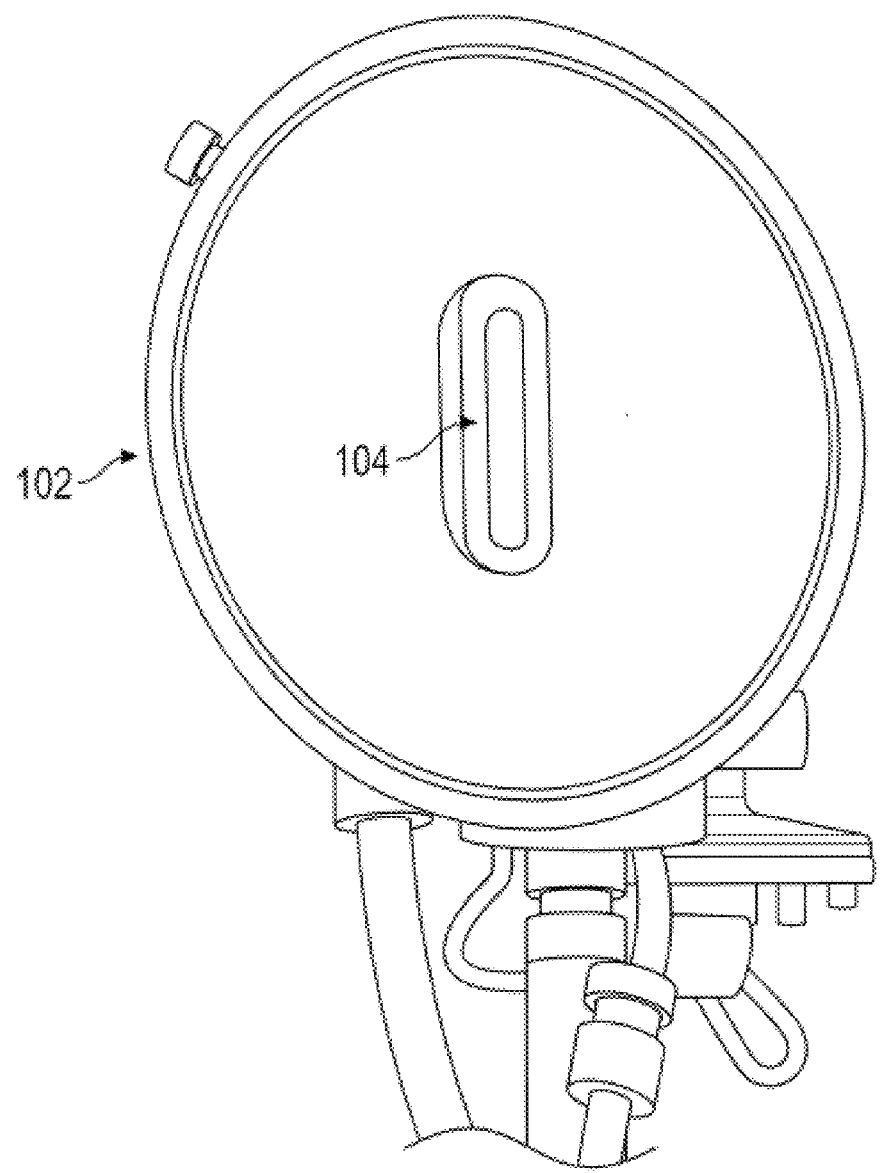

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer. The system also allows for multiple imaging transducers to be located within the therapy transducer to provide multiple views of the target tissue simultaneously and to integrate these images into a single 3-D image.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

As described above, the histotripsy system may include integrated imaging. However, in other embodiments, the histotripsy system can be configured to interface with separate imaging systems, such as C-arm, fluoroscope, cone beam CT, MRI, etc., to provide real-time imaging during histotripsy therapy. In some embodiments, the histotripsy system can be sized and configured to fit within a C-arm, fluoroscope, cone beam CT, MRI, etc.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment for open surgical or laparoscopic surgical and endoscopic application, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/mechanical interoperability (e.g., compatible within cone beam CT work-space for collecting imaging data pre, peri and/or post histotripsy) and to provide access to and display of patient medical data including but not limited to laboratory and historical medical record data.

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/ fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat cold or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses typically with a 1-2 cycles of high amplitude negative/tensile phase pressure exceeding the intrinsic threshold to generate cavitation in the medium (e.g., ~24-28 MPa for water-based soft tissue), 2) Shock-Scattering Histotripsy: Delivers typically pulses 1-20 cycles in duration. The shockwave (positive/ compressive phase) scattered from an initial individual microbubble generated forms inverted shockwave, which constructively interfere with the incoming negative/tensile phase to form high amplitude negative/rarefactional phase exceeding the intrinsic threshold. In this way, a cluster of cavitation microbubbles is generated. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed entirely or completely non-invasively by acoustically coupling a focused ultrasound transducer over the skin of a patient and transmitting acoustic pulses transcutaneously through overlying (and intervening) tissue to the focal zone (treatment zone and site). The application of histotripsy is not limited to a transdermal approach but can be applied through any means that allows contact of the transducer with tissue including open surgical laparoscopic surgical, percutaneous and robotically mediated surgical procedures. It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

Figure 3:
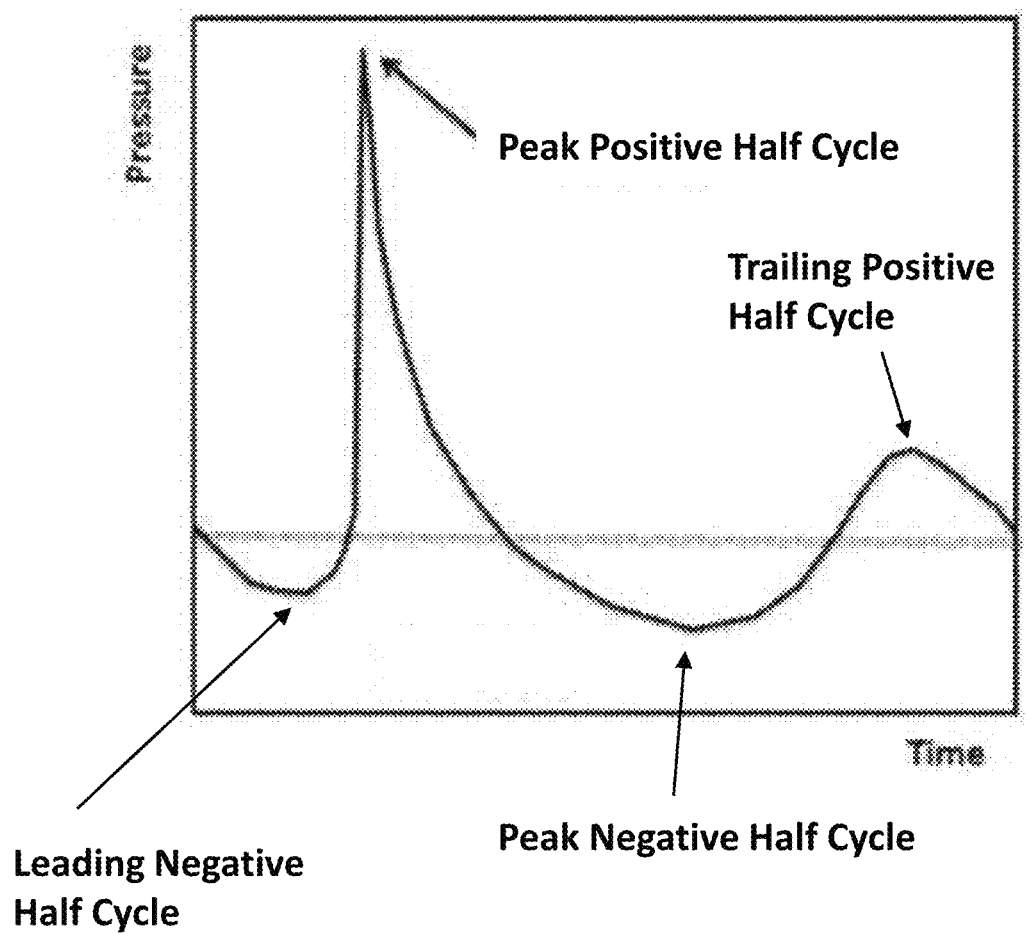
FIG. 3 is one example of an ultrasound pulse for generating histotripsy via a shock scattering mechanism.

FIG. 3 illustrates an ultrasound pulse that can be used for shock scattering histotripsy. As shown the ultrasound pulse can include a leading negative half cycle, a peak positive half cycle, a peak negative half cycle, and a trailing positive half cycle (with the pulse traveling from right to left on the page). As shown, the trailing positive half cycle has a lower amplitude than the peak positive half cycle. This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface if the amplitude of those cycles is sufficient, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When the amplitude(s) of positive half cycle(s) of each pulse are limited, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P-level for a region of interest (ROI), while the high-frequency pulse, which provides more precision, can pin-point a targeted location within the ROI and raise the peak negative pressure P-above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Challenges of Residual/Remnant Cavitation Nuclei

The concept of residual/remnant cavitation nuclei is known. It relates to the phenomenon that after a bubble cloud is generated and rapidly collapses within a medium (e.g., tissue), bubbles may remain sparsely distributed throughout the medium where prior histotripsy therapy has been applied. In some situations, the residual cavitation nuclei can affect histotripsy treatment and can create undesirable local environments that can challenge the ability to deliver histotripsy, effectively. This includes their ability to seed cavitation by subsequent therapy pulses, influencing the spatial distribution of subsequent bubble clouds such that cavitation occurs at prior treated locations (i.e., cavitation memory effect), while other and/or adjacent sites may experience reduced bubble cloud exposure or undertreatment. In some scenarios and conditions, remnant nuclei may result in bubble clouds forming preferentially where the remnant nuclei are located and at a distance from the prescribed focal location, resulting in less uniform treatment and/or distribution of treatment through the larger planned volume. Furthermore, and potentially more problematic in some cases, remnant nuclei can cause shielding/attenuation of subsequent pulses if they exist along the acoustic propagation path such that they can attenuate the incident therapy waveforms and reduce the energy delivered to tissue. In some examples, they may partially or fully block therapy.

Bubble Cloud Enhancement with Rapid Steering Between Overlapping Focal Zones

As described above, histotripsy therapy bubble clouds can be generated in a number of ways, including methods based on shock scattering and intrinsic threshold pulses. These sequences may include, but are not limited to, various types of pulses, including therapy, bubble manipulation pulses, etc. In some cases, bubble manipulation pulses may be used to modify the focal and treatment zone in effort to move or manipulate residual bubbles/nuclei remaining from prior pulses, which may adversely affect histotripsy treatments (e.g., act as blockers to subsequent histotripsy pulses).

This disclosure provides electronic beam-steering strategies configured to modify a single focal location environment to overcome the blockage, attenuation, and cavitation memory effect. This disclosure further provides additional systems, methods, and techniques to advantageously use adjacent residual cavitation nuclei to produce enhanced or enlarged cavitation bubble clouds in a highly controlled manner through the use of specifically designed computer-controlled hardware/software systems.

Provided herein are novel systems and methods for forming "enhanced excitation volumes" by enhancing, enlarging, and/or shaping a defined histotripsy "excitation volume", leveraging unique approaches to re-excite remnant nuclei to create a larger bubble cloud than would be possible without remnant nuclei re-excitation. For purposes of this disclosure, an "excitation volume" can comprise a volume within which a cavitation bubble cloud generated by a single, discrete focal location with an ultrasound therapy transducer array is expected to be formed. An "enhanced excitation volume" can comprise an enhanced or enlarged volume within which a cavitation bubble cloud generated by overlapping focal locations with electronic beam-steering of the ultrasound therapy transducer array between the overlapping focal locations is expected to be formed. As described herein, the pulse sequences and electronic beam-steering for enhanced excitation volumes can be chosen to advantageously exploit residual cavitation nuclei to enhance the volume of cavitation formed in a highly controlled manner. The systems and methods that enable this enhanced excitation volume may generally include 1) initiation of a bubble cloud at a first focal location (e.g., a natural focus of the therapy transducer array) and creation of a corresponding volume referred to as the "focal zone", 2) electronically beam-steering (e.g., phased array beam-steering) the focus to one or more additional focal locations in 2D (two-dimensional) or 3D (three-dimensional) space for creation of corresponding focal zones, 3) wherein the corresponding focal zone(s) are at least partially overlapping (with the first/prior focal zone volume(s)) and temporally and spatially positioned where pressures are within a threshold or range of the peak-pressure of the prior focal location/zone, 4) to re-excite remaining remnant nuclei (in the overlapping volume), 5) which together create the overall enhanced excitation volume or "larger bubble cloud" as shown in at least FIGS. 5B and 5C.

The above-described enhanced excitation volumes may be created in unlimited permutations, based on the selection of, but not limited to, the spatial and temporal parameters for creating these 3D excitation volumes. They may be comprised of varied shape and size by in part modifying the position of the steered focal locations in 3D space (and corresponding focal zones), the specific range and spacing of overlap of focal zones, beam profile overlap, maximum distance from the first focal location to the most distant focal location, sequencing, timing and/or phasing of therapy and/or bubble manipulation pulses including any pauses or wait periods, and/or the number of pulses per focal location and total number of pulses applied to the defined 3D excitation volume to continuously grow and/or fill in the excitation volume.

Further, in some embodiments, the design of the steering direction may be selected to allow the rapid steering and re-excitement of remnant nuclei, but to also minimize the need to steer directly distal to a focal location that was targeted immediately prior to aid in minimizing shielding or blocking effects not conducive to re-exciting the desired effect for creating larger excitation volumes As will be described later, the order of the steered locations can be of importance in minimizing the shielding or blocking effects not conducive to the invention of the present disclosure.

Spatial and Temporal Considerations

The enhanced excitation volumes described above may be designed, configured, and optimized based on various spatial and temporal considerations of 1) the spacing of the selected focal locations/zones so that the focal zone of a subsequent pulse overlaps with the focal zone of the/a previous pulse and 2) the timing of the subsequent pulse within a time span sufficient to re-excite residual nuclei present in the overlapping zone from one or more previous pulses.

The selection of spacing parameters may include selecting both the distance between adjacent focal locations, as well as the distance (range) between the most extreme focal locations. In some embodiments, there may be a plurality of focal location positions at uniformly and/or non-uniformly spaced coordinates (x, y, z), which may be selected/defined based on desired target excitation volume size (e.g., specific spacing values may result in varied per pulse bubble cloud area). The selection of these parameters may also be based on the specific histotripsy sequence, acoustic field properties and corresponding bubble cloud size. In some examples, the distance between steered focal locations may be based on the wavelength of the therapy pulses. In particular, the beam profile can be proportional to the wavelength of the ultrasound signal. In some implementations, the longer the wavelength of the ultrasound signal, the larger the beam profile. Similarly, the shorter the wavelength of the ultrasound signal, the smaller the beam profile. Furthermore, the beam profile in each axis (x, y, z) is also affected by the specific geometry of the therapy transducer. For example, transducers with f-numbers between 0.5 and 1 may result in pulses that generate "elongate" bubble clouds that have longer z dimensions than dimensions in x or y. Following this same principle, this may allow for the ability to electronically steer to a greater distance in the z direction than in x and y.

In terms of additional temporal aspects, the timing of electronic steering to adjacent or distant focal locations (and creation of overlapping focal zones), may use similar or varied pulse repetition frequency (PRF) and steering periods, and may be selected based on desired dose delivered. In one example, an enhanced excitation volume is created using one representative histotripsy pulse delivered to a first focal location at a selected PRF, and a following pulse is electronically beam-steered and delivered to a subsequent (or second) focal location that overlaps with the first focal location, wherein the steering period (amount of time from one electronic steering event to the next) is equivalent to the therapy PRF (amount of time from one therapy pulse to the next). This may be repeated until the total desired number of therapy pulses are delivered to the enhanced excitation volume. In other examples, based on the number and position of steered focal locations, some steered locations may have the same or different pulse(s), steering period or PRF, and/or other therapy parameters. For example, the electronic steering period may be shorter (faster) than the PRF. The systems described herein may also have embedded logic and/or algorithms to account and/or adjust for the spatial/temporal relationships.

Volumes may be created based on the selection of spacing distances, various shapes, and morphologies of excitation volumes. These may include continuous or discontinuous volumes and the selection of these parameters may be based on application (e.g., complete tumor destruction versus gross tissue debulking, etc.). As a representative example, some excitation volumes may be ellipsoidal in shape, whereas others may be more bulb-like. Other shapes and geometries of excitation volumes are envisioned and within the scope of this disclosure.

In some embodiments, these may be created by using rapid axial beam-steering (z axis) over short distances between focal locations (<5 mm) of overlapping focal zones to aid in creating a longer continuous enhanced excitation volume but using approximately the same number of pulses for a single corresponding natural focus (only) bubble cloud. In some embodiments, lateral beam-steering (x-y axis) overlapping focal locations may be used. In other embodiments, a combination of axial and lateral electronic beam-steering between focal locations (and overlapping focal locations) may be used to create more spherical enhanced excitation volumes, in part to enable more efficient/easier packing of such volumes into a larger grid pattern of planned treatment volume. In some examples, the distribution of focal points within an electronic steering embodiment can be adjusted to alter an aspect ratio of the ellipsoidal cloud specific to best fit desired treatment patterns and plan geometries.

Planned Treatment Volumes Based on Patterned/Packed "Enhanced Excitation Volumes"

A plurality of enhanced excitation volumes (or larger bubble clouds) may also be arranged and packed into subsequent larger structures comprised of defined 3D patterns and shapes, of which may be used to create a defined planned treatment volume. For example, if the target tissue to be treated is a tumor, then the treatment volume can encompass the tumor (and any desired margins) and be filled with a plurality of enhanced excitation volumes. The plurality of enhanced excitation volumes may comprise one or more specific shapes or sizes (based on spatial selection of focal locations and how pulses are applied to those positions). The system and control software delivering therapy may also comprise logic to populate a desired and/or user selected planned treatment volume with enhanced excitation volumes using packing rules for the placement, position and numbers required to fill that desired volume/shape.

The further arrangement and packing of the enhanced excitation volumes may include the selection of their axial and radial spacing, and degree of overlap. Planned treatment volumes may comprise the packing of one iteration of an enhanced excitation volume or more than one variation of them. For example, larger enhanced excitation volumes may be packed more centrally within a planned treatment volume, with smaller excitation volumes positioned along the perimeter of the planned treatment volume. Rules and logic including overlapping of focal zones and temporal and distance spacing apply to both of the above examples and in other implementations discussed herein. In an analogous example, varied shapes may be used to pack planned treatment volumes as well. In this use case, the use of more eccentric ellipsoidal shapes may be positioned more centrally, with surrounding/adjacent enhanced treatment volumes being more spherical in shape to better enable packing the outer perimeter of a treatment volume (and plan).

In particular, the enhanced excitation volumes described are generally larger than an excitation volume formed by a single, discreet focal zone volume, such as an excitation volume formed at the natural focus of the therapy transducer array. Therefore, fewer enhanced excitation volumes are required to pack a given treatment volume, such as a 3 cm sphere, compared to the number of discreet excitation volumes that would be required to pack the same volume if the enhanced excitation volume techniques were not used. In some embodiments, for a given treatment plan, a specified number of pulses are calculated for each excitation volume or enhanced excitation volume comprising the treatment volume to achieve complete treatment of the treatment plan while managing the thermal dose delivered to the patient. The same number of pulses are employed for either discreet focal zones (excitation volumes) or enhanced excitation volumes. Because fewer enhanced excitation volumes are required to populate the planned treatment volume, faster treatment times are enabled with using enhanced excitation volumes.

Figure 4A:
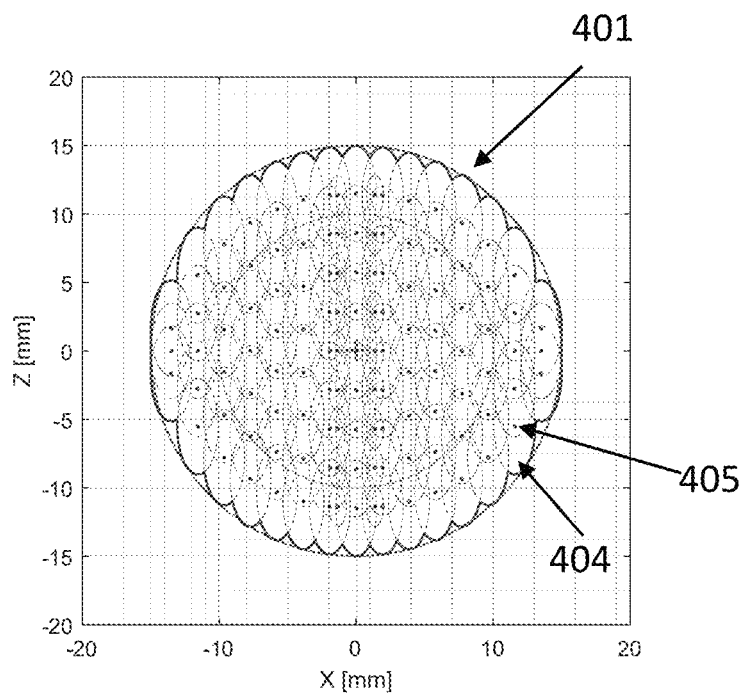
FIGS. 4A-4B illustrate packing techniques for treating a target tissue volume.
Figure 4B:
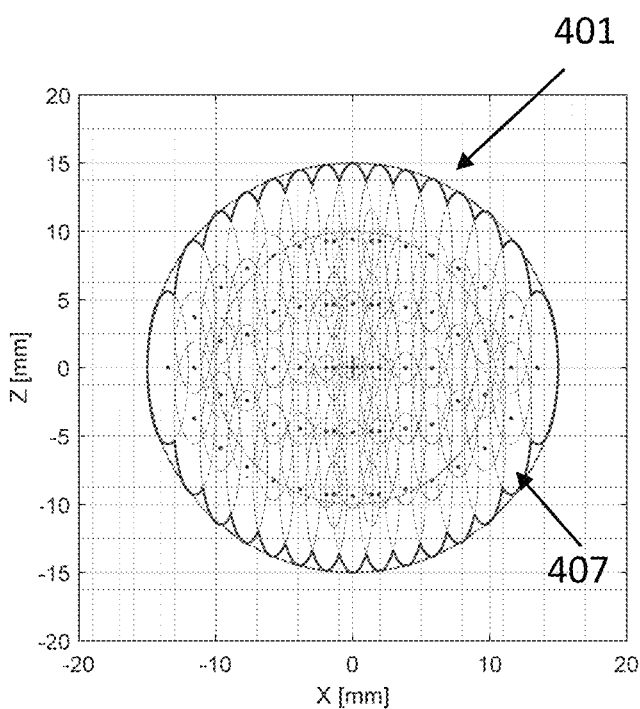

FIGS. 4A-4B show a comparison of packing a treatment volume with a plurality of excitation volumes vs. enhanced excitation volumes. FIGS. 4A-4B show a cross-sectional view of the treatment volumes in the z-x plane of the therapy transducer array. In this example, the therapy transducer array is positioned at the top of the page and directs treatment along the z-axis towards the bottom of the page.

FIG. 4A shows a treatment volume 401 packed with a plurality of excitation volumes 404. In this implementation, the excitation volumes are each discrete cavitation bubble cloud locations within the treatment volume, wherein each excitation volume is formed at the natural focus 405 of the therapy transducer array. To navigate through the treatment volume of FIG. 4A, the histotripsy system can use mechanical movement of the ultrasound therapy transducer array between excitation volumes as controlled by the robotic positioning system (e.g., mechanically moving the transducer array to the location for a given excitation volume), followed by delivering histotripsy therapy to generate the bubble cloud/excitation volume. This process can then be repeated for the remainder of the treatment volume by mechanically moving the transducer array to the next location for the next excitation volume, and so forth.

In contrast, FIG. 4B shows a treatment volume 401 packed with a plurality of enhanced excitation volumes 407. In this implementation, the enhanced excitation volumes are formed by rapidly electronically beam-steering the ultrasound therapy transducer array to a plurality of overlapping focal locations within the enhanced excitation volume to form an enhanced or larger bubble cloud by re-exciting residual cavitation nuclei within the enhanced excitation volume. As shown in FIG. 4B, the enhanced excitation volumes 407 are larger than the excitation volumes 403 of FIG. 4A. This allows for packing of the treatment volume 401 with a smaller number of enhanced excitation volumes 407, compared to the number of excitation volumes 404 required to pack the volume of FIG. 4A. To navigate through the treatment volume of FIG. 4B, the histotripsy system can use mechanical movement of the ultrasound therapy transducer array between enhanced excitation volumes as controlled by the robotic positioning system (e.g., mechanically moving the transducer array to a given enhanced excitation volume, and then electronically beam-steering the ultrasound transducer array within the enhanced excitation volume and delivering histotripsy therapy to generate the enhance bubble cloud/excitation volume. This process can then be repeated for the remainder of the treatment volume by mechanically moving the transducer array to the next enhanced excitation volume, electronically beam-steering the transducer and delivering histotripsy to form subsequent enhanced excitation volumes, and so forth.

In one specific implementation, an excitation volume formed at a natural focus of the ultrasound therapy transducer array, without rapid electronic beam-steering, can have volume dimensions of approximately 3 mm×3 mm×7 mm. In contrast, an enhanced excitation volume formed by rapid electronic beam-steering of the ultrasound transducer array can have volume dimensions of approximately 3 mm×3 mm×11 mm. With a treatment volume size of a 3 cm sphere in FIG. 4A, packing of the treatment volume with the natural focus excitation volumes requires approximately 1049 excitation volumes. However, implementing the enhanced excitation volumes, with the larger volume size, requires only 605 enhanced excitation volumes to pack the same 3 cm treatment volume sphere. It can therefore be seen that the enhanced excitation volumes of FIG. 4B require fewer volumes to pack the same sized treatment volume, which therefore increases the efficiency of treatment and reduces treatment times.

Additionally, some permutations of parameters selected for the design of enhanced excitation volumes may preferentially assist in breaking through the physiomechanical interfaces of adjacent focal zones (e.g., between natural focus and subsequent beam-steered location(s)), and/or of adjacent excitation volumes (additional discrete positions of volumes placed adjacently as part of a larger 3D planned treatment volume).

During therapy, the histotripsy therapy transducer and robotic positioning system can then be configured to automatically traverse a focus of the therapy transducer sequentially through each of the discrete therapy locations of the planned treatment volume. This traversal can be, for example, mechanical movement of the histotripsy therapy transducer by physically changing a position/orientation of the histotripsy therapy transducer with the robotic positioning system.

Implementation of Enhanced Excitation Volumes

Figure 5A:
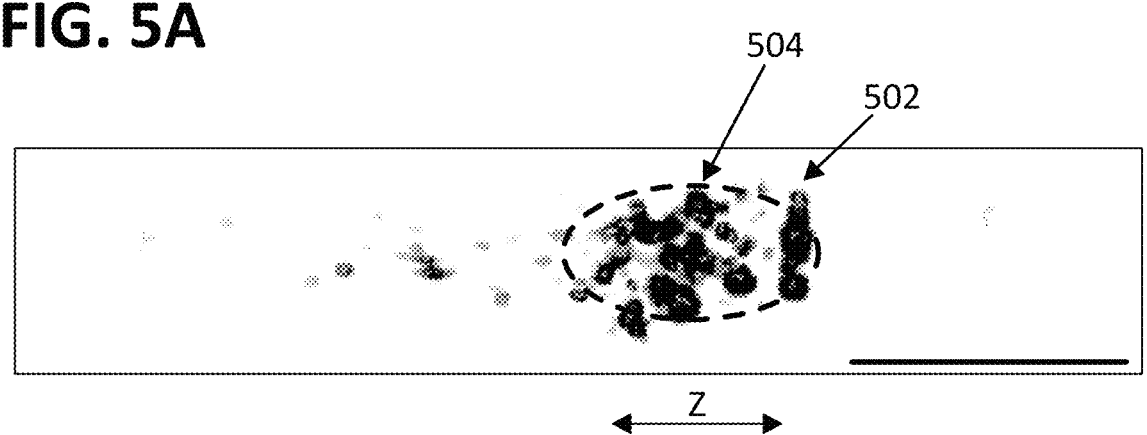
FIG. 5A illustrates one embodiment of creating a bubble cloud at a single focal location for a given discrete treatment location.

As described above, with a discrete excitation volume, the transducer focus is positioned at each discrete therapy location (e.g., planned focal locations) and a cavitation bubble cloud or focal zone is formed at each location for a pre-determined time based on the dose of therapy desired for each treatment location. FIG. 5A illustrates an example of an excitation volume 504 defined by the histotripsy bubble cloud or cavitation 502 formed at a discrete focal location. The dashed ellipses of the excitation volume 504 are intended to depict the general location of the bubble cloud but do not depict a specific size with respect to the acoustic field. In the illustrated example, the therapy transducer is assumed to be on the right side of the page, with the histotripsy pulses being delivered from right to left on the page along the z-axis of the therapy transducer. In this example, the excitation volume 504 can be placed on a discrete treatment location of a treatment plan within a target tissue volume (e.g., as depicted in FIG. 4A). As shown, the bubble cloud 502 can include bubbles, bubble clouds, or cavitation outside of the excitation volume 504.

Figure 5B:
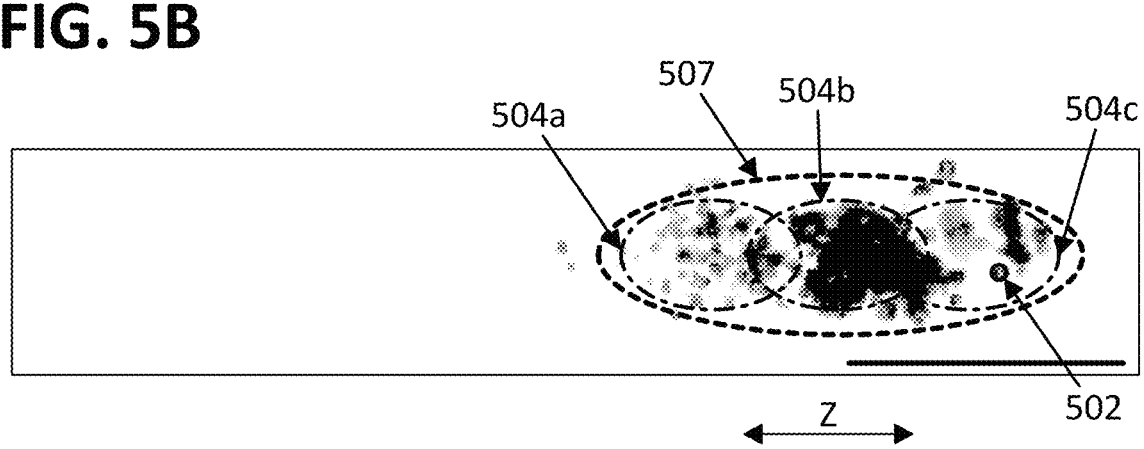
FIG. 5B illustrates one example of creating a bubble cloud with a plurality of axially spaced focal locations for a given discrete treatment location.

According to one aspect of this disclosure, as shown in FIG. 5B, an enhanced excitation volume 507 can comprise a plurality of focal zones (e.g., 504a, 504b, and 504c), and the therapy transducer can be configured and controlled to rapidly electronically beam-steer between the plurality of closely spaced focal zones 504a, 504b, and 504c to produce the cavitation or bubble cloud(s) which collectively form the enhanced excitation volume 507. In some embodiments, as shown in FIG. 5B, the steering is accomplished with electronic beam-steering of the therapy transducer array. In some examples, axial steering along the z-axis of the transducer array can be used, starting with the first focal zone 504a furthest away from the transducer. Electronic beam-steering through the focal zones can be in any direction, including proximal-most to distal-most, or starting at the central focal location and traversing either distally or proximally to the next focal zone. However, transitioning between focal zones from distal-most to proximal-most (with respect to the transducer) can advantageously limit the shielding effects of residual cavitation nuclei for the first axial pass through the focal zones.

In the embodiment shown in FIG. 5B, the focal zones 504a, 504b, and 504c are partially overlapping so as to produce an elongated, continuous enhanced excitation volume 507 across the focal zones 504a, 504b, and 504c. It is an object of this disclosure that lower amplitude regions of the histotripsy beam sufficiently overlap with previously targeted focal locations to re-excite residual nuclei. However, it should be understood that in other embodiments, the focal zones need not overlap. Generally, according to this disclosure, the system can be configured to position an enhanced excitation volume at a first discrete treatment location (e.g., by mechanically moving or manipulating the robotic positioning system), deliver a first histotripsy pulse to the first treatment location comprising the enhanced excitation volume to create a bubble cloud(s)/cavitation, rapidly electronically beam-steer the transducer array focus to a second focal location comprising the enhanced excitation volume, deliver a second histotripsy pulse to the second focal location to create a second bubble cloud(s)/cavitation, and repeat for as many desired focal locations/focal zones for the given enhanced excitation volume positioned at the discrete treatment location.

While the embodiment of FIG. 5B shows three overlapping focal zones (e.g., 504a, 504b, 504c) for each enhanced excitation volume 507, any number of focal zones can be created depending on the treatment plan, target tissue volume size, and dose of therapy required or prescribed. For example, two overlapping focal locations per enhanced excitation volume are possible, as are four or more focal locations per enhanced excitation volume, providing there is sufficient beam overlap of the lower amplitude portions of the beam re-exciting residual cavitation nuclei in previously treated focal locations.

The distance of electronic beam-steering between focal locations/zones can vary, but in general the distance between the focal locations can be optimized based on the size of the bubble cloud generated by a chosen pulse. In some examples, the distance of steering between focal locations can be based on the wavelength of the ultrasound pulses and whether the steering is axial or lateral. For a histotripsy system using a selected pulse generating the bubble cloud sizes described and depicted in this disclosure, it has been found that optimal axial spacing between focal locations can be in the range of 1 mm to 5 mm between subsequent focal locations. In one embodiment, 2.5 mm spacing between focal locations advantageously provides sufficient overlap between bubble clouds at adjacent focal locations and optimally takes advantage over lower amplitude portions of the beam re-exciting residual cavitation nuclei in previously treated focal locations to improve the consistency and continuity of the bubble cloud across all the focal locations. In embodiments where the focal locations are laterally spaced from another, the range of movement/steering can differ from that of the axially spaced embodiment. Generally, lateral spacing can be within a 1 mm radius from the focus of the transducer. In one embodiment, 0.5 mm spacing between laterally spaced focal locations advantageously provides overlap between bubble clouds at adjacent focal locations and optimally takes advantage over lower amplitude portions of the beam re-exciting residual cavitation nuclei in previously treated focal locations to improve the consistency and continuity of the bubble cloud across all the focal locations.

The histotripsy pulse delivered to each focal location can comprise, for example, a shocked scattering histotripsy pulse, such as the one illustrated in FIG. 3. For example, in FIG. 5B, the histotripsy system can be configured to position the therapy transducer focus at the first focal location 504a and deliver the histotripsy pulse of FIG. 3 to that first focal location. More specifically, the pulse can include a peak positive half cycle, followed by a peak negative half cycle, followed by a trailing positive half cycle. As shown in FIG. 3, the trailing positive half cycle can have a smaller amplitude than the peak positive half cycle. After the pulse is delivered to the first focal location, the transducer array can be rapidly electronically beam-steered to the second focal location and the pulse can be delivered to the second focal location. This process can be repeated for the third focal location. In some embodiments, the focus of the transducer is steered so rapidly, and subsequent pulses are delivered to subsequent focal locations such that a bubble cloud can be generated at a second or subsequent focal location during the life-cycle of the previous bubble cloud. In some examples, the "life-cycle" of the bubble cloud is considered to be the time during which the bubble cloud is formed within the focal location. In other embodiments, the "life-cycle" of the bubble cloud can include the presence of residual nuclei in the focal location even after the initial bubble cloud has expanded and collapsed. For example, a first bubble cloud can be generated at a first focal location with therapy pulses, and the transducer can then be rapidly electronically beam-steered to a second focal location and deliver therapy pulses to the second focal location to generate a second bubble cloud during the life-cycle of the first bubble cloud (e.g., before the first bubble cloud collapses). The overlapping focal zones combined with the rapid electronic beam-steering and repetition of this sequence creates a larger enhanced excitation volume.

In one specific embodiment, the therapy pulses can have a repetition rate of ~600 Hz, and timing of the rapid electronic beam-steering can be as follows: 1) One iteration of the therapy pulse is delivered to the first focal location (e.g., 504a in FIG. 5B). 2) The next iteration of the therapy pulse is delivered to the second focal location (e.g., 504b in FIG. 5B) via electronic beam-steering. In this example, the period of steering is equal to the period of the therapy sequence (1/600HZ~1.7 ms). 3) The next iteration of the therapy pulse is delivered to the third focal location (e.g., 504c in FIG. 5B) via electronic beam-steering; the period of steering is equal to the period of the therapy sequence (1/600 Hz~1.7 ms). 4) The next iteration of the therapy pulse is delivered at the first focal location (e.g., 504a in FIG. 5B) via electronic beam-steering; the period of steering is equal to the period of the therapy sequence (1/600 Hz~1.7 ms). And the process described above can be repeated until the target dose, which may include a target number of pulses, is delivered to the focal locations at that treatment location. While the embodiments described above and in FIG. 5B describe rapidly steering between three distinct focal locations for each enhanced excitation volume, it should be understood that other embodiments can include any number of rapidly beam-steerable focal locations (e.g., two, four, five, six, or more) and variably positioned in 3D space.

Depending on the dose desired or prescribed for a given discrete treatment location, doses of therapy can be delivered multiple times to each focal location. For example, therapy can be provided to the first focal location, then the second focal location, then the third focal location, before moving back to the first focal location and repeating the process. In other embodiments, only a single dose at each focal location may be sufficient to achieve the desired dose for that treatment location. In some embodiments, the dose is varied spatially and temporally non-uniformly across a planned treatment volume comprised of a plurality of enhanced excitation volumes. For example, the extent of therapy in each iteration can also be configurable (e.g., n pulses delivered to a first focal location followed by n pulses delivered to a second focal location followed by n pulses delivered to a third focal location, where n could be equal to 1, 2, . . . , 100 or more, etc. prior to iterating through the focal locations again).

In the embodiment of FIG. 5B, the therapy transducer can be electronically beam-steered axially along its z-axis in between the discrete focal locations. For example, the first focal location 504a can be the natural focus of the therapy transducer, the second focal location 504b can axially displaced towards the transducer by a predetermined (overlapping) distance from the first focal location, and the third focal location can be axially displaced towards the transducer from the second focal location.

Figure 5C:
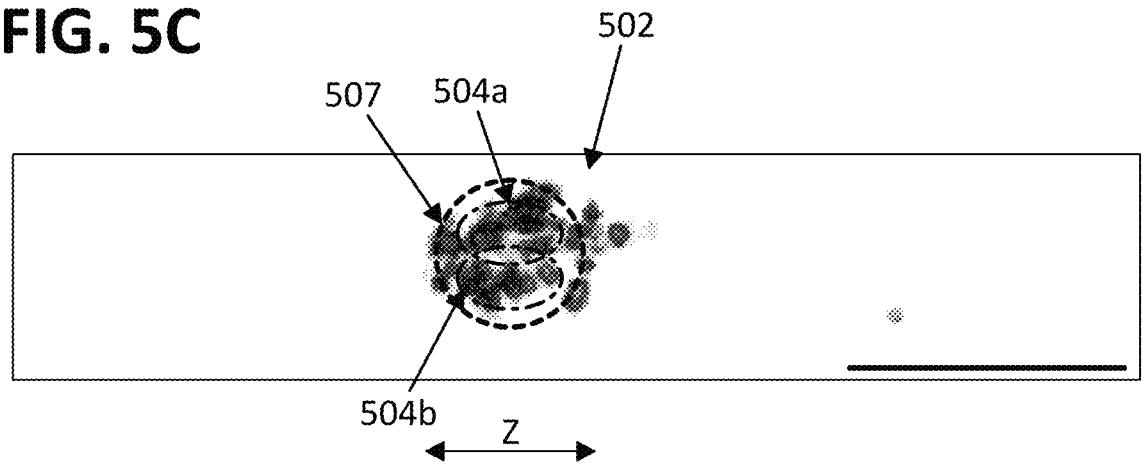
FIG. 5C illustrates one example of creating a bubble cloud with a plurality of laterally spaced focal locations for a given discrete treatment location.

It should be understood that in other embodiments, the electronic beam-steering can be implemented laterally in the x-y direction. One example of lateral electronic beam-steering is shown in FIG. 5C, in which the first focal zone 504a is displaced laterally in the x-y direction from the second focal zone 504b to form an enhanced excitation volume 507. As shown in this embodiment, the focal zones partially overlap, but as described above, while there are advantages to overlapping focal zones this is not necessary. It should also be understood that any of the steering described in FIGS. 5B and 5C can be implemented via electronic beam-steering.

While FIG. 5B shows an embodiment where multiple focal zones are spaced axially apart in the z-direction, and FIG. 5C shows an embodiment where multiple focal zones are spaced laterally apart in the x-y direction, it should be understood that in other embodiments, the rapid steering can include a combination of movement/steering in both the x-y direction and the z-direction.

Figure 6A:
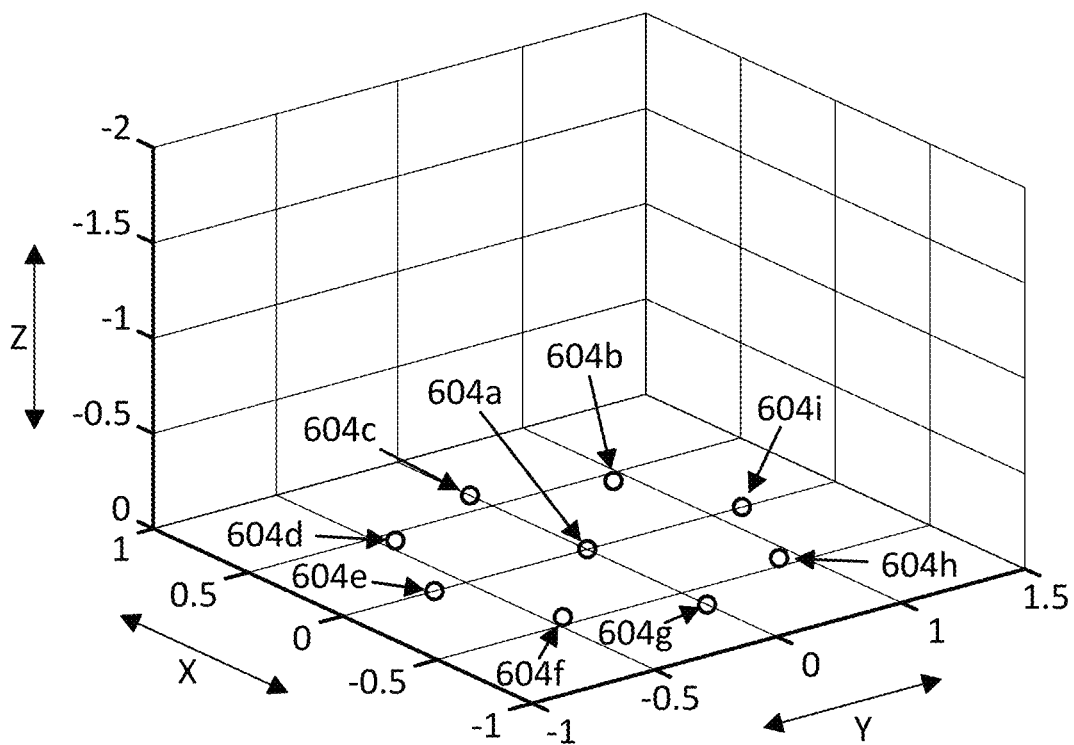
FIGS. 6A-6B illustrate one technique for electronically beam-steering an ultrasound transducer laterally to form an enhanced excitation volume.
Figure 6B:
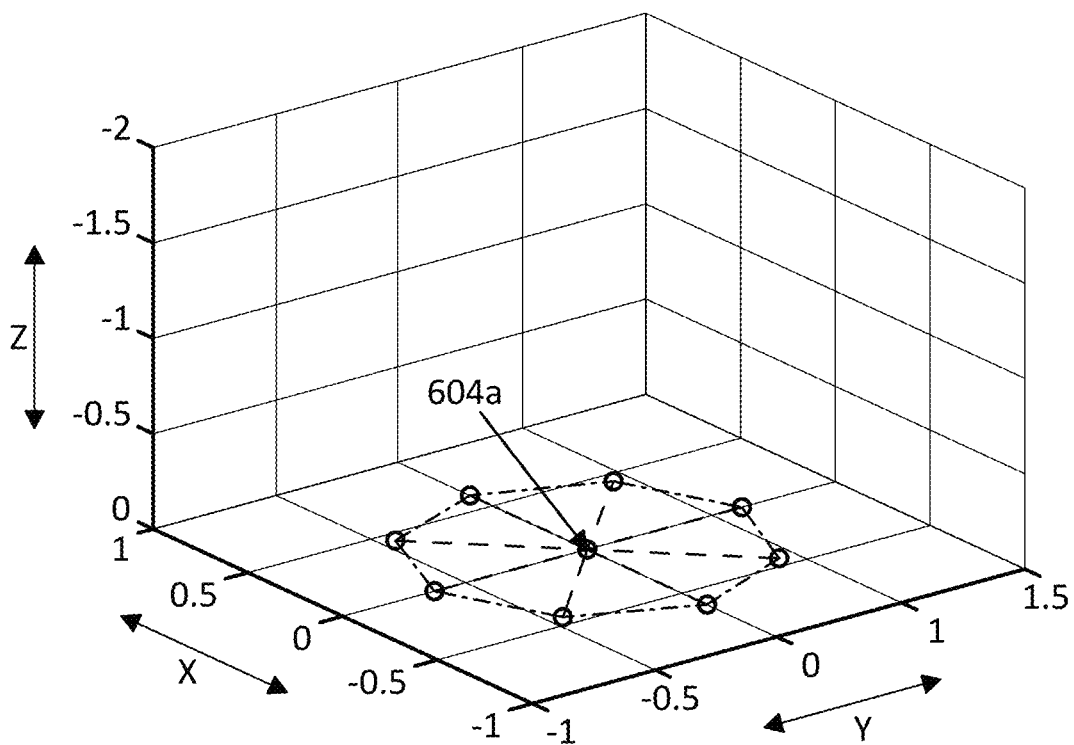

FIGS. 6A-6B illustrate one embodiment of an electronic beam-steering pattern used to generate an enhanced excitation volume. In this example, the focus of the ultrasound transducer array can be steered laterally (e.g., in the x-y axis) from the natural focus 604a of the transducer array. The specific sequence and timing of the electronic beam-steering can be selected and chosen to optimally maintain cavitation and/or advantageously use or re-excite residual cavitation. In one specific embodiment, the histotripsy therapy can be initiated at the natural focus 604a of the transducer array. The focus can then be sequentially electronically beam-steered through the remaining focal locations of the enhanced excitation volume, moving from natural focus 604a to focal locations 604b, 604c, 604d, 604e, 604f, 604g, 604h, and 604i. The individual points marked as focal locations in FIGS. 6A-6B represent the center of the focal locations. It should be understood that the focal zones themselves corresponding to the bubble cloud or cavitation created when histotripsy therapy is delivered can be overlapping in the illustrated embodiments.

While the beam-steering pattern of FIG. 6A is shown generally as a wheel or ring around the central natural focus, it should be understood that the pattern can be traversed either clockwise or counter-clockwise in direction.

Furthermore, according to some embodiments, the beam-steering pattern may revisit or repeat therapy delivery to some or all of the focal locations as the transducer array is beam-steered through the locations. The parameters for revisiting or repeating therapy delivery to focal locations can be predetermined, or customized by a user. In one embodiment, an important element of the electronically steered patterns is that in succession at the steered focal location within the enhanced volume there are both instances of new cavitation events and the restimulation of residual nuclei. In addition to these events at the current focal location, previously sonicated locations are being treated by the re-excitation of their residual nuclei. This process of periodically revisiting points can greatly assist in the sustained cavitation across the enhanced excitation volume, especially along a central axis of the transducer. In practice, it has been determined that periodically revisiting the central axis of the enhanced excitation volume during traversal of the electronic beam-steering pattern is beneficial to maintaining cavitation throughout the enhanced excitation volume.

Therefore, according to one embodiment and further depicted in FIG. 6B, the natural focus 604a of the enhanced excitation volume can be re-excited after a predetermined number of focal locations (e.g., after every new focal location, every 2 focal locations, every 3 focal locations, etc.). Alternatively, the steering logic can require that 2 or fewer, 3 or fewer, 4 or fewer, or 5 or fewer locations are treated before returning to a focal location along the central axis of the transducer to re-excite that focal location along the center axis of the transducer.

For example, one specific beam-steering pattern may require revisiting and re-exciting the natural focus (or a focal location central to the beam steering pattern) at least every 3 focal locations. Referring to FIG. 6A, this beam-steering pattern may start at the natural focus 604a, electronically beam-steer to focal location 604b and then to focal location 604c, before returning to natural focus 604a maintaining re-excitation of that entire steered sector throughout the raster of the pattern. The pattern can then continue to focal location 604c, move to focal location 604d, and then return to natural focus 604a. From there, the pattern can continue back to focal location 604d, to focal location 604e, to natural focus 604a, back to focal location 604e, to focal location 604f, to natural focus 604a, back to focal location 604f, to focal location 604g, to natural focus 604a, back to focal location 604g, to focal location 604h, to natural focus 604a, back to focal location 604h, and finally to focal location 604i. In the pattern described above, at least a portion of the natural focus 604a is re-excited every 3 focal locations. This ensures that the residual nuclei in the central portion of the enhanced excitation volume (e.g., in an axial plane that intersects at least partially with the natural focus of the transducer) is periodically being re-excited (e.g., after a set number of focal locations), and furthermore assists with cavitation formation at the peripheral/perimeter focal locations. While the electronic beam-steering pattern of FIGS. 6A-6B steers between focal locations only laterally from the natural focus (e.g., in the x-y plane), it should be understood that the enhanced excitation volume exists in three-dimensions. The result of this lateral steering is to increase the lateral dimensions of the enhanced excitation volume, which serves to form a more spherical excitation volume compared to the generally column shaped excitation volume that is formed at a single focal location.

Figure 7A:
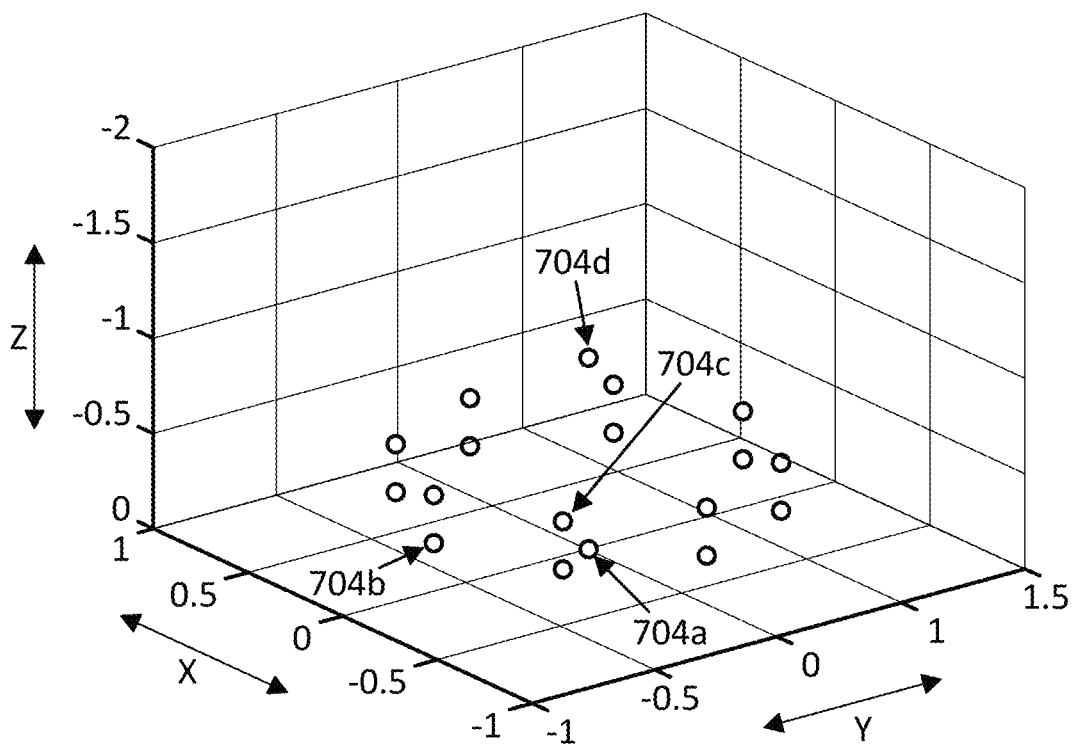
FIGS. 7A-7B illustrate one technique for electronically beam-steering an ultrasound transducer in 3D space to form an enhanced excitation volume.
Figure 7B:
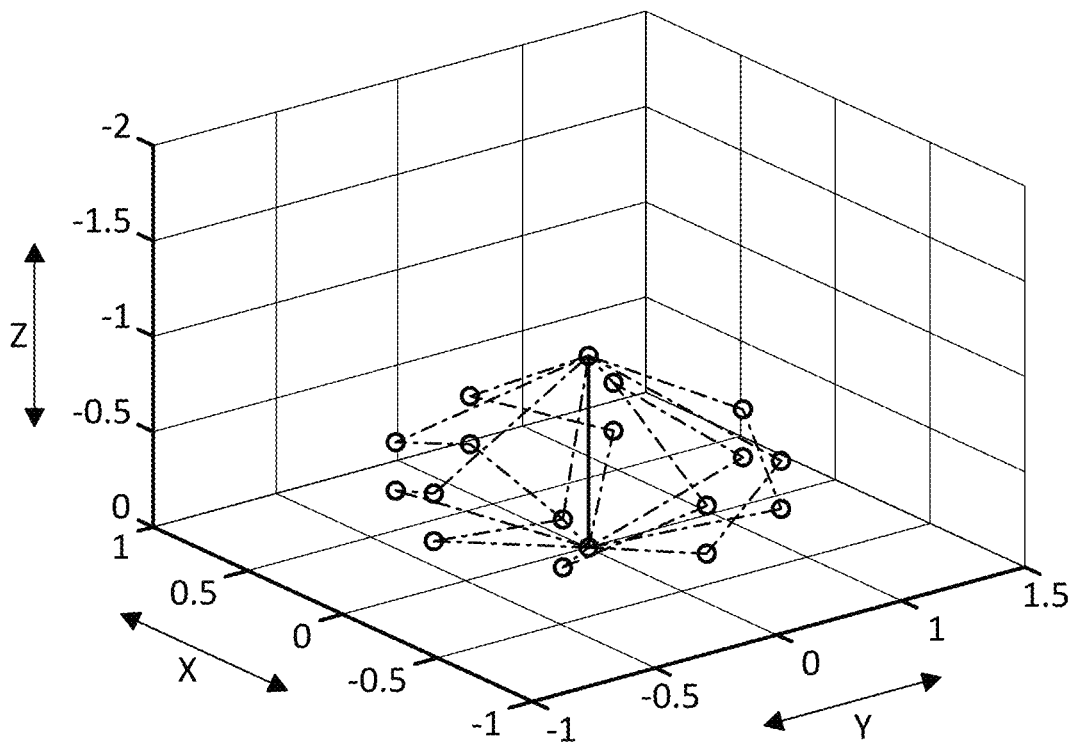

FIGS. 7A-7B describe another embodiment of an electronic beam-steering pattern that includes beam-steering in 3D space (e.g., a combination of steering in the x, y, and z directions). Similar to the pattern described in FIGS. 6A-6B, the pattern in FIGS. 7A-7B can include an electronic beam-steering pathway of plurality of equilateral triangles. However, these triangles have been stretched over the axial (z)

dimension resulting in curved arcs from the natural focus (0,0,0) to (0,0,-Z) with the two intervening points located at ¼ and ½(-Z). A single arc moves from the natural focus of the transducer $704a$=(0,0,0) to $704b$=((sqrt(2)*R/2), -(sqrt(2)*R)/2, -Z/4) to $704c$=(R,0,-Z/2) and returns to the central axis at $704d$=(0,0,-Z). The entire arc can be rotated 45° every fifth pulse when the pattern again returns to $704a$ at the natural focus. In some embodiments, the rotation could be finer (e.g., less than) 45° or more coarse (e.g., up to 90°) depending on the implementation. In the example of FIGS. 7A-7B, the residual nuclei in a central axis of the enhanced excitation volume (e.g., an axial plane that intersects with the natural focus of the transducer) is at least partially re-excited after a set number of focal locations to maintain cavitation in the central axis and assist with cavitation formation at focal locations on the periphery, lateral to the central axis, or outside of the central axis of the enhanced excitation volume. The pattern iterates through an ordered list of the planned focal locations with $704a$ and $704d$ bookending each series of four points resulting in 18 unique focal locations for a pattern with 32 planned focal locations. The 32-point rotated pattern can then be repeated until reaching the proscribed dose for each target location within a given volumetric plan.

Figure 8A:
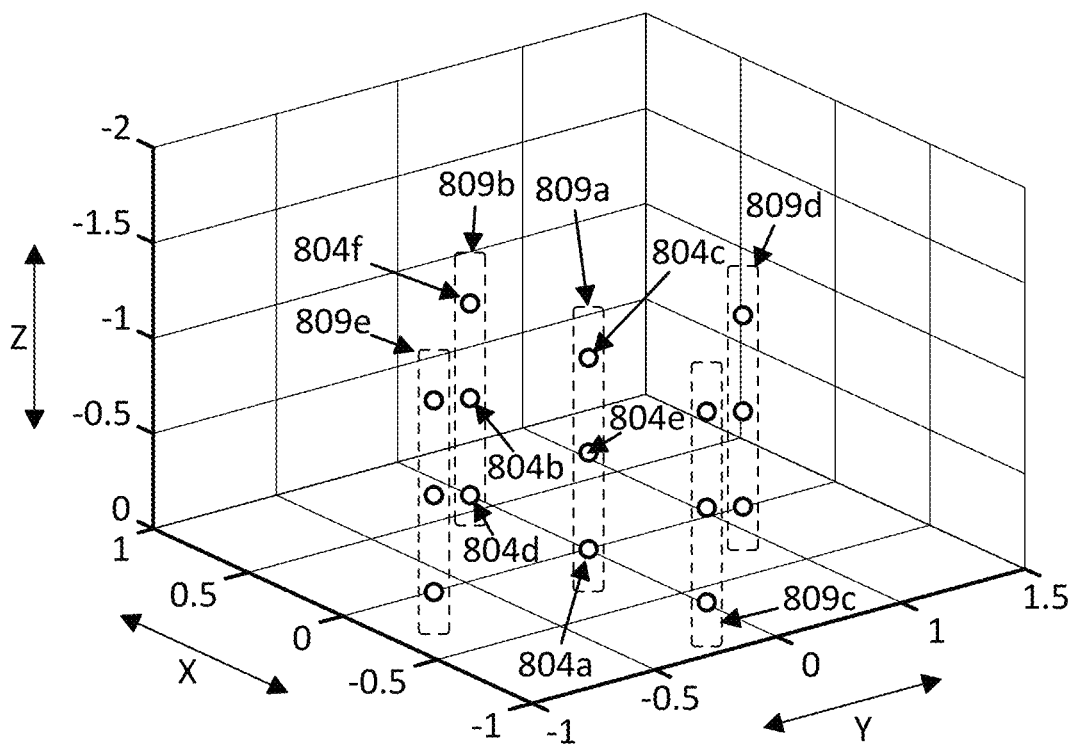
FIGS. 8A-8B illustrate one technique for electronically beam-steering an ultrasound transducer in 3D space to form an enhanced excitation volume.
Figure 8B:
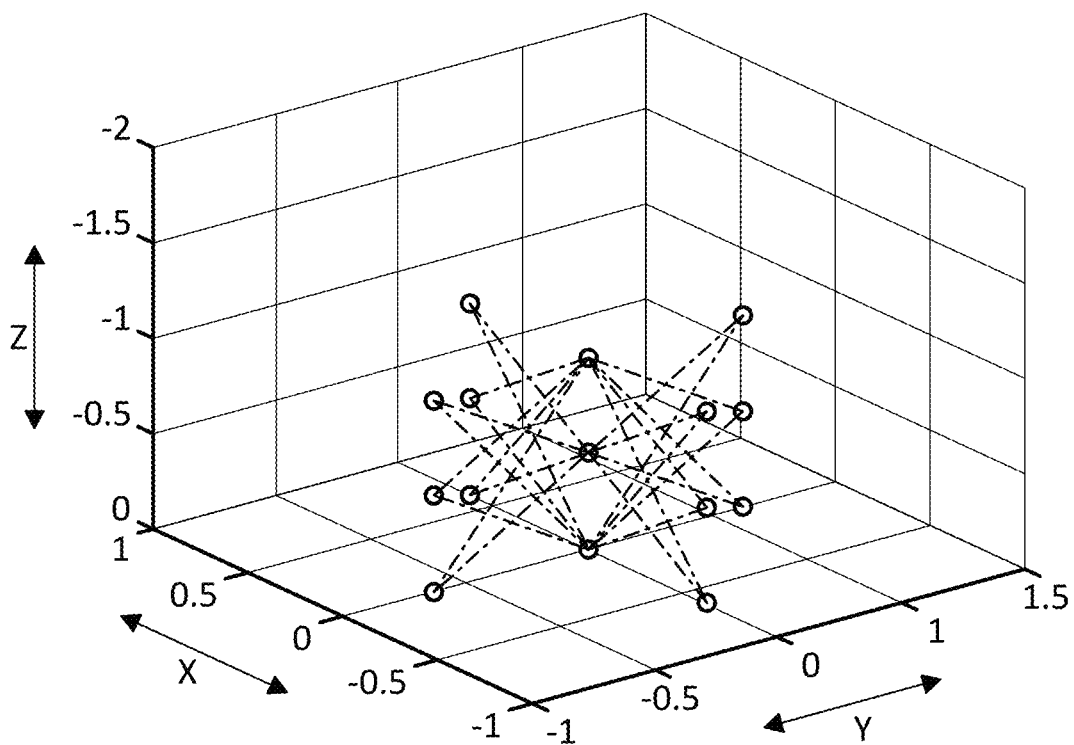

FIGS. 8A-8B illustrate yet another embodiment of an electronic beam-steering pattern that includes beam-steering in 3D space between overlapping focal locations. In the embodiment of FIGS. 8A-8B, the beam-steering pattern comprises a central column $809a$ of focal locations positioned within a plurality of vertical or axial peripheral or outer columns $809b/c/d/e$ of focal locations. It should be understood that in FIGS. 8A-8B, the therapy transducer is positioned at the top of the page and directing ultrasound energy towards the bottom of the page. In some examples, the central column can contain the natural focus $804a$ or at least partially overlap with the natural focus of the therapy transducer array or be positioned along a central axis of the transducer array. Bubble clouds formed at focal locations in the central column $809a$ may partially overlap with bubble clouds formed at focal locations in the peripheral columns $809b/c/d/e$.

In some embodiments, the beam-steering pattern of FIGS. 8A-8B may revisit or repeat therapy delivery to some or all of the focal locations within the central column $809a$ or within a central axis of the transducer array as the transducer array is beam-steered through the focal locations in columns $809b/c/d/e$. The parameters for revisiting or repeating therapy delivery to focal locations within the central column or central axis can be predetermined, or customized by a user. In practice, it has been determined that at least partially revisiting the central column or central axis focal locations of the enhanced excitation volume periodically during traversal of the electronic beam-steering pattern can advantageously re-excite residual cavitation in the center of the volume, which then assists with enhanced cavitation at the peripheral or perimeter focal locations. Therefore, according to one embodiment and further depicted in FIG. 8B, a focal location in the central column $809a$ of focal locations of the enhanced excitation volume can be re-excited after a predetermined number of focal locations (e.g., after every new focal location, every 2 focal locations, every 3 focal locations, etc.). In practice, it has been determined that revisiting at least one focal location in the central column of the enhanced excitation volume periodically during traversal of the electronic beam-steering pattern is beneficial to maintaining cavitation throughout the enhanced excitation volume.

In one specific embodiment, the steering pattern is initiated by forming cavitation at the natural focus $804a$ of the central column $809a$. Electronic beam-steering can then shift the focus of the transducer array to focal location $804b$ in column $809b$ (the central focal location in that column), then returning the focus to focal location $804c$ in column $809a$. To complete excitation in both the central column and column $809b$, the electronic beam-steering can continue by exciting focal location $804d$ in column $809b$, then focal location $804e$ in central column $809a$, then focal location $804f$ in column $809b$. The steering pattern can then initiate cavitation in a new column (e.g., $809c$), and continue the pattern of exciting a focal location in an outer or peripheral column followed by exciting a focal location in the central column. It is noted that in this specific implementation, the order of excitation/steering within the columns remains consistent. For example, the order of excitation of focal locations within the central column can start with the natural focus $804a$, move to an outer or peripheral column, return to focal location $804c$, move to the outer or peripheral portion, and then return to the central focal location $804e$ within the central column. Similarly, the pattern within outer or peripheral columns can also follow a specific sequence, e.g., starting with a central focal location within a given outer or peripheral column (e.g., focal location $804b$ in column $809b$), returning to the central column, steering back to the lower or distal focal location in the outer or peripheral column (e.g., focal location $804d$ in column $809b$), returning to the central column, and then moving to the top or proximal focal location in that column (e.g., focal location $804f$ in column $809b$). In some embodiments, steering can be performed from the most distal point to the most proximal point in any series of three focal locations before returning to the most distal end of the pattern to begin a new series of three points.

In some aspects, the specific order of excitation within a column can be changed from as described above, however the overall concept of alternating between the central column and a peripheral column with each subsequent therapy pulse sequence delivery can be maintained. It is also desirable to re-excite each focal location within the central column once before repeating the process. For example, focal locations $804a$, $804c$, and $804e$ should all be re-excited in some pre-determined order, instead of re-exciting focal location $804a$ twice before re-exciting focal location $804c$ once.

Generally, it is desirable to alternate between a single peripheral or outer column and the central column, until all points in both columns have been excited/re-excited, before moving on to a different peripheral column/central column pair. However, it should be understood that other embodiments can include electronically steering between columns without exciting/re-exciting all focal locations in each peripheral column.

FIG. 8B shows the general pathway between focal locations of all the columns. the result is a 3D steering pattern that includes electronic steering between the central column and peripheral columns, with control logic that requires re-excitation of central column focal locations to assist in maintaining cavitation throughout the enhanced excitation volume.

The rapid electronic beam-steering concepts described and shown herein serve to advantageously account for residual cavitation nuclei to enhance treatment of a discrete target location by creating an enhanced excitation volume with overlapping or adjacent focal zones.

In the example of FIG. 5B in which the rapid steering is in the z-direction towards the transducer for each subsequent focal location, residual cavitation nuclei tend to reside in the prior focal location. For example, in FIG. 5B, after the first pulse is delivered to the first focal location to form a focal zone 504a, the bubble cloud rapidly expands and collapses, and residual cavitation nuclei remain in the vicinity of the first focal zone. Instead of transmitting another pulse to the first focal location, the system instead rapidly steers to the second focal location and delivers another pulse to that location, forming another and overlapping focal zone 504b that is substantially free from the interference or negative effects of the residual cavitation nuclei remaining at the first focal zone 504a. It should be noted that this benefit is achieved because the focus of the transducer is steered in the z-direction towards the therapy transducer, as opposed to being steered away from the therapy transducer. This allows the residual cavitation nuclei to remain distal to the current bubble cloud. If instead, the focus were steered to a new focal location away from the transducer (e.g., distal to earlier bubble clouds), then subsequent pulses would have to travel through residual cavitation nuclei, which may cause issues with bubble cloud formation and/or dispersion or uniformity of the subsequent bubble clouds. While the second focal zone 504b is free from residual cavitation nuclei, the nuclei that remain in the vicinity of the first focal zone 504a can be re-excited by the pulse delivered to the second focal location effectively enlarging the bubble cloud at that focal zone (e.g., forming cavitation at the first focal zone 504a and the second focal zone 504b with pulse(s) delivered to the second focal location). Similarly, the transducer can then be rapidly steered to the third focal location, and another pulse can be delivered to generate cavitation at the third focal zone 504c. During this first pass, the third focal zone 504c is relatively free of residual cavitation nuclei, maximizing the efficiency of pulses delivered to the third focal location. Additionally, residual cavitation nuclei in the first focal zone 504a and the second focal zone 504b can also be re-excited by the pulse(s) delivered to the third focal location, effectively increasing the size of the enhanced excitation volume. During this first pass, the third focal zone 504c is free from remnant nuclei. Given the desire to rapidly steer and re-excite remnant nuclei, the choice of electronic steering direction minimizes the number of times that the system must steer distal to a point at which a cloud was generated immediately prior (thus minimizing the effects of shielding to the best extent possible, although not eliminating them). As described, the position of the focal locations/zones and the steered direction and pathway to the next and/or adjacent focal location can be varied based on desired effects (e.g., more advantageous to re-initiate versus potential to act as a blocker) and may contemplate how therapy versus bubble manipulation are phased in context to one another.

The time to return to a given focal location for additional therapy pulses can also be adjusted or controlled for to account for residual cavitation nuclei. In one embodiment, the following equation can be used to determine the timing of steering the beam between focal locations and/or returning to previously treated focal locations:

$$\text{time to return to given focal location} = \text{number of unique focal locations}/\text{PRF}$$

As described in the equation, for some embodiments and focal locations, the time to return to a given focal location can equal the number of unique focal locations (e.g., three focal locations) divided by the pulse repetition frequency (PRF) of the pulse.

As described above, a therapy pulse of a given pulse sequence delivered to each focal location can be a shocked scattering pulse that can include a peak positive half cycle, followed by a peak negative half cycle, followed by a trailing peak positive half cycle. This pulse is generally responsible for forming cavitation at each focal location.

In some embodiments, the specific pulse can include one or more low amplitude pulses following the therapy pulses that are designed and configured to manipulate, push, interact with, or suppress residual cavitation nuclei. In one embodiment, these additional pulses can comprise one, two, or more low amplitude pulses. These low amplitude pulses can have an amplitude that is substantially smaller than the amplitude of the therapy pulse(s). In some embodiments, the low amplitude pulses are designed and configured to push or flush out residual cavitation nuclei from previously treated focal locations. In other embodiments, the low amplitude pulses are designed and configured to spatially modulate cavitation nuclei within the previously treated focal location. For example, referring to FIG. 5B, the focus of the transducer can be positioned on first focal location 504a, and a shocked scattering pulse can be delivered to the first focal location to create a bubble cloud on the first focal location, as previously described. Immediately following the shocked scattering pulse, the transducer array can deliver one or more low amplitude pulses into the focal location to spatially modulate cavitation nuclei within the first focal location. Next, the transducer array can be rapidly steered to the second focal location, and treatment can continue as previously described. Simply put, the pulse can be modified to include a plurality of low amplitude pulses immediately following the therapy or shocked scattering pulses so as to advantageously spatially modulate or manipulate residual cavitation nuclei in a favorable way.

Figure 9A:
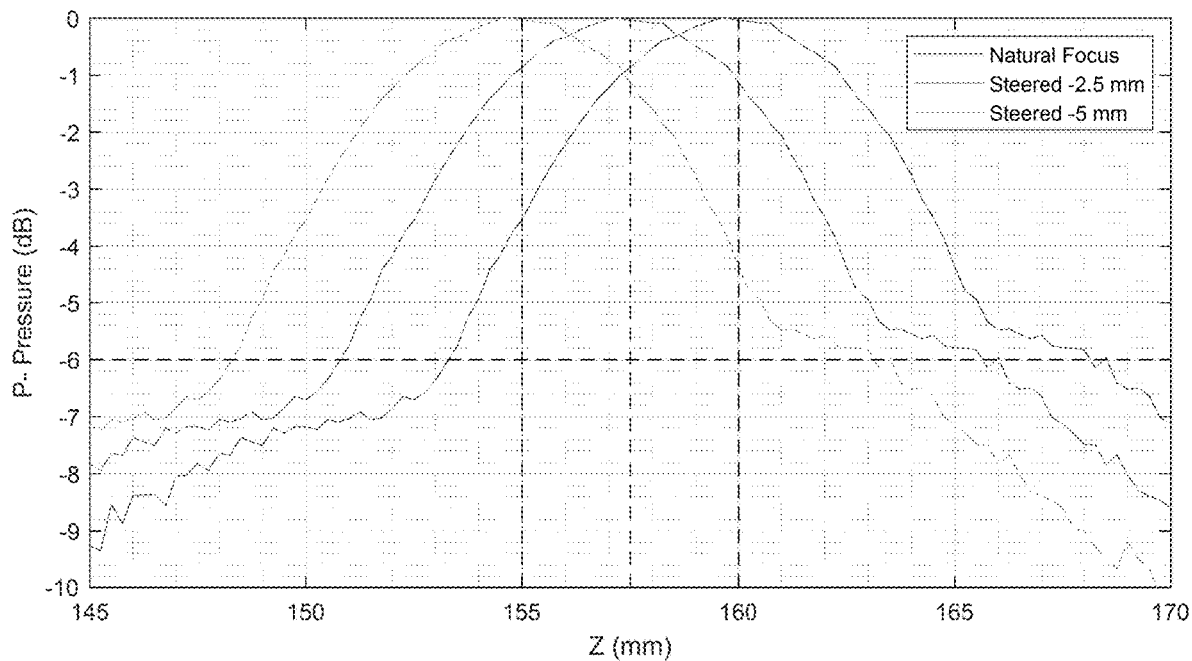
FIGS. 9A-9D illustrate beam profiles for a plurality of axially spaced bubble cloud focal locations.
Figure 9B:
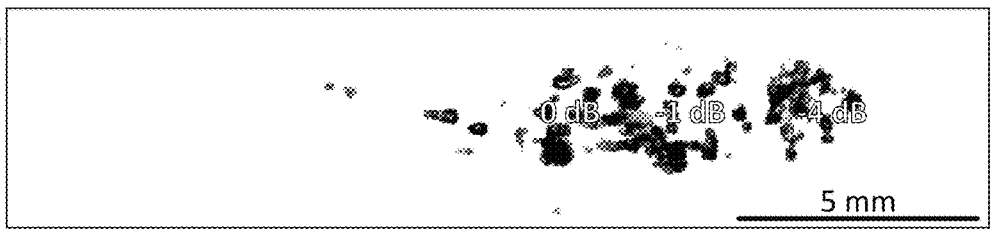
Figure 9C:
Figure 9D:
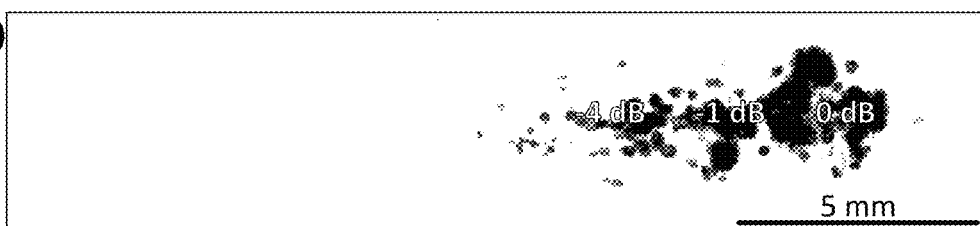

FIG. 9A illustrates an axial beam profile for axially spaced focal locations illustrated in FIGS. 9B, 9C, and 9D. These focal locations can correspond to focal zones 504a, 504b, and 504c and focal locations described above in reference to FIG. 5B. In this embodiment, the first focal location, shown in FIG. 9B, corresponds to the natural focus of the therapy transducer. FIG. 9C depicts the second focal location steered 2.5 mm in the z-direction towards the transducer from the first focal location. FIG. 9D depicts the third focal location steered 2.5 mm in the z-direction towards the transducer from the second focal location.

Figure 10A:
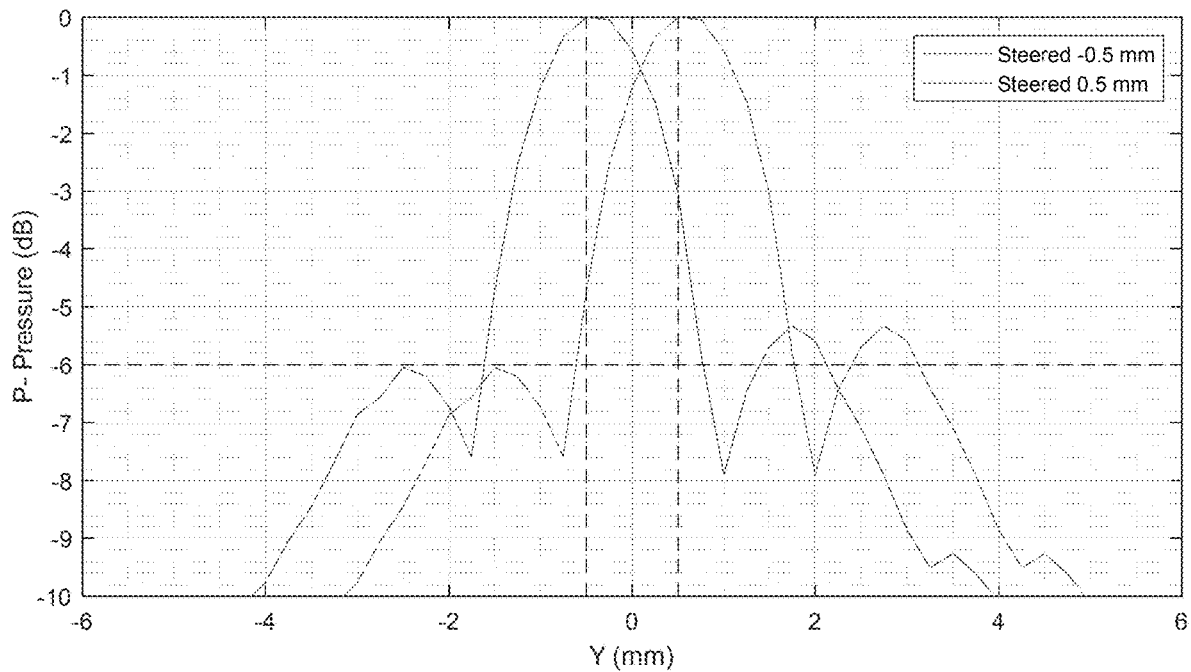
FIGS. 10A-10C illustrate beam profiles for a plurality of laterally spaced bubble cloud focal locations.
Figure 10B:
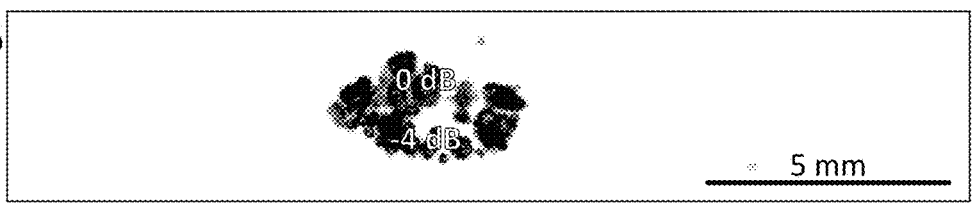
Figure 10C:
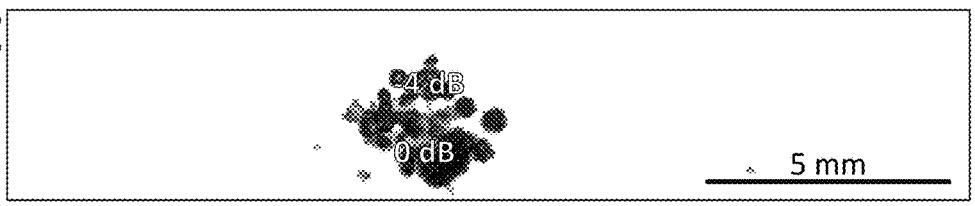

FIG. 10A illustrates an axial beam profile for laterally spaced focal locations illustrated in FIGS. 10B, and 10C. These focal locations can correspond to focal zones 504a and 504b described above in reference to FIG. 5C. In this embodiment, the first focal location, shown in FIG. 10B, corresponds to a location steered 0.5 mm in the y direction from the natural focus of the therapy transducer. FIG. 10C depicts the second focal location steered 0.5 mm in the opposite direction from the natural focus of the therapy transducer (e.g., −0.5 mm from the natural focus).

Figure 11A:
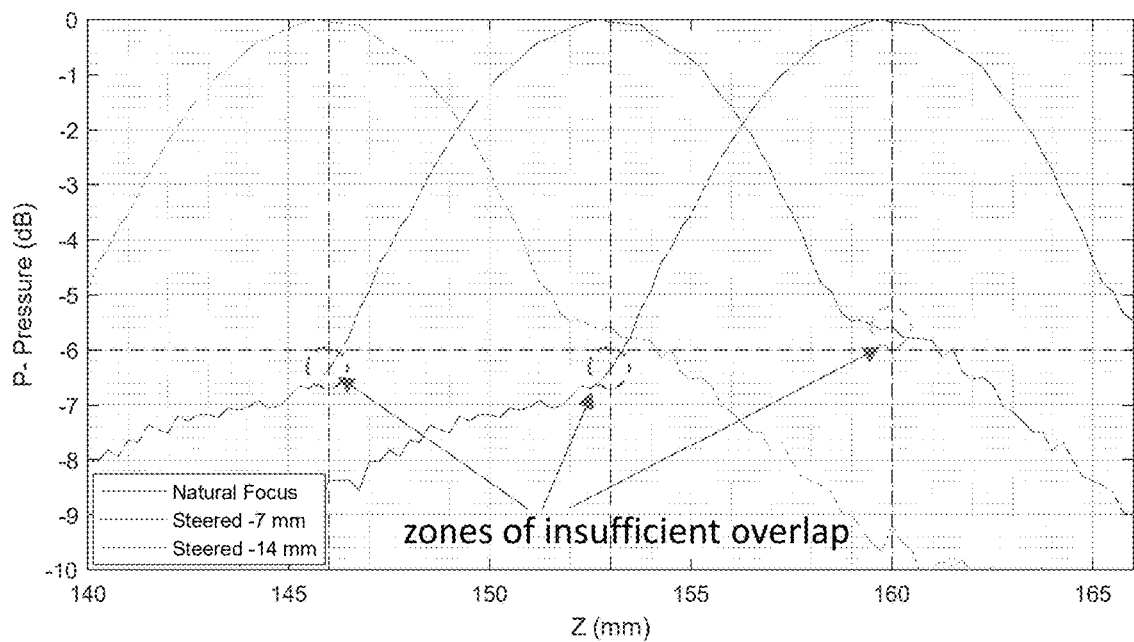
FIGS. 11A-11B illustrate the effect of spacing between adjacent focal locations.
Figure 11B:
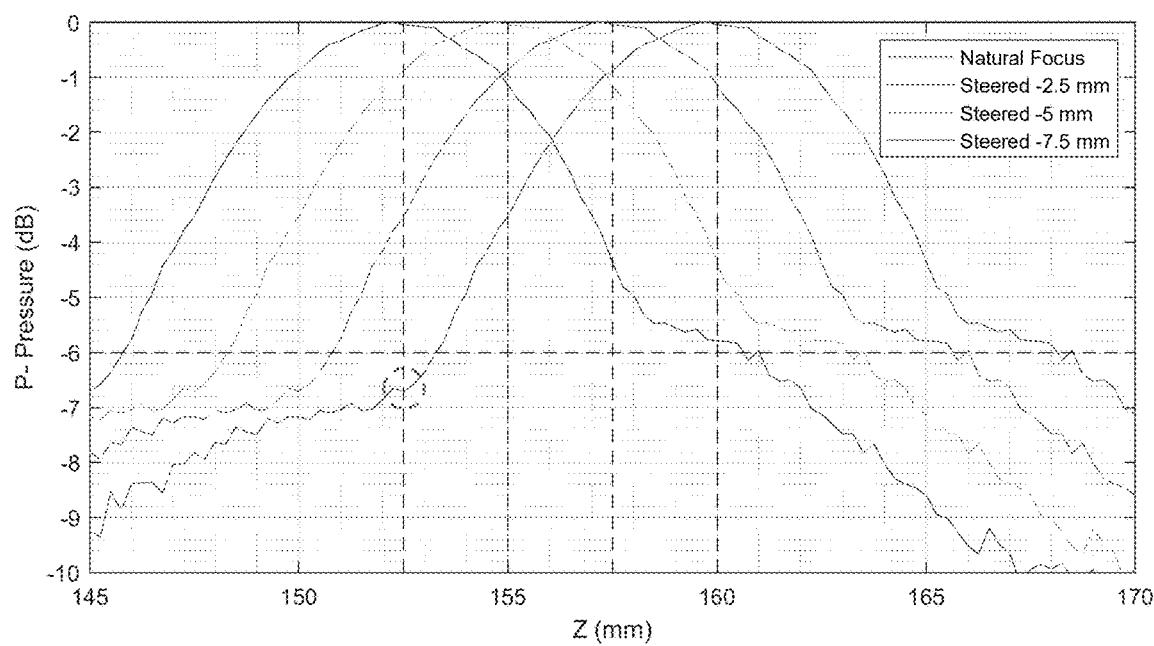

FIGS. 11A and 11B illustrate how the spacing between focal locations can affect overlap between adjacent focal zones and determine whether or not residual cavitation nuclei are re-excited by subsequent therapy pulses. In the graph of FIG. 11A, spacing between the three focal locations comprises 7 mm in the axial direction between each adjacent focal location, resulting in a first focal location at the natural focus of the transducer, a second focal location 7 mm axially spaced from the first focal location, and a third focal location 7 mm axially spaced from the second focal location. In this example, the spacing results in focal zones of insufficient overlap between adjacent beam profiles, causing the overall treatment at that treatment location (i.e., within the enhanced excitation volume) to be non-uniform. In contrast, the example of FIG. 9A, with 2.5 mm spacing between adjacent focal locations, results in sufficient overlap between adjacent focal zones to facilitate re-excitation of residual cavitation nuclei and more uniform cavitation distributions in the treatment location.

Figure 12A:
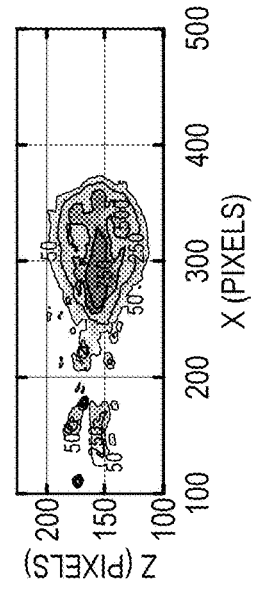
FIGS. 12A-12I illustrate heat maps, exposure levels, and lesion levels for a plurality of treatment protocols.
Figure 12D:
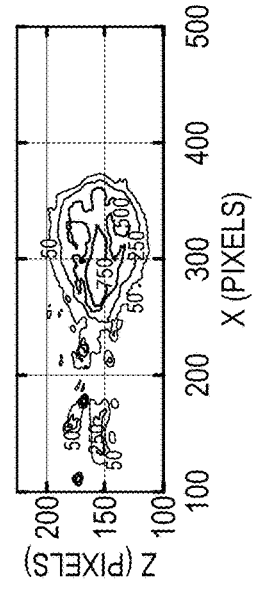
Figure 12G:
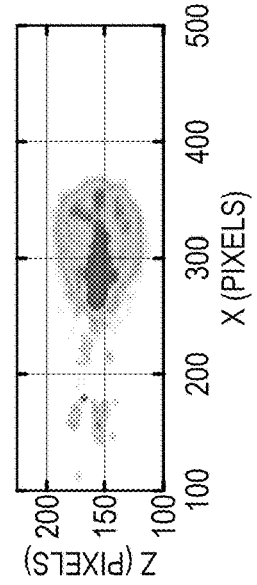
Figure 12B:
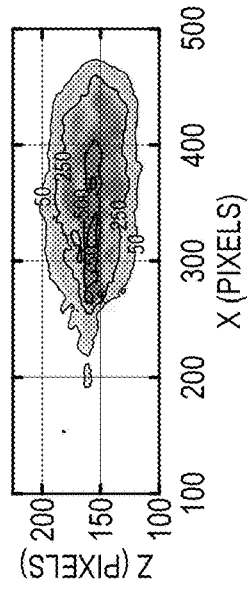
Figure 12E:
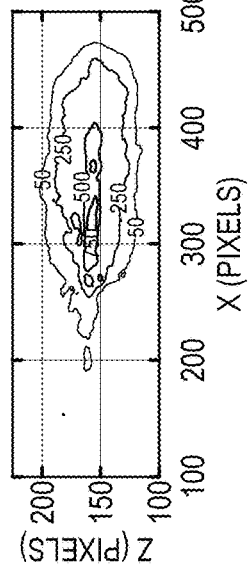
Figure 12H:
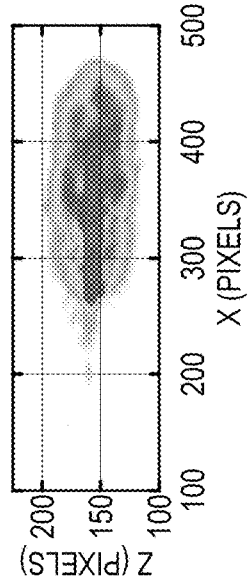
Figure 12C:
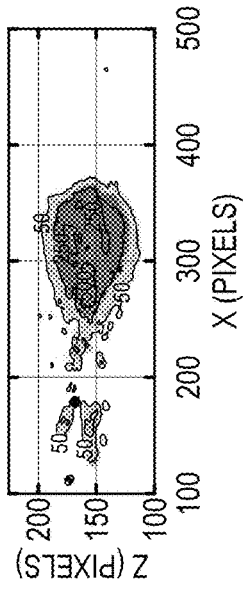
Figure 12F:
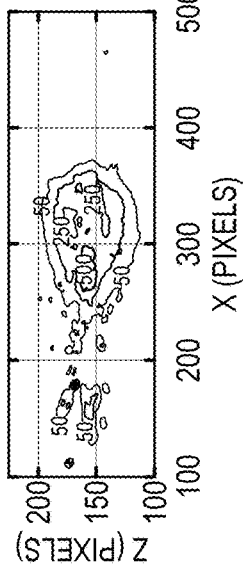
Figure 12I:
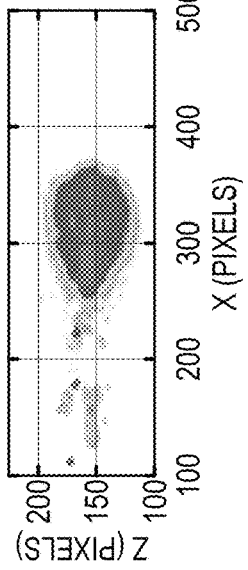

FIGS. 12A, 12B, and 12C illustrate heat maps for histotripsy therapy provided to 1) a single focal location at a treatment location with 1000 pulses delivered (FIG. 12A), 2) three axially spaced focal locations at a treatment location with a total of 1000 pulses delivered amongst them (FIG. 12B), and 3) a single focal location at a treatment location with 580 pulses delivered (FIG. 12C). FIGS. 12D, 12E, and 12F illustrate exposure levels for histotripsy therapy provided to 1) a single focal location at a treatment location with 1000 pulses delivered (FIG. 12D), 2) three axially spaced focal locations at a treatment location with a total of 1000 pulses delivered amongst them (FIG. 12E), and 3) a single focal location at a treatment location with 580 pulses delivered (FIG. 12F). FIGS. 12G, 12H, and 12I illustrate lesion and exposure levels for histotripsy therapy provided to 1) a single focal location at a treatment location with 1000 pulses delivered (FIG. 12G), 2) three axially spaced focal locations at a treatment location with a total of 1000 pulses delivered amongst them (FIG. 12H), and 3) a single focal location at a treatment location with 580 pulses delivered (FIG. 12I). Compared to treatment at a single focal location, the treatment that includes three axially spaced focal locations (FIGS. 12B, 12E, 12H) distributes a sufficiently destructive # of exposures over a greater area for same number of pulses. In one experiment, treatment of a 3 cm sphere of tissue with a plurality of discrete treatment locations, wherein each treatment location is treated with a single focal location (e.g., the treatment protocol of FIGS. 12A, 12D, 12G) resulted in "therapy on-times" of 21 minutes and 26 seconds. In contrast, treatment of a 3 cm sphere of tissue with a plurality of discrete treatment locations, wherein each treatment location is treated with three axially spaced focal locations (e.g., the treatment protocol of FIGS. 12B, 12E, 12H) resulted in "therapy on-times" of only 12 minutes and 21 seconds, a major reduction in therapy on-times.

The embodiment of FIGS. 12C, 12F, and 12I shows what treatment would look like at a single focal location for each discrete treatment location of a 3 cm sphere of tissue with a therapy on-time matching that of the embodiment of FIGS. 12B, 12E, and 12H (e.g., 12 minutes and 21 seconds of on-time). As can be seen, the heat map, exposure level, and lesion generation lag far behind the other two embodiments. This experiment shows how rapid steering of the transducer between multiple focal locations for a given treatment location can improve the quality of therapy and rapidly reduce the amount of on-time (e.g., dosage of ultrasound energy) delivered for a given treatment. Rapid steering between multiple focal locations for a given discrete treatment location uses the same number of pulses more efficiently than single focal location treatment by distributing a sufficiently destructive number of exposures over a larger volume.

FIG. 13 is a schematic drawing showing the spatial relationship between a therapy transducer 1300, a first focal location 1304a, a second focal location 1304b, and a third focal location 1304c. As described above, in some embodiments, the first focal location can comprise the natural focus of the transducer, and the second and third focal locations can be achieved with electronic steering of the transducer array. In this example, a distance dz separates adjacent focal locations.

Figure 14:
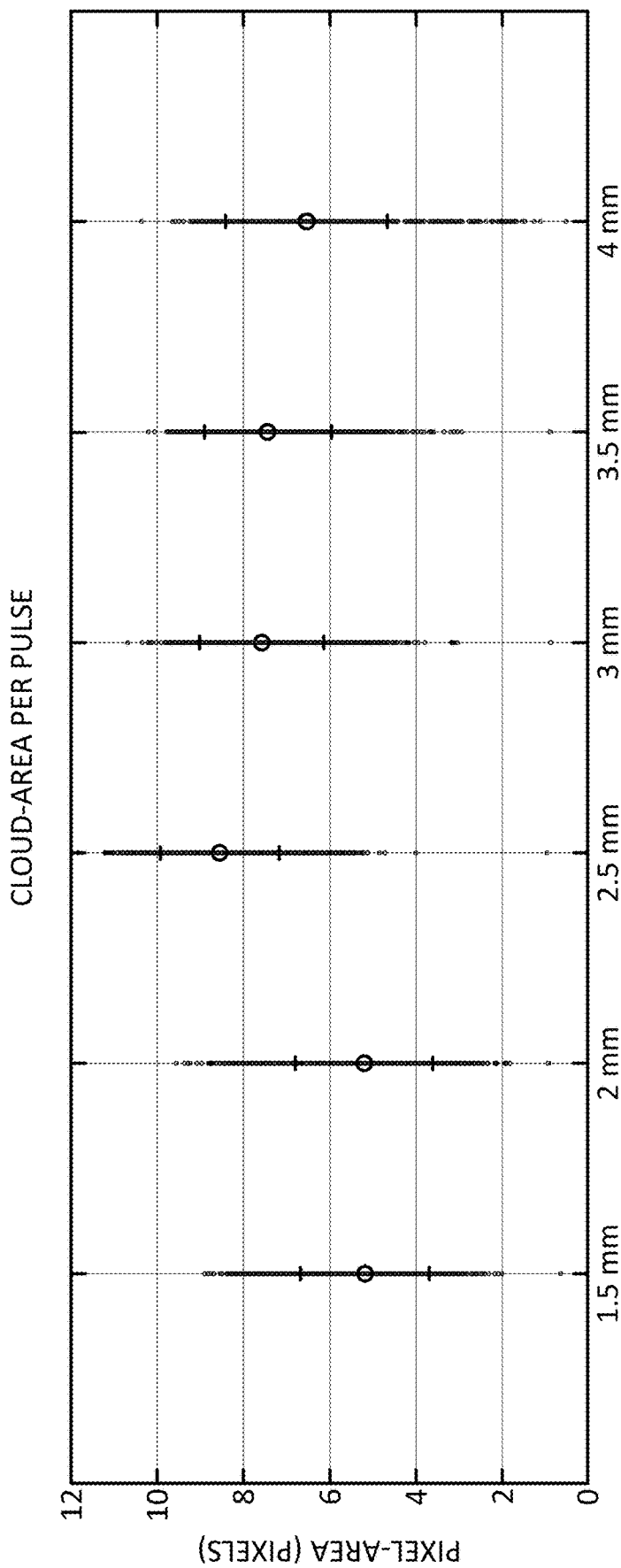
FIG. 14 is a chart showing the effect of spacing on bubble cloud size.

FIG. 14 illustrates the relationship between bubble cloud size (area) and the distance between adjacent focal locations. As shown in FIG. 14, in one embodiment, 2.5 mm spacing between focal locations also produces the largest cloud per pulse, highlighting how previously excited zones can be re-excited by targeting adjacent zones, enlarging the cloud on a per pulse basis.

Therapy Components

The Therapy sub-system may work with other sub-systems to create, optimize, deliver, visualize, monitor and control acoustic cavitation, also referred to herein and in following as "histotripsy", and its derivatives of, including boiling histotripsy and other thermal high frequency ultrasound approaches. It is noted that the disclosed inventions may also further benefit other acoustic therapies that do not comprise a cavitation, mechanical or histotripsy component. The therapy sub-system can include, among other features, an ultrasound therapy transducer and a pulse generator system configured to deliver ultrasound pulses into tissue.

In order to create and deliver histotripsy and derivatives of histotripsy, the therapy sub-system may also comprise components, including but not limited to, one or more function generators, amplifiers, therapy transducers and power supplies.

The therapy transducer can comprise a single element or multiple elements configured to be excited with high amplitude electric pulses (>1000V or any other voltage that can cause harm to living organisms). The amplitude necessary to drive the therapy transducers for Histotripsy vary depending on the design of the transducer and the materials used (e.g., solid or polymer/piezoelectric composite including ceramic or single crystal) and the transducer center frequency which is directly proportional to the thickness of the piezo-electric material. Transducers therefore operating at a high frequency require lower voltage to produce a given surface pressure than is required by low frequency therapy transducers. In some embodiments, the transducer elements are formed using a piezoelectric-polymer composite material or a solid piezoelectric material. Further, the piezoelectric material can be of polycrystalline/ceramic or single crystalline formulation. In some embodiments the transducer elements can be formed using silicon using MEMs technology, including CMUT and PMUT designs.

In some embodiments, the function generator may comprise a field programmable gate array (FPGA) or other suitable function generator. The FPGA may be configured with parameters disclosed previously herein, including but not limited to frequency, pulse repetition frequency, bursts, burst numbers, where bursts may comprise pulses, numbers of pulses, length of pulses, pulse period, delays, burst repetition frequency or period, where sets of bursts may comprise a parameter set, where loop sets may comprise various parameter sets, with or without delays, or varied delays, where multiple loop sets may be repeated and/or new loop sets introduced, of varied time delay and independently controlled, and of various combinations and permutations of such, overall and throughout.

In some embodiments, the generator or amplifier may be configured to be a universal single-cycle or multi-cycle pulse generator, and to support driving via Class D or inductive driving, as well as across all envisioned clinical applications, use environments, also discussed in part later in this disclosure. In other embodiments, the class D or inductive current driver may be configured to comprise transformer and/or auto-transformer driving circuits to further provide step up/down components, and in some cases, to preferably allow a step up in the amplitude. They may also comprise specific protective features, to further support the system, and provide capability to protect other parts of the system (e.g., therapy transducer and/or amplifier circuit components) and/or the user, from various hazards, including but not limited to, electrical safety hazards, which may potentially lead to use environment, system and therapy system, and user harms, damage or issues.

Disclosed generators may allow and support the ability of the system to select, vary and control various parameters (through enabled software tools), including, but not limited to those previously disclosed, as well as the ability to start/stop therapy, set and read voltage level, pulse and/or burst repetition frequency, number of cycles, duty ratio, channel enabled and delay, etc., modulate pulse amplitude on a fast time-scale independent of a high voltage supply, and/or other service, diagnostic or treatment features.

In some embodiments, the Therapy sub-system and/or components of, such as the amplifier, may comprise further integrated computer processing capability and may be networked, connected, accessed, and/or be removable/portable, modular, and/or exchangeable between systems, and/or driven/commanded from/by other systems, or in various combinations. Other systems may include other acoustic cavitation/histotripsy, HIFU, HITU, radiation therapy, radiofrequency, microwave, and cryoablation systems, navigation and localization systems, open surgical, laparoscopic, single incision/single port, endoscopic and non-invasive surgical robots, laparoscopic or surgical towers comprising other energy-based or vision systems, surgical system racks or booms, imaging carts, etc.

In some embodiments, one or more amplifiers may comprise a Class D amplifier and related drive circuitry including matching network components. Depending on the transducer element electric impedance and choice of the matching network components (e.g., an LC circuit made of an inductor L1 in series and the capacitor C1 in parallel), the combined impedance can be aggressively set low in order to have high amplitude electric waveform necessary to drive the transducer element. The maximum amplitude that Class D amplifiers is dependent on the circuit components used, including the driving MOSFET/IGBT transistors, matching network components or inductor, and transformer or auto-transformer, and of which may be typically in the low kV (e.g., 1-3 kV) range.

Therapy transducer element(s) are excited with an electrical waveform with an amplitude (voltage) to produce a pressure output sufficient for Histotripsy therapy. The excitation electric field can be defined as the necessary waveform voltage per thickness of the piezoelectric element. For example, because a piezoelectric element operating at 1 MHz transducer is half the thickness of an equivalent 500 kHz element, it will require half the voltage to achieve the same electric field and surface pressure.

The Therapy sub-system may also comprise therapy transducers of various designs and working parameters, supporting use in various procedures (and procedure settings). Systems may be configured with one or more therapy transducers, that may be further interchangeable, and work with various aspects of the system in similar or different ways (e.g., may interface to a robotic arm using a common interface and exchange feature, or conversely, may adapt to work differently with application specific imaging probes, where different imaging probes may interface and integrate with a therapy transducer in specifically different ways).

Therapy transducers may be configured of various parameters that may include size, shape (e.g., rectangular or round; anatomically curved housings, etc.), geometry, focal length, number of elements, size of elements, distribution of elements (e.g., number of rings, size of rings for annular patterned transducers), frequency, enabling electronic beam steering, etc. Transducers may be composed of various materials (e.g., piezoelectric, silicon, etc.), form factors and types (e.g., machined elements, chip-based, etc.) and/or by various methods of fabrication of.

Transducers may be designed and optimized for clinical applications (e.g., abdominal tumors, peripheral vascular disease, fat ablation, etc.) and desired outcomes (e.g., acoustic cavitation/histotripsy without thermal injury to intervening tissue), and affording a breadth of working ranges, including relatively shallow and superficial targets (e.g., thyroid or breast nodules), versus, deeper or harder to reach targets, such as central liver or brain tumors. They may be configured to enable acoustic cavitation/histotripsy under various parameters and sets of, as enabled by the aforementioned system components (e.g., function generator and amplifier, etc.), including but not limited to frequency, pulse repetition rate, pulses, number of pulses, pulse length, pulse period, delays, repetitions, sync delays, sync period, sync pulses, sync pulse delays, various loop sets, others, and permutations of. The transducer may also be designed to allow for the activation of a drug payload either deposited in tissue through various means including injection, placement or delivery in micelle or nanostructures.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The aforementioned components may be also integrated into the system's Therapy sub-system components wherein probes, imaging arrays, or the like, and electrically, mechanically or electromechanically integrated into therapy transducers.

This may afford, in part, the ability to have geometrically aligned imaging and therapy, with the therapy directly within the field of view, and in some cases in line, with imaging. In some embodiments, this integration may comprise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe) and/or other parameters, including moving/adjusting dynamically while actively imaging. The imaging component or probe may be encoded so its orientation and position relative to another aspect of the system, such as the therapy transducer, and/or robotically-enabled positioning component may be determined.

In one embodiment, the system may comprise onboard ultrasound, further configured to allow users to visualize, monitor and receive feedback for procedure sites through the system displays and software, including allowing ultrasound imaging and characterization (and various forms of), ultrasound guided planning and ultrasound guided treatment, all in real-time. The system may be configured to allow users to manually, semi-automated or in fully automated means image the patient (e.g., by hand or using a robotically-enabled imager).

In some embodiments, imaging feedback and monitoring can include monitoring changes in: backscatter from bubble clouds; speckle reduction in backscatter; backscatter speckle statistics; mechanical properties of tissue (i.e., elastography); tissue perfusion (i.e., ultrasound contrast); shear wave propagation; acoustic emissions, electrical impedance tomography, and/or various combinations of, including as displayed or integrated with other forms of imaging (e.g., CT or MRI).

In some embodiments, imaging including feedback and monitoring from backscatter from bubble clouds, may be used as a method to determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses or be configured to passively detect cavitation. Moreover, the nature of the feedback received can be used to adjust acoustic parameters (and associated system parameters) to optimize the drug delivery and/or tissue erosion process.

In some embodiments, imaging including feedback and monitoring from backscatter, and speckle reduction, may be configured in the system.

For systems comprising feedback and monitoring via backscattering, and as means of background, as tissue is progressively mechanically subdivided, in other words homogenized, disrupted, or eroded tissue, this process results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound.

After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems, including those disclosed herein, may also be used to evaluate the backscatter changes.

Further, systems comprising feedback and monitoring via speckle, and as means of background, an image may persist from frame to frame and change very little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique may permit early observation of changes resulting from the acoustic cavitation/histotripsy process and can identify changes in tissue before substantial or complete tissue effect (e.g., erosion occurs). In one embodiment, this method may be used to monitor the acoustic cavitation/histotripsy process for enhanced drug delivery where treatment sites/tissue is temporally disrupted, and tissue damage/erosion is not desired. In other embodiments, this may comprise speckle decorrelation by movement of scatters in an increasingly fluidized therapy volume. For example, in the case where partial or complete tissue erosion is desired.

For systems comprising feedback and monitoring via elastography, and as means of background, as treatment sites/tissue are further subdivided per an acoustic cavitation/histotripsy effect (homogenized, disrupted, or eroded), its mechanical properties change from a soft but interconnected solid to a viscous fluid or paste with few long-range interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histotripsy treatment allowing the state of tissue disruption to be determined by imaging or other quantitative means.

Systems may also comprise feedback and monitoring via shear wave propagation changes. As means of background, the subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. In one system embodiment, the system and supporting sub-systems may be used to generate and measure the interacting shear waves. For example, two adjacent ultrasound foci might perturb tissue by pushing it in certain ways. If adjacent foci are in a fluid, no shear waves propagate to interact with each other.

If the tissue is not fluidized, the interaction would be detected with external means, for example, by a difference frequency only detected when two shear waves interact nonlinearly, with their disappearance correlated to tissue damage. As such, the system may be configured to use this modality to enhance feedback and monitoring of the acoustic cavitation/histotripsy procedure.

For systems comprising feedback and monitoring via acoustic emission, and as means of background, as a tissue volume is subdivided, its effect on acoustic cavitation/histotripsy (e.g., the bubble cloud here) is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy, and may be configured as a feature of the system.

For systems comprising feedback and monitoring via electrical impedance tomography, and as means of background, an impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the acoustic cavitation/histotripsy (e.g., bubble cloud, specifically) and histotripsy process can be monitored using this as configured in the system and supporting sub-systems.

The user may be allowed to further select, annotate, mark, highlight, and/or contour, various regions of interest or treatment sites, and defined treatment targets (on the image (s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses.

The system may further include the ability to conduct image registration, including imaging and image data set registration to allow navigation and localization of the system to the patient, including the treatment site (e.g., tumor, critical structure, bony anatomy, anatomy and identifying features of, etc.). In one embodiment, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's Therapy and Robotics sub-systems to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and Robotics sub-system tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci*Xi system) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Systems disclosed herein may also comprise all or some of their sub-system hardware packaged within the other system cart/console/systems described here (e.g., acoustic cavitation/histotripsy system and/or sub-systems integrated and operated from said navigation or laparoscopic system).

The system may also be configured, through various aforementioned parameters and other parameters, to display real-time visualization of a bubble cloud in a spatial-temporal manner, including the resulting tissue effect peri/post-treatment from tissue/bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), and/or where the other procedure further require invasive approaches (e.g., incisions or punctures) and iterative imaging in a scanner between procedure steps (e.g., CT or MRI scanning). The above disclosed systems, sub-systems, components, modalities, features and work-flows/methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Robotics

They system may comprise various Robotic sub-systems and components, including but not limited to, one or more robotic arms and controllers, which may further work with other sub-systems or components of the system to deliver and monitor acoustic cavitation/histotripsy. As previously discussed herein, robotic arms and control systems may be integrated into one or more Cart configurations.

For example, one system embodiment may comprise a Cart with an integrated robotic arm and control system, and Therapy, Integrated Imaging and Software, where the robotic arm and other listed sub-systems are controlled by the user through the form factor of a single bedside Cart.

In other embodiments, the Robotic sub-system may be configured in one or more separate Carts, that may be a driven in a master/slave configuration from a separate master or Cart, wherein the robotically-enabled Cart is positioned bed/patient-side, and the Master is at a distance from said Cart.

Disclosed robotic arms may be comprised of a plurality of joints, segments, and degrees of freedom and may also include various integrated sensor types and encoders, implemented for various use and safety features. Sensing technologies and data may comprise, as an example, vision, potentiometers, position/localization, kinematics, force, torque, speed, acceleration, dynamic loading, and/or others. In some cases, sensors may be used for users to direct robot commands (e.g., hand gesture the robot into a preferred set up position, or to dock home). Additional details on robotic arms can be found in US Patent Pub. No. 2013/0255426 to Kassow et al. which is disclosed herein by reference in its entirety.

The robotic arm receives control signals and commands from the robotic control system, which may be housed in a Cart. The system may be configured to provide various functionalities, including but not limited to, position, tracking, patterns, triggering, and events/actions.

Position may be configured to comprise fixed positions, pallet positions, time-controlled positions, distance-controlled positions, variable-time controlled positions, variable-distance controlled positions.

Tracking may be configured to comprise time-controlled tracking and/or distance-controlled tracking.

The patterns of movement may be configured to comprise intermediate positions or waypoints, as well as sequence of positions, through a defined path in space.

Triggers may be configured to comprise distance measuring means, time, and/or various sensor means including those disclosed herein, and not limited to, visual/imaging-based, force, torque, localization, energy/power feedback and/or others.

Events/actions may be configured to comprise various examples, including proximity-based (approaching/departing a target object), activation or de-activation of various end-effectors (e.g., therapy transducers), starting/stopping/pausing sequences of said events, triggering or switching between triggers of events/actions, initiating patterns of movement and changing/toggling between patterns of movement, and/or time-based and temporal over the defined work and time-space.

In one embodiment, the system comprises a three degree of freedom robotic positioning system, enabled to allow the user (through the software of the system and related user interfaces), to micro-position a therapy transducer through X, Y, and Z coordinate system, and where gross macro-positioning of the transducer (e.g., aligning the transducer on the patient's body) is completed manually. In some embodiments, the robot may comprise 6 degrees of freedom including X, Y, Z, and pitch, roll and yaw. In other embodiments, the Robotic sub-system may comprise further degrees of freedom, that allow the robot arm supporting base to be positioned along a linear axis running parallel to the general direction of the patient surface, and/or the supporting base height to be adjusted up or down, allowing the position of the robotic arm to be modified relative to the patient, patient surface, Cart, Coupling sub-system, additional robots/robotic arms and/or additional surgical systems, including but not limited to, surgical towers, imaging systems, endoscopic/laparoscopic systems, and/or other.

One or more robotic arms may also comprise various features to assist in maneuvering and modifying the arm position, manually or semi-manually, and of which said features may interface on or between the therapy transducer and the most distal joint of the robotic arm. In some embodiments, the feature is configured to comprise a handle allowing maneuvering and manual control with one or more hands. The handle may also be configured to include user input and electronic control features of the robotic arm, to command various drive capabilities or modes, to actuate the robot to assist in gross or fine positioning of the arm (e.g., activating or deactivating free drive mode). The work-flow for the initial positioning of the robotic arm and therapy head can be configured to allow either first positioning the therapy transducer/head in the coupling solution, with the therapy transducer directly interfaced to the arm, or in a different work-flow, allowing the user to set up the coupling solution first, and enabling the robot arm to be interfaced to the therapy transducer/coupling solution as a later/terminal set up step.

In some embodiments, the robotic arm may comprise a robotic arm on a laparoscopic, single port, endoscopic, hybrid or combination of, and/or other robot, wherein said robot of the system may be a slave to a master that controls said arm, as well as potentially a plurality of other arms, equipped to concurrently execute other tasks (vision, imaging, grasping, cutting, ligating, sealing, closing, stapling, ablating, suturing, marking, etc.), including actuating one or more laparoscopic arms (and instruments) and various histotripsy system components. For example, a laparoscopic robot may be utilized to prepare the surgical site, including manipulating organ position to provide more ideal acoustic access and further stabilizing said organ in some cases to minimize respiratory motion. In conjunction and parallel to this, a second robotic arm may be used to deliver non-invasive acoustic cavitation through a body cavity, as observed under real-time imaging from the therapy transducer (e.g., ultrasound) and with concurrent visualization via a laparoscopic camera. In other related aspects, a similar approach may be utilized with a combination of an endoscopic and non-invasive approach, and further, with a combination of an endoscopic, laparoscopic and non-invasive approach.

Software

The system may comprise various software applications, features and components which allow the user to interact, control and use the system for a plethora of clinical applications. The Software may communicate and work with one or more of the sub-systems, including but not limited to Therapy, Integrated Imaging, Robotics and Other Components, Ancillaries and Accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and maybe used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. Said points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the aforementioned Robotics sub-system, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

OTHER COMPONENTS, ANCILLARIES AND ACCESSORIES

The system may comprise various other components, ancillaries and accessories, including but not limited to computers, computer processors, power supplies including high voltage power supplies, controllers, cables, connectors, networking devices, software applications for security, communication, integration into information systems including hospital information systems, cellular communication devices and modems, handheld wired or wireless controllers, goggles or glasses for advanced visualization, augmented or virtual reality applications, cameras, sensors, tablets, smart devices, phones, internet of things enabling capabilities, specialized use "apps" or user training materials and applications (software or paper based), virtual proctors or trainers and/or other enabling features, devices, systems or applications, and/or methods of using the above.

System Variations and Methods/Applications

In addition to performing a breadth of procedures, the system may allow additional benefits, such as enhanced planning, imaging and guidance to assist the user. In one embodiment, the system may allow a user to create a patient, target and application specific treatment plan, wherein the system may be configured to optimize treatment parameters based on feedback to the system during planning, and where planning may further comprise the ability to run various test protocols to gather specific inputs to the system and plan.

Feedback may include various energy, power, location, position, tissue and/or other parameters.

The system, and the above feedback, may also be further configured and used to autonomously (and robotically) execute the delivery of the optimized treatment plan and protocol, as visualized under real-time imaging during the procedure, allowing the user to directly observe the local treatment tissue effect, as it progresses through treatment, and start/stop/modify treatment at their discretion. Both test and treatment protocols may be updated over the course of the procedure at the direction of the user, or in some embodiments, based on logic embedded within the system.

It is also recognized that many of these benefits may further improve other forms of acoustic therapy, including thermal ablation with high intensity focused ultrasound (HIFU), high intensity therapeutic ultrasound (HITU) including boiling histotripsy (thermal cavitation), and are considered as part of this disclosure. The disclosure also considers the application of histotripsy as a means to activate previously delivered in active drug payloads whose activity is inert due to protection in a micelle, nanostructure or similar protective structure or through molecular arrangement that allows activation only when struck with acoustic energy.

In another aspect, the Therapy sub-system, comprising in part, one or more amplifiers, transducers and power supplies, may be configured to allow multiple acoustic cavitation and histotripsy driving capabilities, affording specific benefits based on application, method and/or patient specific use. These benefits may include, but are not limited to, the ability to better optimize and control treatment parameters, which may allow delivery of more energy, with more desirable thermal profiles, increased treatment speed and reduced procedure times, enable electronic beam steering and/or other features.

This disclosure also includes novel systems and concepts as related to systems and sub-systems comprising new and "universal" amplifiers, which may allow multiple driving approaches (e.g., single and multi-cycle pulsing). In some embodiments, this may include various novel features to further protect the system and user, in terms of electrical safety or other hazards (e.g., damage to transducer and/or amplifier circuitry).

In another aspect, the system, and Therapy sub-system, may include a plethora of therapy transducers, where said therapy transducers are configured for specific applications and uses and may accommodate treating over a wide range of working parameters (target size, depth, location, etc.) and may comprise a wide range of working specifications (detailed below). Transducers may further adapt, interface and connect to a robotically-enabled system, as well as the Coupling sub-system, allowing the transducer to be positioned within, or along with, an acoustic coupling device allowing, in many embodiments, concurrent imaging and histotripsy treatments through an acceptable acoustic window. The therapy transducer may also comprise an integrated imaging probe or localization sensors, capable of displaying and determining transducer position within the treatment site and affording a direct field of view (or representation of) the treatment site, and as the acoustic cavitation/histotripsy tissue effect and bubble cloud may or may not change in appearance and intensity, throughout the treatment, and as a function of its location within said treatment (e.g., tumor, healthy tissue surrounding, critical structures, adipose tissue, etc.).

The systems, methods and use of the system disclosed herein, may be beneficial to overcoming significant unmet needs in the areas of soft tissue ablation, oncology, immuno-oncology, advanced image guided procedures, surgical procedures including but not limited to open, laparoscopic, single incision, natural orifice, endoscopic, non-invasive, various combination of, various interventional spaces for catheter-based procedures of the vascular, cardiovascular pulmonary and/or neurocranial-related spaces, cosmetics/aesthetics, metabolic (e.g., type 2 diabetes), plastic and reconstructive, ocular and ophthalmology, orthopedic, gynecology and men's health, and other systems, devices and methods of treating diseased, injured, undesired, or healthy tissues, organs or cells.

Systems and methods are also provided for improving treatment patterns within tissue that can reduce treatment time, improve efficacy, and reduce the amount of energy and prefocal tissue heating delivered to patients.

Use Environments

The disclosed system, methods of use, and use of the system, may be conducted in a plethora of environments and settings, with or without various support systems such as anesthesia, including but not limited to, procedure suites, operating rooms, hybrid rooms, in and out-patient settings, ambulatory settings, imaging centers, radiology, radiation therapy, oncology, surgical and/or any medical center, as well as physician offices, mobile healthcare centers or systems, automobiles and related vehicles (e.g., van), aero and marine transportation vehicles such as planes and ships, and/or any structure capable of providing temporary procedure support (e.g., tent). In some cases, systems and/or sub-systems disclosed herein may also be provided as integrated features into other environments, for example, the direct integration of the histotripsy Therapy sub-system into a MRI scanner or patient surface/bed, wherein at a minimum the therapy generator and transducer are integral to such, and in other cases wherein the histotripsy configuration further includes a robotic positioning system, which also may be integral to a scanner or bed centered design.

Coupling

Systems may comprise a variety of Coupling sub-system embodiments, of which are enabled and configured to allow acoustic coupling to the patient to afford effective acoustic access for ultrasound visualization and acoustic cavitation/histotripsy (e.g., provide acoustic window and medium between the transducer(s) and patient, and support of). These may include different form factors of such, including open and enclosed device solutions, and some arrangements which may be configured to allow dynamic control over the acoustic medium (e.g., temperature, dissolved gas content, level of particulate filtration, sterility, volume, composition, etc.). Such dynamic control components may be directly integrated to the system (within the Cart), or may be in temporary/intermittent or continuous communication with the system, but externally situated in a separate device and/or cart.

The Coupling sub-system typically comprises, at a minimum, coupling medium (e.g., degassed water or water solutions), a reservoir/container to contain said coupling medium, and a support structure (including interfaces to other surfaces or devices). In most embodiments, the coupling medium is water, and wherein the water may be conditioned before or during the procedure (e.g., chilled, degassed, filtered, etc.). Various conditioning parameters may be employed based on the configuration of the system and its intended use/application.

The reservoir or medium container may be formed and shaped to various sizes and shapes, and to adapt/conform to the patient, allow the therapy transducer to engage/access and work within the acoustic medium, per defined and required working space (minimum volume of medium to allow the therapy transducer to be positioned and/or move through one or more treatment positions or patterns, and at various standoffs or depths from the patient, etc.), and wherein said reservoir or medium container may also mechanically support the load, and distribution of the load, through the use of a mechanical and/or electromechanical support structure. As a representative example, this may include a support frame. The container may be of various shapes, sizes, curvatures, and dimensions, and may be comprised of a variety of materials compositions (single, multiple, composites, etc.), of which may vary throughout. In some embodiments, it may comprise features such as films, drapes, membranes, bellows, etc. that may be insertable and removable, and/or fabricated within, of which may be used to conform to the patient and assist in confining/containing the medium within the container. It may further contain various sensors (e.g., volume/fill level), drains (e.g., inlet/outlet), lighting (e.g., LEDs), markings (e.g., fill lines, set up orientations, etc.), text (e.g., labeling), etc.

In one embodiment, the reservoir or medium container contains a sealable frame, of which a membrane and/or film may be positioned within, to afford a conformable means of contacting the reservoir (later comprising the treatment head/therapy transducer) as an interface to the patient, that further provides a barrier to the medium (e.g., water) between the patient and therapy transducer). In other embodiments, the membrane and/or film may comprise an opening, the patient contacting edge of which affords a fluid/mechanical seal to the patient, but in contrast allows medium communication directly with the patient (e.g., direct degassed water interface with patient). The superstructure of the reservoir or medium container in both these examples may further afford the proximal portion of the structure (e.g., top) to be open or enclosed (e.g., to prevent spillage or afford additional features).

Disclosed membranes may be comprised of various elastomers, viscoelastic polymers, thermoplastics, thermoplastic elastomers, thermoset polymers, silicones, urethanes, rigid/flexible co-polymers, block co-polymers, random block co-polymers, etc. Materials may be hydrophilic, hydrophobic, surface modified, coated, extracted, etc., and may also contain various additives to enhance performance, appearance or stability. In some embodiments, the thermoplastic elastomer may be styrene-ethylene-butylene-styrene (SEBS), or other like strong and flexible elastomers. The membrane form factor can be flat or pre-shaped prior to use. In other embodiments, the membrane could be inelastic (i.e., a convex shape) and pressed against the patient's skin to acoustically couple the transducer to the tissue. Systems and methods are further disclosed to control the level of contaminants (e.g., particulates, etc.) on the membrane to maintain the proper level of ultrasound coupling. Too many particulates or contaminants can cause scattering of the ultrasound waves. This can be achieved with removable films or coatings on the outer surfaces of the membrane to protect against contamination.

Said materials may be formed into useful membranes through molding, casting, spraying, ultrasonic spraying, extruding, and/or any other processing methodology that produces useful embodiments. They may be single use or reposable/reusable. They may be provided non-sterile, aseptically cleaned or sterile, where sterilization may comprise any known method, including but not limited to ethylene oxide, gamma, e-beam, autoclaving, steam, peroxide, plasma, chemical, etc. Membranes can be further configured with an outer molded or over molded frame to provide mechanical stability to the membrane during handling including assembly, set up and take down of the coupling sub-system. Various parameters of the membrane can be optimized for this method of use, including thickness, thickness profile, density, formulation (e.g., polymer molecular weight and copolymer ratios, additives, plasticizers, etc.), including optimizing specifically to maximize acoustic transmission properties, including minimizing impact to cavitation initiation threshold values, and/or ultrasound imaging artifacts, including but not limited to membrane reflections, as representative examples.

Open reservoirs or medium containers may comprise various methods of filling, including using pre-prepared medium or water, that may be delivered into the containers, in some cases to a defined specification of water (level of temperature, gas saturation, etc.), or they may comprise additional features integral to the design that allow filling and draining (e.g., ports, valves, hoses, tubing, fittings, bags, pumps, etc.). These features may be further configured into or to interface to other devices, including for example, a fluidics system. In some cases, the fluidics system may be an in-house medium preparation system in a hospital or care setting room, or conversely, a mobile cart-based system which can prepare and transport medium to and from the cart to the medium container, etc.

Enclosed iterations of the reservoir or medium container may comprise various features for sealing, in some embodiments sealing to a proximal/top portion or structure of a reservoir/container, or in other cases where sealing may comprise embodiments that seal to the transducer, or a feature on the transducer housings. Further, some embodiments may comprise the dynamic ability to control the volume of fluid within these designs, to minimize the potential for air bubbles or turbulence in said fluid and to allow for changes in the focal length to the target area without moving the transducer. As such, integrated features allowing fluid communication, and control of, may be provided (ability to provide/remove fluid on demand), including the ability to monitor and control various fluid parameters, some disclosed above. In order to provide this functionality, the overall system, and as part, the Coupling sub-system, may comprise a fluid conditioning system, which may contain various electromechanical devices, systems, power, sensing, computing, pumping, filtering and control systems, etc. The reservoir may also be configured to receive signals that cause it to deform or change shape in a specific and controlled manner to allow the target point to be adjusted without moving the transducer.

Coupling support systems may include various mechanical support devices to interface the reservoir/container and medium to the patient, and the workspace (e.g., bed, floor, etc.). In some embodiments, the support system comprises a mechanical arm with 3 or more degrees of freedom. Said arm may have a proximal interface with one or more locations (and features) of the bed, including but not limited to, the frame, rails, customized rails or inserts, as well as one or more distal locations of the reservoir or container. The arm may also be a feature implemented on one or more Carts, wherein Carts may be configured in various unlimited permutations, in some cases where a Cart only comprises the role of supporting and providing the disclosed support structure.

In some embodiments, the support structure and arm may be a robotically-enabled arm, implemented as a stand-alone Cart, or integrated into a Cart further comprising two or more system sub-systems, or where in the robotically-enabled arm is an arm of another robot, of interventional, surgical or other type, and may further comprise various user input features to actuate/control the robotic arm (e.g., positioning into/within coupling medium) and/or Coupling solution features (e.g., filling, draining, etc.). In some examples, the support structure robotic arm positional encoders may be used to coordinate the manipulation of the second arm (e.g. comprising the therapy transducer/treatment head), such as to position the therapy transducer to a desired/known location and pose within the coupling support structure.

Overall, significant unmet needs exist in interventional and surgical medical procedures today, including those procedures utilizing minimally invasive devices and approaches to treat disease and/or injury, and across various types of procedures where the unmet needs may be solved with entirely new medical procedures. Today's medical system capabilities are often limited by access, wherein a less or non-invasive approach would be preferred, or wherein today's tools aren't capable to deliver preferred/required tissue effects (e.g., operate around/through critical structures without serious injury), or where the physical set up of the systems makes certain procedure approaches less desirable or not possible, and where a combination of approaches, along with enhanced tissue effecting treatments, may enable entirely new procedures and approaches, not possible today.

In addition, specific needs exist for enabling histotripsy delivery, including robotic histotripsy delivery, wherein one or more histotripsy therapy transducers may be configured to acoustically couple to a patient, using a completely sealed approach (e.g., no acoustic medium communication with the patient's skin) and allowing the one or more histotripsy transducers to be moved within the coupling solution without impeding the motion/movement of the robotic arm or interfering/disturbing the coupling interface, which could affect the intended treatment and/or target location.

Disclosed herein are histotripsy acoustic and patient coupling systems and methods, to enable histotripsy therapy/treatment, as envisioned in any setting, from interventional suite, operating room, hybrid suites, imaging centers, medical centers, office settings, mobile treatment centers, and/or others, as non-limiting examples. The following disclosure further describes novel systems used to create, control, maintain, modify/enhance, monitor and setup/takedown acoustic and patient coupling systems, in a variety of approaches, methods, environments, architectures and work-flows. In general, the disclosed novel systems may allow for a coupling medium, in some examples degassed water, to be interfaced between a histotripsy therapy transducer and a patient, wherein the acoustic medium provides sufficient acoustic coupling to said patient, allowing the delivery of histotripsy pulses through a user desired treatment location (and volume), where the delivery may require physically moving the histotripsy therapy transducer within a defined work-space comprising the coupling medium, and also where the coupling system is configured to allow said movement of the therapy transducer (and positioning system, e.g., robot) freely and unencumbered from by the coupling support system (e.g., a frame or manifold holding the coupling medium).

Coupling System and Sub-Systems/Components

Figure 2:
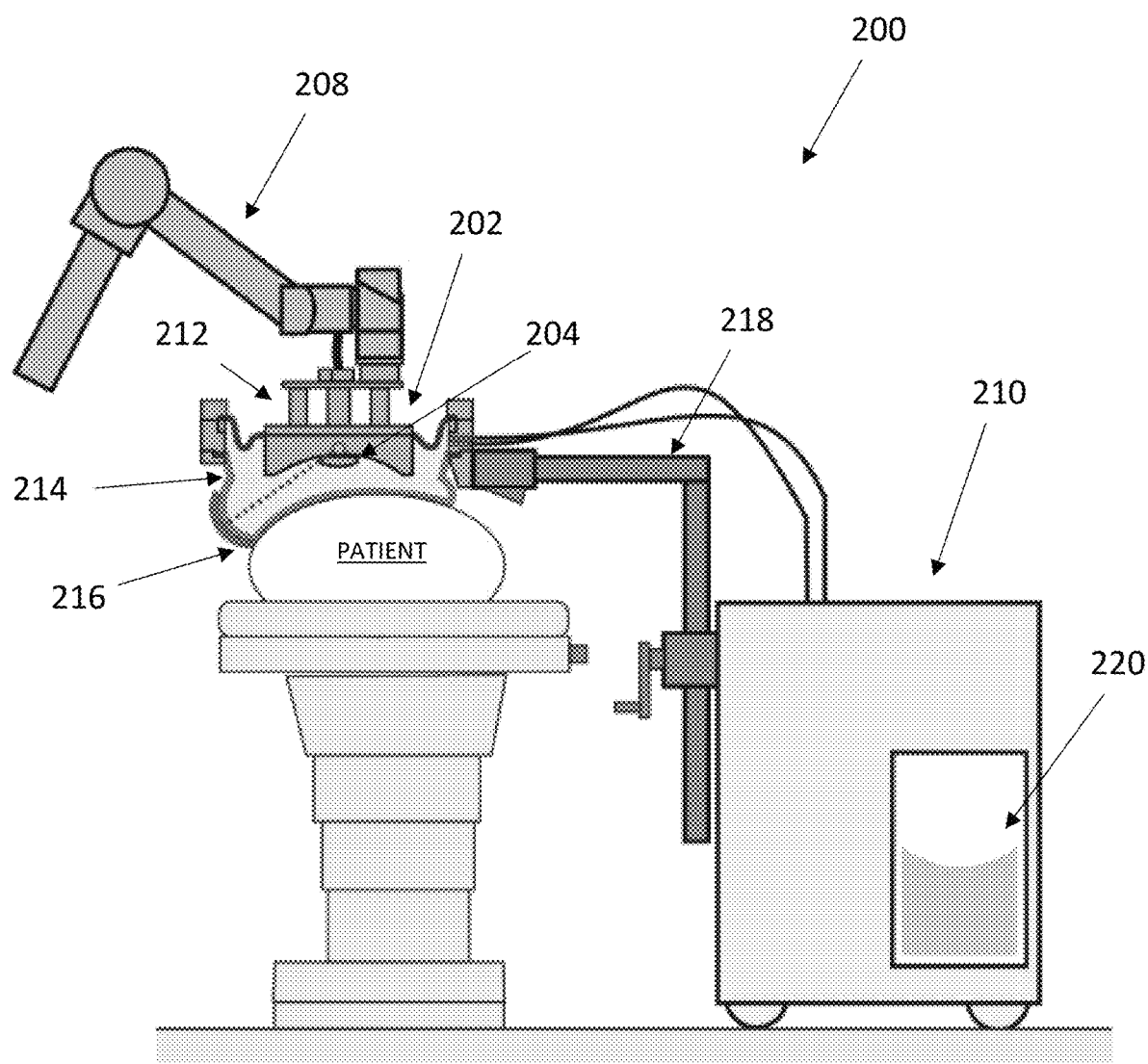
FIG. 2 is one embodiment of a histotripsy therapy and imaging system with a coupling system.

The disclosed histotripsy acoustic and patient coupling systems, in general, may comprise one or more of the following sub-systems and components, an example of which is depicted in FIG. 2, including but not limited to 1) a membrane/barrier film to provide an enclosed, sealed and conformal patient coupling and histotripsy system interface, 2) a frame and assembly to retain the membrane and provide sufficient work and head space for a histotripsy therapy transducers required range of motion (x, y and z, pitch, roll and yaw), 3) a sufficient volume of ultrasound medium to afford acoustic coupling and interfaces to a histotripsy therapy transducer and robotic arm, 4) one or more mechanical support arms to allow placement, positioning and load support of the frame, assembly and medium and 5) a fluidics system to prepare, provide and remove ultrasound medium (s) from the frame and assembly.

In some embodiments, the coupling system may be fully sealed, and in other embodiments and configurations, it may be partially open to afford immediate access (physical and/or visual).

The acoustic and patient coupling systems and sub-systems may further comprise various features and functionality, and associated work-flows, and may also be configured in a variety of ways to enable histotripsy procedures as detailed below.

FIG. 2 illustrates one embodiment of a histotripsy therapy and imaging system 200, including a coupling assembly 212. As described above, a histotripsy therapy and imaging system can include a therapy transducer 202, an imaging system 204, a robotic positioning arm 208, and a cart 210.

The therapy and/or imaging transducers can be housed in a coupling assembly 212 which can further include a coupling membrane 214 and a membrane constraint 216 configured to prevent the membrane from expanding too far from the transducer. The coupling membrane can be filled with an acoustic coupling medium such as a fluid or a gel. The membrane constraint can be, for example, a semi-rigid or rigid material configured to restrict expansion/movement of the membrane. In some embodiments, the membrane constraint is not used, and the elasticity and tensile strength of the membrane prevent over expansion. The coupling membrane can be a mineral-oil infused SEBS membrane to prevent direct fluid contact with the patient's skin. In the illustrated embodiment, the coupling assembly 212 is supported by a mechanical support arm 218 which can be load bearing in the x-y plane but allow for manual or automated z-axis adjustment. The mechanical support arm can be attached to the floor, the patient table, or the cart 210. The mechanical support is designed and configured to conform and hold the coupling membrane 214 in place against the patient's skin while still allowing movement of the therapy/imaging transducer relative to the patient and also relative to the coupling membrane 214 with the robotic positioning arm 208.

The system can further include a fluidics system 220 that can include a fluid source, a cooling and degassing system, and a programmable control system. The fluidics system is configured for external loading of the coupling membrane with automated control of fluidic sequences. Further details on the fluidics system 220 are provided below.

Membranes/Barrier Films and Related Architectures

Membranes and barrier films may be composed of various biocompatible materials which allow conformal coupling to patient anatomy with minimal or no entrapped bubbles capable of interfering with ultrasound imaging and histotripsy therapy, and that are capable of providing a sealed barrier layer between said patient anatomy and the ultrasound medium, of which is contained within the work-space provided by the frame and assembly.

Membrane and barrier film materials may comprise flexible and elastomeric biocompatible materials/polymers, such as various thermoplastic and thermoset materials, as well as permanent or bioresorbable polymers. Additionally, the frame of the UMC can also comprise the same materials. In some examples, the membrane may be rigid or semi-rigid polymers which are pre-shaped or flat.

Ultrasound Medium

As previously described, the ultrasound medium may comprise any applicable medium capable of providing sufficient and useful acoustic coupling to allow histotripsy treatments and enable sufficient clinical imaging (e.g., ultrasound). Ultrasound mediums, as a part of this disclosure and system, may comprise, but are not limited to, various aqueous solutions/mediums, including mixtures with other co-soluble fluids, of which may have preferred or more preferred acoustic qualities, including ability to match speed of sound, etc. Example mediums may comprise degassed water and/or mixtures/co-solutions of degassed water and various alcohols, such as ethanol.

Mechanical Support Arms and Arm Architectures

In order to support the acoustic and patient coupling system, including providing efficient and ergonomic workflows for users, various designs and configurations of mechanical support arms (and arm architectures) may be employed. Support arms may be configured with a range of degrees of freedom, including but not limited to allowing, x, y, z, pitch, roll and yaw, as well additional interfacing features that may allow additional height adjustment or translation.

Arms may comprise a varied number and type of joints and segments. Typically, arms may comprise a minimum of 2 segments. In some configurations, arms may comprise 3 to 5 segments.

Arms are also be configured to interface proximally to a main support base or base interface (e.g., robot, table, table/bed rail, cart, floor mount, etc.) and distally to the frame/assembly and overall "UMC" or "coupling solution". This specific distal interface may further include features for controlling position/orientation of the frame/assembly, at the frame/assembly interface.

For example, in some embodiments, the arm/frame interface may comprise a ball joint wrist. In another example, the interface may include use of a gimbal wrist or an adjustable pitch and roll controlled wrist. These interfaces may be further employed with specific user interfaces and inputs, to assist with interacting with the various wrists, of which may include additional handles or knobs (as an unlimited example), to further enable positioning the UMC/coupling solution. For example, a gimbal wrist may benefit from allowing the frame/assembly to have 3 degrees of freedom (independent of the arm degrees of freedom), including pitch, roll and yaw adjustments.

Support arms, configured with arm wrists, further interfaced with frames/assemblies, may comprise features such as brakes, including cable or electronic actuated brakes, and quick releases, which may interact with one or more axis, individually, or in groupings. They may also include electronic lift systems and base supports. In some embodiments, these lift systems/base supports are co-located with robot arm bases, wherein said robot arm is equipped with the histotripsy therapy transducer configured to fit/work within the enclosed coupling solution. In other embodiments, the support arm is located on a separate cart. In some cases, the separate cart may comprise a fluidics system or user console. In other embodiments, it is interfaced to a bed/table, including but not limited to a rail, side surface, and/or bed/table base. In other examples/embodiments, it's interfaced to a floor-based structure/footing, capable of managing weight and tipping requirements.

Fluidics Systems, Control Systems and System Architectures

As a part of overall fluidics management, histotripsy systems including acoustic/patient coupling systems, may be configured to include an automated fluidics system, which primarily is responsible for providing a reservoir for preparation and use of coupling medium, where preparation may include the ability to degas, chill, monitor, adjust, dispense/fill, and retrieve/drain coupling medium to/from the frame/assembly. The fluidics system may include an emergency high flow rate system for rapid draining of the coupling medium from the UMC. In some embodiments, the fluidics system can be configured for a single use of the coupling medium, or alternatively, for re-use of the medium. In some embodiments, the fluidics system can implement positive air pressure or vacuum to carry out leak tests of the UMC and membrane prior to filling with a coupling medium. Vacuum assist can also be used for removal of air from the UMC during the filling process. The fluidics system can further include filters configured to prevent particulate contamination from reaching the UMC.

The fluidics system may be implemented in the form of a mobile fluidics cart. The cart may comprise an input tank, drain tank, degassing module, fill pump, drain pump, inert gas tank, air compressor, tubing/connectors/lines, electronic and manual controls systems and input devices, power supplies and one or more batteries. The cart in some cases may also comprise a system check vessel/reservoir for evaluating histotripsy system performance and related system diagnostics (configured to accommodate a required water volume and work-space for a therapy transducer).

It should be understood that any feature described herein with respect to one embodiment can be substituted for or combined with any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of producing an enhanced excitation volume with histotripsy energy, comprising:
    positioning a focus of an ultrasound therapy transducer at a first focal location in a first discrete treatment location within a target tissue volume, the first focal location being positioned along a central axis of the ultrasound therapy transducer;
    delivering a first histotripsy pulse to the first focal location at a therapy pulse repetition frequency (PRF) to produce a first cavitation bubble cloud at the first focal location;
    electronically beam-steering the focus of the ultrasound therapy transducer to a second focal location in the first discrete treatment location that is at least partially outside of the central axis with a steering period equivalent to the therapy PRF;
    delivering a second histotripsy pulse to the second focal location at the therapy PRF to produce a second bubble cloud at the second focal location;
    electronically beam-steering the focus of the ultrasound therapy transducer to a third focal location at least partially inside the central axis with the steering period;
    delivering a third histotripsy pulse to the third focal location at the therapy PRF to produce a third bubble cloud at the third focal location;
    repeating electronically beam-steering the focus with the steering period and delivering histotripsy pulses at the therapy PRF to the first focal location, the second focal location, and the third focal location in the first discrete treatment location until a desired dose is applied to the first discrete treatment location; and mechanically positioning the focus of the ultrasound therapy transducer at a first focal location in a second discrete treatment location within the target tissue volume after the desired dose has been applied to the first discrete treatment location.

2. The method of claim 1, wherein a natural focus of the ultrasound therapy transducer array is located along the central axis.

3. The method of claim 2, wherein the first focal location comprises the natural focus.

4. The method of claim 1, wherein the second focal location partially overlaps with the central axis.

5. The method of claim 1, wherein the third focal location comprises is overlapped with the first focal location.

6. The method of claim 1, wherein electronically beam-steering to the second focal location comprises steering laterally.

7. The method of claim 1, wherein electronically beam-steering to the second focal location comprises steering laterally and axially.

8. An ultrasound therapy system, comprising;
a robotic positioning system;
an ultrasound therapy transducer array connected to the robotic positioning system;
a generator operatively coupled to the ultrasound therapy transducer array, the generator and ultrasound therapy transducer array being configured to deliver histotripsy pulses into a subject to generate a cavitation bubble cloud in the subject;
at least one processor operatively coupled to the robotic positioning system and the generator, the at least one processor being configured to control the robotic positioning system and the generator to provide histotripsy therapy to the subject according to a treatment plan that includes a plurality of discrete treatment locations within a target tissue volume of the subject by:
controlling the robotic positioning system to mechanically position a focus of the ultrasound therapy transducer array at a first focal location in a first discrete treatment location within the treatment plan, the first focal location being positioned along a central axis of the ultrasound therapy transducer array;
controlling the generator to deliver at least one histotripsy pulse at a therapy pulse repetition frequency (PRF) with the ultrasound therapy transducer array to form a first cavitation bubble cloud at the first focal location;
controlling the generator to electronically beam-steer the focus of the ultrasound therapy transducer to a second focal location in the first discrete treatment location that is at least partially outside the central axis with a steering period equivalent to the therapy PRF;
controlling the generator to deliver at least one histotripsy pulse to the second focal location at the therapy PRF to produce a second bubble cloud at the second focal location;
controlling the generator to electronically beam-steer the focus of the ultrasound therapy transducer to a third focal location in the first discrete treatment location that is at least partially inside the central axis with the steering period; and
controlling the generator to deliver at least one histotripsy pulse to the third focal location to produce a third bubble cloud at the third focal location at the therapy PRF;

repeating controlling the generator to electronically beam-steer the focus with the steering period and controlling the generator to deliver histotripsy pulses at the therapy PRF to the first focal location, the second focal location, and the third focal location in the first discrete treatment location until a desired dose is applied to the first discrete treatment location; and controlling the robotic positioning system to mechanically position the focus of the ultrasound therapy transducer at a first focal location in a second discrete treatment location within the target tissue volume after the desired dose has been applied to the first discrete treatment location.

9. The system of claim 8, wherein a natural focus of the ultrasound therapy transducer array is located along the central axis.

10. The system of claim 9, wherein the first focal location comprises the natural focus.

11. The system of claim 8, wherein the second focal location partially overlaps with the central axis.

12. The system of claim 8, wherein the third focal location is overlapped with the first focal location.

13. The system of claim 8, wherein controlling the generator to electronically beam-steer to the second focal location comprises steering laterally.

14. The system of claim 8, wherein controlling the generator to electronically beam-steer to the second focal location comprises steering laterally and axially.

15. An ultrasound therapy system, comprising;
an ultrasound therapy transducer array;
a generator operatively coupled to the ultrasound therapy transducer array, the generator and ultrasound therapy transducer array being configured to deliver histotripsy pulses into a subject to generate a cavitation bubble cloud in the subject;
at least one processor operatively coupled to the generator, the at least one processor being configured to control the generator to provide histotripsy therapy to the subject according to a treatment plan that includes a plurality of discrete treatment locations within a target tissue volume of the subject by:
controlling the generator to deliver at least one histotripsy pulse with the ultrasound therapy transducer array at a therapy pulse repetition frequency (PRF) to form a first cavitation bubble cloud at a first focal location in a first discrete treatment location within the treatment plan, the first focal location being positioned along a central axis of the ultrasound therapy transducer array;
controlling the generator to electronically beam-steer the focus of the ultrasound therapy transducer to a second focal location in the first discrete treatment location that is at least partially outside the central axis with a steering period equivalent to the therapy PRF;
controlling the generator to deliver at least one histotripsy pulse to the second focal location at the therapy PRF to produce a second bubble cloud at the second focal location;
controlling the generator to electronically beam-steer the focus of the ultrasound therapy transducer to a third focal location in the first discrete treatment location that is at least partially inside the central axis with the steering period; and
controlling the generator to deliver at least one histotripsy pulse to the third focal location to produce a third bubble cloud at the third focal location at the therapy PRF;

repeating controlling the generator to electronically beam-steer the focus with the steering period and controlling the generator to deliver histotripsy pulses at the therapy PRF to the first focal location, the second focal location, and the third focal location in the first discrete treatment location until a desired dose is applied to the first discrete treatment location; and controlling the robotic positioning system to mechanically position the focus of the ultrasound therapy transducer at a first focal location in a second discrete treatment location within the target tissue volume after the desired dose has been applied to the first discrete treatment location.

16. The system of claim 15, wherein a natural focus of the ultrasound therapy transducer array is located along the central axis.

17. The system of claim 15, wherein the third focal location is overlapped with the first focal location.

* * * * *